(12) United States Patent
Lopez

(10) Patent No.: US 6,599,273 B1
(45) Date of Patent: Jul. 29, 2003

(54) FLUID TRANSFER DEVICE AND METHOD OF USE

(75) Inventor: George A. Lopez, Corona del Mar, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 09/489,189

(22) Filed: Jan. 20, 2000

(65) Prior Publication Data (65)

Related U.S. Application Data

(63) Continuation of application No. 09/150,580, filed on Sep. 10, 1998, now abandoned, which is a continuation of application No. 08/476,127, filed on Jun. 7, 1995, now abandoned, which is a continuation of application No. 08/265,095, filed on Jun. 24, 1994, now abandoned, which is a continuation-in-part of application No. 08/096,659, filed on Jul. 23, 1993, now Pat. No. 5,695,466, which is a continuation-in-part of application No. PCT/US92/10367, filed on Dec. 1, 1992, which is a continuation-in-part of application No. 07/813,073, filed on Dec. 18, 1991, now abandoned.

(51) Int. Cl.[7] ................................................ A61M 5/00
(52) U.S. Cl. .................... 604/249; 604/246; 604/411; 604/905; 604/256; 251/149.1
(58) Field of Search ................................. 604/246, 247, 604/249, 256, 264, 533, 537, 93.01, 411–413, 905, 86–88; 251/149.1; 128/912

(56) References Cited

U.S. PATENT DOCUMENTS

| | | | |
|---|---|---|---|
| 1,578,517 A | 3/1926 | Hein |
| 2,289,677 A | 7/1942 | Perelson |
| 2,342,215 A | 2/1944 | Perelson |
| 2,387,512 A | 10/1945 | Hilberg |
| 2,667,986 A | 2/1954 | Perelson |
| 2,847,995 A | 8/1958 | Adams |
| 3,134,380 A | 5/1964 | Armao |
| 3,135,261 A | 6/1964 | Carroll |
| 3,172,205 A | 3/1965 | Gammon |
| 3,193,154 A | 7/1965 | Bross |
| 3,352,395 A | 11/1967 | Huggins |
| 3,354,881 A | 11/1967 | Bloch |

(List continued on next page.)

FOREIGN PATENT DOCUMENTS

| | | |
|---|---|---|
| BG | 61386 | 1/1992 |
| CA | 1105959 | 7/1981 |

(List continued on next page.)

Primary Examiner—Michael J. Hayes
Assistant Examiner—Cris L. Rodriguez
(74) Attorney, Agent, or Firm—Knobbe, Martens, Olson & Bear, LLP

(57) ABSTRACT

A fluid transfer device comprising a hollow piercing element having a first end for receiving a standard syringe nose or other similar medical device and a second end having a tapered tip for accessing fluid inside a medication container is disclosed. In a preferred embodiment, the device has a disk-shaped stop for limiting entry of the piercing element into the vial. Preferably, the piercing element includes outwardly extending barbs which allow the device to be inserted into a vial but which prevent the device from being removed from the vial after insertion. After the syringe is disengaged from the device, the device and spent medication vial may be discarded as a unit. Alternatively, the device can remain attached to the vial, and a new syringe can be used to withdraw additional fluid from the vial when desired. In an alternate embodiment, a reusable, resealable valve is connected to the first end of the piercing element, which valve allows multiple syringes to be used with the piercing element. Various adaptors for using the device with intravascular (IV) lines and drip-bags are also disclosed.

13 Claims, 35 Drawing Sheets

FOREIGN PATENT DOCUMENTS

| | | |
|---|---|---|
| CN | 1077654 A | 10/1993 |
| DE | 855 319 | 9/1952 |
| DE | 84 25 197.2 | 10/1985 |
| EP | 0 114 677 | 8/1984 |
| EP | 0 237 321 | 3/1987 |
| EP | 0 240 590 | 4/1987 |
| EP | 0 240 987 | 4/1987 |
| EP | 0 309 771 | 9/1988 |
| EP | 0 309 771 | 4/1989 |
| EP | 0 399 119 | 7/1989 |
| EP | 0 446 469 | 12/1990 |
| NO | 310805 | 6/1994 |
| RU | 2 154 462 | 8/2000 |
| WO | WO 86/01712 | 3/1986 |
| WO | WO 86/03415 | 6/1986 |
| WO | WO 86/03416 | 6/1986 |
| WO | WO 91/06255 | 5/1991 |
| WO | WO 93/11828 | 6/1993 |

U.S. PATENT DOCUMENTS

| | | |
|---|---|---|
| 3,416,567 A | 12/1968 | Von Dardel et al. |
| 3,648,684 A | 3/1972 | Barnwell et al. |
| 3,788,519 A | 1/1974 | Mengal |
| 3,813,791 A | 6/1974 | Stewart et al. |
| 3,831,629 A | 8/1974 | Mackal et al. |
| 3,852,385 A | 12/1974 | Huggins |
| 3,974,832 A | 8/1976 | Kruck |
| 3,976,063 A | 8/1976 | Henneman et al. |
| 3,976,073 A | 8/1976 | Quick et al. |
| 3,986,508 A | 10/1976 | Barrington |
| 3,993,063 A | 11/1976 | Larrabee |
| 4,019,512 A | 4/1977 | Tenczar |
| 4,059,112 A | 11/1977 | Tischlinger |
| 4,076,285 A | 2/1978 | Martinez |
| 4,079,738 A | 3/1978 | Dunn et al. |
| 4,080,965 A | 3/1978 | Phillips |
| 4,121,585 A | 10/1978 | Becker, Jr. |
| 4,128,098 A | 12/1978 | Bloom et al. |
| 4,133,314 A | 1/1979 | Bloom et al. |
| 4,161,949 A | 7/1979 | Thanawalla |
| 4,187,846 A | 2/1980 | Lolachi et al. |
| 4,191,225 A | 3/1980 | Ogle |
| 4,201,208 A | 5/1980 | Cambio, Jr. |
| 4,214,779 A | 7/1980 | Losell |
| 4,219,912 A | 9/1980 | Adams |
| 4,294,249 A | 10/1981 | Sheehan et al. |
| 4,296,949 A | 10/1981 | Muetterties et al. |
| 4,306,705 A | 12/1981 | Svensson |
| 4,311,382 A | 1/1982 | Buckley et al. |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard et al. |
| 4,343,550 A | 8/1982 | Buckley et al. |
| 4,362,156 A | 12/1982 | Feller, Jr. et al. |
| 4,392,499 A | 7/1983 | Towse |
| 4,411,662 A | 10/1983 | Pearson |
| 4,417,890 A | 11/1983 | Dennehey et al. |
| 4,432,759 A | 2/1984 | Gross et al. |
| 4,432,765 A | 2/1984 | Oscarsson |
| 4,439,188 A | 3/1984 | Dennehey et al. |
| 4,439,193 A | 3/1984 | Larkin |
| 4,457,749 A | 7/1984 | Bellotti et al. |
| 4,461,091 A | 7/1984 | Gammon |
| 4,470,664 A | 9/1984 | Shirasawa |
| 4,508,367 A | 4/1985 | Oreopoulos et al. |
| 4,511,359 A | 4/1985 | Vaillancourt |
| 4,512,766 A | 4/1985 | Vailancourt |
| 4,535,820 A | 8/1985 | Raines |
| 4,564,054 A | 1/1986 | Gustavsson |
| 4,592,356 A | 6/1986 | Gutierrez |
| 4,607,868 A | 8/1986 | Harvey et al. |
| 4,610,469 A | 9/1986 | Wolff-Mooij |
| 4,614,437 A | 9/1986 | Buehler |
| 4,617,012 A | 10/1986 | Vaillancourt |
| 4,623,068 A | 11/1986 | Brown et al. |
| 4,624,667 A | 11/1986 | Rutnarak |
| 4,639,019 A | 1/1987 | Mittleman |
| 4,645,494 A | 2/1987 | Lee et al. |
| 4,666,429 A | 5/1987 | Stone |
| 4,673,400 A | 6/1987 | Martin |
| 4,706,487 A | 11/1987 | Bandou et al. |
| 4,725,267 A | 2/1988 | Vaillancourt |
| 4,735,607 A | 4/1988 | Keith, Jr. |
| 4,752,292 A | 6/1988 | Lopez et al. |
| 4,759,756 A | 7/1988 | Forman et al. |
| 4,775,369 A | 10/1988 | Schwartz |
| 4,781,702 A | 11/1988 | Herrli |
| 4,782,841 A | 11/1988 | Lopez |
| 4,784,650 A | 11/1988 | Coburn |
| 4,810,241 A | 3/1989 | Rogers |
| 4,826,500 A | 5/1989 | Rautsola |
| 4,832,214 A | 5/1989 | Schrader et al. |
| 4,834,664 A | 5/1989 | Lin |
| 4,846,809 A | 7/1989 | Sims |
| 4,850,978 A | 7/1989 | Dudar et al. |
| 4,874,377 A | 10/1989 | Newgard et al. |
| 4,875,291 A | 10/1989 | Panique et al. |
| 4,875,760 A | 10/1989 | Youngren et al. |
| 4,878,897 A | 11/1989 | Katzin |
| 4,880,414 A | 11/1989 | Whipple |
| 4,889,527 A | 12/1989 | Herrli |
| 4,898,452 A | 2/1990 | Kawachi et al. |
| 4,900,310 A | 2/1990 | Ogle, II |
| 4,907,879 A | 3/1990 | Webb |
| 4,915,687 A | 4/1990 | Sivert |
| 4,917,668 A | 4/1990 | Haindl |
| 4,928,212 A | 5/1990 | Benavides |
| 4,943,896 A | 7/1990 | Johnson |
| 4,950,260 A | 8/1990 | Bonaldo |
| 4,964,855 A | 10/1990 | Todd et al. |
| 4,969,883 A | 11/1990 | Gilbert et al. |
| 4,970,794 A | 11/1990 | Buckley |
| 4,979,941 A | 12/1990 | Ogle, II |
| 4,981,469 A | 1/1991 | Whitehouse et al. |
| 4,998,713 A | 3/1991 | Vaillancourt |
| 4,998,921 A | 3/1991 | Vickroy et al. |
| 4,998,927 A | 3/1991 | Vaillancourt |
| 5,006,114 A | 4/1991 | Rogers et al. |
| 5,009,490 A | 4/1991 | Kouno et al. |
| 5,018,532 A | 5/1991 | Etheredge, III |
| 5,024,616 A | 6/1991 | Ogle, II |
| 5,033,476 A | 7/1991 | Kasai |
| 5,046,456 A | 9/1991 | Heyman et al. |
| D321,250 S | 10/1991 | Jepson et al. |
| D321,251 S | 10/1991 | Jepson et al. |
| D321,252 S | 10/1991 | Jepson et al. |
| 5,064,416 A | 11/1991 | Newgard et al. |
| 5,065,783 A | 11/1991 | Ogle, II |
| 5,069,225 A | 12/1991 | Okamura |
| 5,100,394 A | 3/1992 | Dudar et al. |
| 5,122,123 A | 6/1992 | Vaillancourt |
| 5,134,489 A | 7/1992 | Sauer |
| 5,135,489 A | 8/1992 | Jepson et al. |
| 5,154,703 A | 10/1992 | Bonaldo |
| 5,158,554 A | 10/1992 | Jepson et al. |
| 5,163,230 A | 11/1992 | Gast |
| 5,163,922 A | 11/1992 | McElveen, Jr. et al. |
| 5,167,642 A | 12/1992 | Fowles |
| 5,167,647 A | 12/1992 | Wijkamp et al. |

| | | | | | |
|---|---|---|---|---|---|
| 5,167,648 A | 12/1992 | Jepson et al. | 5,385,547 A | 1/1995 | Wong et al. |
| 5,171,234 A | 12/1992 | Jepson et al. | 5,401,245 A | 3/1995 | Haining |
| 5,188,620 A | 2/1993 | Jepson et al. | 5,411,499 A | 5/1995 | Dudar et al. |
| 5,199,947 A | 4/1993 | Lopez et al. | 5,423,753 A | 6/1995 | Fowles et al. |
| 5,203,775 A | 4/1993 | Frank et al. | 5,439,451 A | 8/1995 | Collinson et al. |
| 5,211,638 A | 5/1993 | Dudar et al. | 5,470,319 A | 11/1995 | Mayer |
| 5,242,432 A | 9/1993 | DeFrank | 5,487,731 A | 1/1996 | Denton |
| 5,251,873 A | 10/1993 | Atkinson et al. | 5,509,912 A | 4/1996 | Vaillancourt et al. |
| 5,255,441 A | 10/1993 | Burgess et al. | 5,549,566 A | 8/1996 | Elias et al. |
| 5,256,155 A | 10/1993 | Yerlikaya et al. | 5,549,577 A | 8/1996 | Siegel et al. |
| 5,269,771 A | 12/1993 | Thomas et al. | 5,556,388 A | 9/1996 | Johlin, Jr. |
| 5,273,533 A | 12/1993 | Bonaldo | 5,694,686 A | 12/1997 | Lopez |
| 5,290,254 A | 3/1994 | Vaillancourt | 5,695,466 A | 12/1997 | Lopez et al. |
| 5,295,657 A | 3/1994 | Atkinson | 5,700,248 A | 12/1997 | Lopez |
| 5,323,539 A | 6/1994 | O'Neil | 5,730,418 A | 3/1998 | Feith et al. |
| 5,344,414 A | 9/1994 | Lopez et al. | 5,738,663 A | 4/1998 | Lopez |
| 5,380,306 A | 1/1995 | Brinon | 6,113,068 A | 9/2000 | Ryan |

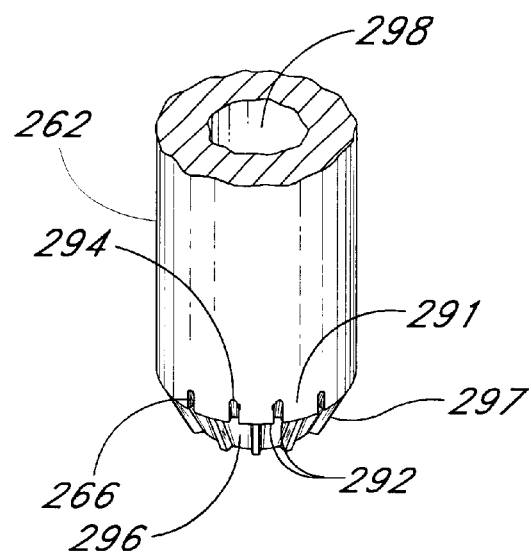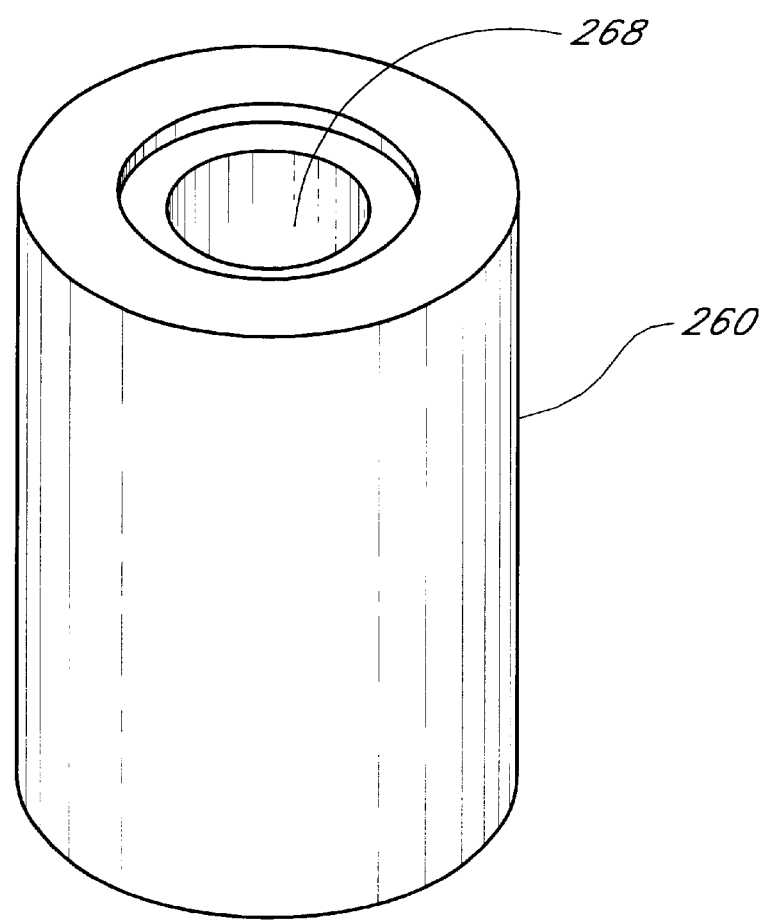
FIG. 26

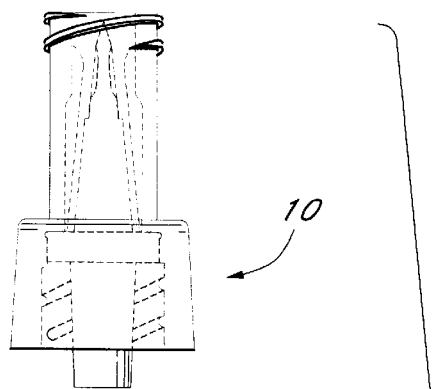
FIG. 36
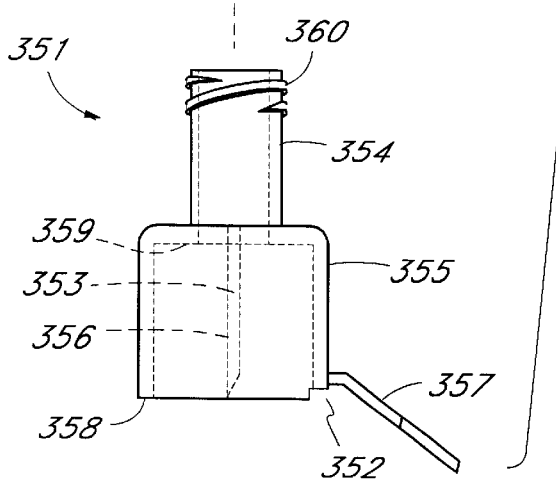
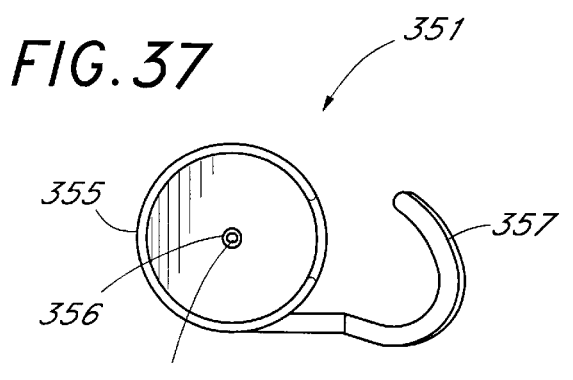
FIG. 37
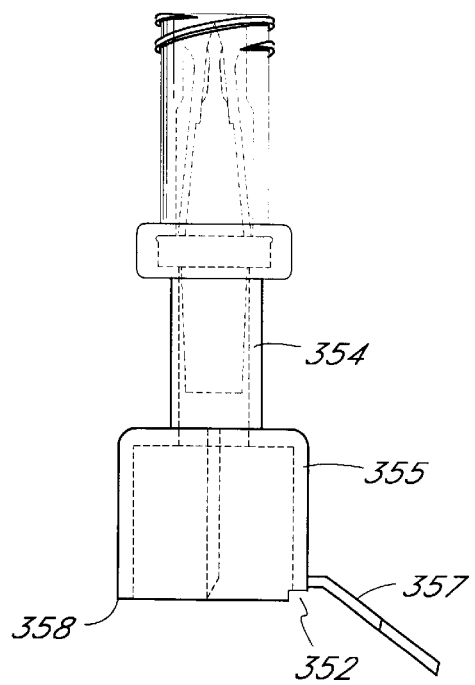
FIG. 38

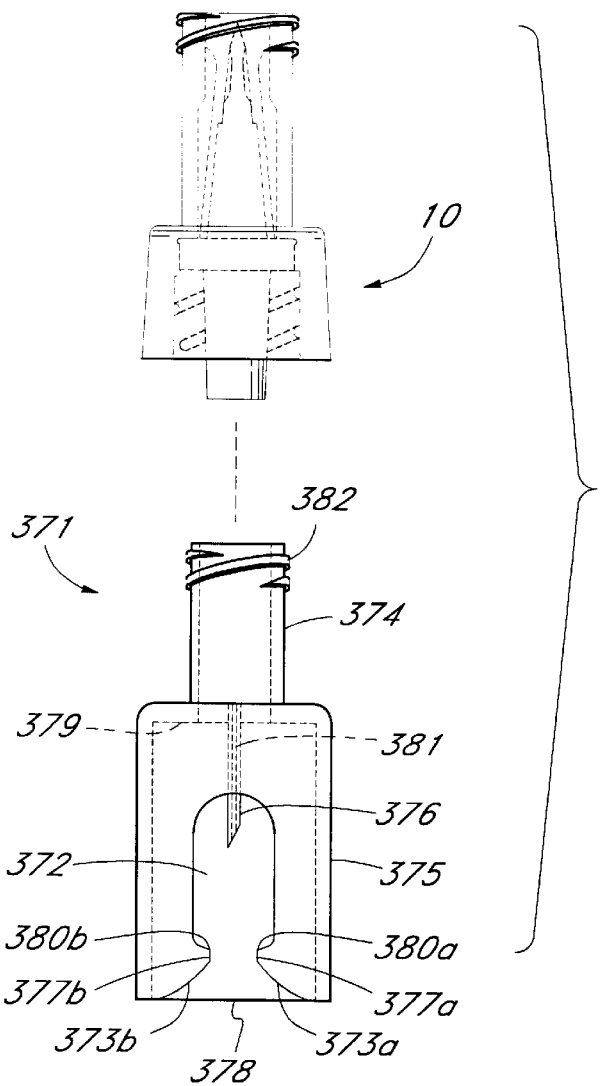
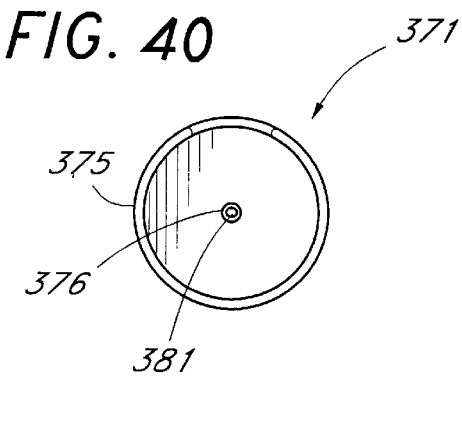
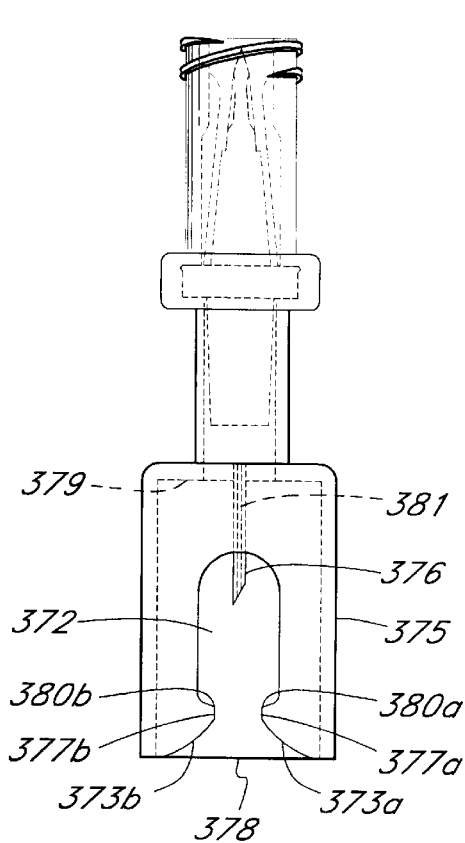
FIG. 39
FIG. 40
FIG. 41

FLUID TRANSFER DEVICE AND METHOD OF USE

PRIOR APPLICATION

This application is a continuation of prior application Ser. No. 09/150,580 filed Sep. 10, 1998 now abandoned; which is a continuation of application Ser. No. 08/476,127 filed Jun. 7, 1995 now abandoned; which is a continuation of application Ser. No. 08/265,095 filed Jun. 24, 1994 now abandoned, which is a continuation in part of application Ser. No. 08/096,659 filed Jul. 23, 1993 now U.S. Pat. No. 5,695,466; which is a continuation in part of PCT/US92/10367 filed Dec. 1, 1992; which is a continuation in part of application Ser. No. 07/813,073 filed Dec. 18, 1991 now abandoned. The disclosures of these related applications are incorporated herein in their entirety by this reference thereto.

BACKGROUND OF THE INVENTION

1. Field of the Invention

This invention relates to a device for transferring medication or another fluid from one location to another. This device eliminates the need for handling needles by medical personnel during the administration of medication.

2. Background Discussion

The manipulation of fluids for parenteral administration in hospital and medical settings routinely involves the use of syringes to facilitate the movement of a fluid between two points. Many syringes have needles attached which are used to pierce the seal or septum of a medicament container, or a septum in fluid communication with sterile tubing. Fluid then passes from the container or tubing into the syringe and is transferred from the syringe to an installed intravenous line (IV) or other fluid delivery system. Additionally, needles are often used to transfer fluids from one fluid line to another.

In some instances, the fluid is withdrawn from a single-dose medication container and injected into an IV system, supplementing the fluid already being administered through the IV line. These single-dose medication containers are then typically discarded. Commonly, these single-dose medication containers are "drip bags" for intravascular use, or vials bottles, or test tubes.

Intravenous tubing sets also commonly incorporate "y-connectors" having a septum which, when penetrated, allows access to the fluid flowing within the tubing set. Syringes are often used to penetrate the septums and add or withdraw fluid from the tubing set.

The sharp needles employed with conventional syringes used to draw or introduce fluid from containers or tubing sets introduce the risk of puncture wounds to the user or patient, with a concurrent risk of exposure to a direct dose of medication which can be, in extreme instances, fatal.

A medication transfer system that is easy to use and eliminates the threat posed by exposed needles would therefore be of great benefit to the medical community.

SUMMARY OF THE INVENTION

One embodiment of the present invention is a medication transfer device which eliminates the risk of accidental needle sticks during the handling of fluid-filled syringes having attached needles. As will be discussed in detail below, the device assists in the transfer of fluid from a sealed container to a syringe or vice versa.

The present invention comprises a piercing device used to access fluid in the interior of a vial through a pierceable seal located at the top of the vial, and facilitate the transfer of the fluid into a syringe. The device comprises a piercing element, having a hollow tube with an exterior surface, an interior bore, and at least one hole in the piercing element through which fluid flows into the interior bore of the piercing element. The device also comprises a locking structure projecting outward from the exterior surface of the piercing element. This locking structure permits penetration of the pierceable seal by the piercing element, but prohibits withdrawal of the piercing element back through the pierceable seal. A connecting portion adapted to connect the device to a syringe allows fluid from the interior of the vial to pass through the device and into the syringe. In a preferred embodiment, the device also comprises a stop which limits the extent of penetration of the piercing element into the interior of the vial. This stop may be a round disk, or a tab, located on the piercing element. Preferably, the locking structure is at least one barb, which extends at an angle away from the piercing element. The connecting portion preferably forms a substantially fluid-tight seal with the syringe.

In accordance with another aspect of the present invention, a method of accessing and transferring fluid inside a vial through a pierceable seal on the vial, using a syringe, is provided. The method comprises the steps of connecting the syringe to a device having a piercing element. This piercing element has a hollow tube having an exterior surface, an interior bore, a distal end and at least one hole proximal to the distal end. The piercing element also includes a locking structure projecting outward from the exterior surface of the piercing element. This locking structure permits penetration of the pierceable seal by the piercing element, but prohibits withdrawal of the piercing element back through the pierceable seal. The piercing element is used to pierce the seal on the vial, and is inserted into the vial until the hole proximal the distal end of the piercing element contacts the fluid inside the vial. The desired amount of fluid is withdrawn from the vial through the internal bore in the piercing element and into the syringe. The syringe is then separated from the piercing element, such that the locking structure on the piercing element prohibits the withdrawal of the piercing element through the pierceable seal. In a preferred embodiment, the syringe and the piercing element are connected before the piercing element is inserted into the vial. Alternatively, the piercing element can be inserted into the vial prior to connecting it to the syringe. The method of the present invention further comprises connecting a second syringe to the piercing element which remains in the vial, and repeating the withdrawing and separating steps to fill the second syringe. In a preferred embodiment, the syringe forms a substantially fluid-tight seal with the piercing element.

In yet another embodiment of the present invention, the piercing device is used in conjunction with a medical valve to provide a resealable fluid pathway between a vial and a syringe. In accordance with this embodiment, the valve preferably comprises a hollow housing having a spike with a seal mounted thereon located within the housing. A first end of the housing allows a syringe or other medical implement to access the seal, which may be pressed over the spike to allow fluid flow therethrough. A second end of the housing allows access to the end of said spike opposite said seal. Threads are preferably located within the second end of the housing for securing a medical connector to the free end of the spike.

In operation the piercing device described above is pressed through a seal on a vial. The connecting end of the piercing element is then connected to the free end of the spike. Threads are preferably located on the outside of the connecting end of the piercing element for locking engagement with the threads located on the housing.

A syringe may then be pressed against the seal on the other end of the valve. At that time fluid may be withdrawn from the vial through the piercing element and valve and into the syringe. This system advantageously allows disconnection of the syringe from the valve, at which time the seal reseals the spike of the medical valve, thereby sealing the passage to the vial and protecting the integrity of the fluid therein.

Another aspect of this invention is an adaptor for use with medicament containers such as a drip bag. The adaptor has a medical valve as described above, which may be removably attached by a locking mechanism to a second tubular body having a tubular spike. The spike is in fluid communication with the medicament container. Alternatively, the second body and valve may be formed integrally. In use, the valve is attached to the medicament container and then the tip of an ANSI standard connector, such as an IV set or syringe, is pressed into the valve, depressing the seal and exposing the spike within the valve. The large tubular spike on the second body is then used to penetrate the seal or septum of the medicament container, and fluid is withdrawn through the valve. The aspect of this invention related to an adaptor for use with medicament containers also relates to the following embodiments:

A medical valve adaptor for use with containers of fluid, said valve adaptor comprising:
  a first body having proximal and distal ends, and a cavity therein;
  a first spike located within said cavity and attached to said proximal end;
  a seal located on said first spike;
  one or more tabs connected to said first body and extending from said first body into said cavity and against said first spike to lock said first pike and seal within the cavity in said first body;
  a tubular second body having proximal and distal ends;
  a tubular second spike located on the distal end of said second body and in fluid communication therewith; and
  the proximal end of said first body located integrally on the proximal end of said second body, and in fluid communication therewith.

A method of assembling a medical valve adaptor for use with containers of fluid, said valve adaptor including a first body having proximal and distal ends and a cavity therein, a first spike, a resilient seal, a second tubular body having proximal and distal ends, and a second tubular spike, said method comprising the steps of:
  placing said seal over an end of said first spike;
  attaching said first spike, with said seal thereon, inside said cavity to the proximal end of said first body;
  creating at least one tab for securing said first spike with said seal thereon within said cavity in said first body;
  forming said second spike integrally with the distal end of said second body; and
  creating a locking mechanism integrally with the proximal end of said second body, said locking mechanism adapted to secure the proximal end of said first body to, and in fluid communication with, the proximal end of said second body.

A method of assembling a medical valve adaptor for use with a container of fluid, said valve adaptor including a first body having proximal and distal ends and a cavity therein, a first spike, a resilient seal, a second tubular body having proximal and distal ends, and a second tubular spike, said method comprising the steps of:
  a placing said seal over an end of said first spike;
  attaching said first spike, with said seal thereon, inside said cavity to the proximal end of said first body;
  creating at least one tab for securing said first spike with said seal thereon within said cavity in said first body;
  forming said second spike integrally with the distal end of said second body; and
  joining the proximal end of said first body to, and in fluid communication with, the proximal end of said second body.

A method of using a medical valve adaptor for use with a container of fluid and a fluid withdrawal device having a tip and an ANSI standard connector located on said tip, said valve adaptor including a first body, and a tubular second body separate from said first body, said first body having proximal and distal ends and comprising:
  a cavity located therein;
    a first spike located within said cavity and attached to said proximal end;
    a seal located on said first spike; and
    one or more tabs connected to said first body and extending from said first body into said cavity and against said first spike to lock said first spike and seal within the cavity in said first body;
said second body having proximal and distal ends and comprising:
  a tubular second spike located on the distal end of said second body and in fluid communication therewith; and
  a locking mechanism located on the proximal end of said second body, said locking mechanism adapted to secure the proximal end of said first body to, and in fluid communication with, the proximal end of said second body;
and method comprising the steps of:
  attaching said first body to said second body using said locking mechanism;
  inserting the tip of said fluid withdrawal device into the distal end of said first body, depressing said seal to expose said first spike; and
  inserting said second spike into said container.

A method of using a medical valve adaptor for use with a container of fluid and a fluid withdrawal device having a tip and an ANSI standard connector located on said tip, said valve adaptor including a first body, and a tubular second body integral to and in fluid communication with said first body, said first body having proximal and distal ends and comprising:
  a cavity located therein;
    a first spike located within said cavity and attached to said proximal end;
    a seal located on said first spike; and
    one or more tabs connected to said first body and extending from said first body into said cavity and against said first spike to lock said first spike and seal within the cavity in said first body;
said second body having proximal and distal ends and comprising a tubular second spike located on the distal end of said second body and in fluid communication therewith, said method comprising the steps of:
  inserting the tip of said fluid withdrawal device into the distal end of said first body, depressing said seal to expose said first spike; and inserting said second spike into said container.

Another aspect of this invention is a three-way valved "y-connector" for use with medicament containers. The y-connector comprises the valve described above, which may be removably attached by a locking mechanism to a second tubular body having a tubular branch port which projects at an angle to the main body, and is in fluid communication with the main body. Alternatively, the second body and spike of the valve may be formed integrally. In use, the valve is attached to the second body and then the tip of an ANSI standard connector, such as an IV set or syringe, is pressed into the valve, depressing the seal and exposing the through holes of the spike within the valve. Fluid may then be introduced or withdrawn from the y-connector through the valve. The aspect of the invention related to a three-way valved "y-connector" for use with medicament containers also relates to the following embodiments:

A medical three-way valved connector for use with containers of fluid, said valve connector comprising:
  a first body having proximal and distal ends, and a cavity therein;
  a spike located within said cavity and attached to the proximal end of said first body;
  a seal located on said spike;
  one or more tabs connected to said first body and extending from said first body into said cavity and against said spike to lock said spike and seal within the cavity in said first body;
  a tubular second body having proximal and distal ends;
  a tubular branch located at an angle to, and toward the proximal end of, said second body, and in fluid communication therewith; and
  the proximal end of said first body located integrally on the proximal end of said second body, and in fluid communication therewith.

A method of assembling a medical three-way valved connector, said valved connector including a first body having proximal and distal ends and a cavity therein, a spike, a resilient seal, a second tubular body having proximal and distal ends, and a tubular branch, said method comprising the steps of:
  placing said seal over an end of said spike;
  attaching said spike, with said seal thereon, inside said cavity to the proximal end of said first body;
  creating at least one tab for securing said spike with said seal thereon within said cavity in said first body;
  forming said tubular branch integrally with said second body and in fluid communication therewith; and
  creating a locking mechanism integrally with the proximal end of said second body, said locking mechanism adapted to secure the proximal end of said first body to, and in fluid communication with, the proximal end of said second body.

A method of assembling a medical three-way valved connector, said valve connector including a first body having proximal and distal ends and a cavity therein, a spike, a resilient seal, a second tubular body having proximal and distal ends, and a tubular branch, said method comprising the steps of:
  placing said seal over an end of said spike;
  attaching said spike, with said seal thereon, inside said cavity to the proximal end of said first body;
  creating at least one tab for securing said spike with said seal thereon within said cavity in said first body;
  forming said tubular branch integrally with said second body and in fluid communication therewith; and
  joining the proximal end of said first body to, and in fluid communication with, the proximal end of said second body.

A method of using medical three-way valved connector and a fluid withdrawal device having a tip and an ANSI standard connector located on said tip, said valve connector having a first body and a tubular second body separate from said first body, said first body having proximal and distal ends and comprising:
  a cavity located therein;
  a spike located within said cavity and attached to said proximal end of said first body;
  a seal located on said spike; and
  one or more tabs connected to said first body and extending from said first body into said cavity and against said spike to lock said spike and seal within the cavity in said first body;
said second body having proximal and distal ends and comprising:
  a tubular branch located at an angle to, and toward the proximal end of, said second body, and in fluid communication therewith; and
  a locking mechanism located on the proximal end of said second body, said locking mechanism adapted to secure the proximal end of said first body to, and in fluid communication with, the proximal end of said second body;
said method comprising the steps of:
  attaching said first body to said second body using said locking mechanism; and
  inserting the tip of said fluid withdrawal device into the distal end of said first body, depressing said seal to expose said first spike.

A method of using a medical three-way valved connector and a fluid withdrawal device having a tip and an ANSI standard connector located on said tip, said valved connector having a first body and a tubular second body integral to and in fluid communication with said first body, said first body having proximal and distal ends and comprising:
  a cavity located therein;
  a spike located within said cavity and attached to said proximal end of said first body;
  a seal located on said spike; and
  one or more tabs connected to said first body and extending from said first body into said cavity and against said spike to lock said spike and seal within the cavity in said first body;
said second body having proximal and distal ends and having a tubular branch located at an angle to, and toward the proximal end of, said second body, and in fluid communication therewith, said method comprising the step of inserting the tip of said fluid withdrawal device into the distal end of said first body, depressing said seal to expose said first spike.

Another aspect of the present invention is an adaptor for use with a standard piggyback or y-site connector. The adaptor comprises the medical valve described above, which may be removably attached by a locking mechanism to a second body which may have a cylindrical housing and a tubular spike located, at least partially, within the housing. The second body also has a hook, which is adapted to engage the y-site, releasably locking the adaptor to the connector. The valve is in fluid communication with the second body.

In an alternative embodiment, the second body and valve may be formed integrally. In use, the valve is attached to second body. The adaptor is then placed in fluid communication and releasably locked to the y-site or piggyback connector. Thereafter, the tip of an ANSI standard connector, such as an IV set or syringe, is pressed into the valve, depressing the seal and exposing the through holes of the spike within the valve. Fluid may then be introduced or withdrawn through the adaptor to the piggyback connector. This aspect of the invention also relates to the following embodiments.

A medical valve adaptor for use with medical three-way fluid connectors, said valve adaptor comprising:

a first body having proximal and distal ends, and a cavity therein;

a first spike located within said cavity and attached to the proximal end of said first body;

a seal located on said first spike;

one or more tabs connected to said first body and extending from said first body into said cavity and against said first spike to lock said first spike and seal within the cavity in said first body;

a tubular second body having proximal and distal ends;

a cylindrical housing adapted to surround the end of said three-way connector and located on the distal end of said second body;

a tubular second spike located on the distal end of said second body and within said housing, and in fluid communication with said second body;

a hook located on said housing and adapted to engage said three-way connector such that said valved adaptor is secured to said three-way connector; and and proximal end of said first body integrally located on the proximal end of said second body, and in fluid communication therewith.

A method of assembling a medical valve adaptor, said valve adaptor including a first body having proximal and distal ends and a cavity therein, a first spike, a resilient seal, a second tubular body having proximal and distal ends, a second tubular spike, a cylindrical housing, and a hook, said method comprising the steps of:

placing said seal over an end of said first spike;

attaching said first spike, with said seal thereon, inside said cavity to the proximal end of said first body;

creating at least one tab for securing said first spike with said seal thereon with said cavity in said first body;

forming said housing integrally with the distal end of said second body;

forming said second spike integrally with the distal end of said second body and located within said housing, said second spike being in fluid communication with said second body; and creating a locking mechanism integrally with the proximal end of said second body, said locking mechanism adapted to secure the proximal end of said first body to, and in fluid communication with, the proximal end of said second body.

A method of assembling a medical valve adaptor, said valve adaptor including a first body having proximal and distal ends and a cavity therein, a first spike, a resilient seal, a second tubular body having proximal and distal ends, a second tubular spike, a cylindrical housing, and a hook, said method comprising the steps of:

a placing said seal over an end of said first spike;

attaching said first spike, with said seal thereon, inside said cavity to the proximal end of said first body;

creating at least one tab for securing said first spike with said seal thereon within said cavity in said first body;

forming said housing integrally with the distal end of said second body;

forming said second spike integrally with the distal end of said second body and located within said housing, said second spike being in fluid communication with said second body; and joining the proximal end of said first body to, and in fluid communication with, the proximal end of said second body.

A method of using a medical valve adaptor for use with medical three-way fluid connectors and a fluid withdrawal device having a tip and an ANSI standard connector located on said tip, said valve adaptor having a first body and a tubular second body separate from said first body, said first body having proximal and distal ends and comprising:

a cavity located therein;

a spike located within said cavity and attached to said proximal end of said first body;

a seal located on said spike; and one or more tabs connected to said first body and extending from said first body into said cavity and against said spike to lock said spike and seal within the cavity in said first body;

said second body having proximal and distal ends and comprising:

a tubular second body having proximal and distal ends;

a cylindrical housing adapted to surround the end of said three-way connector and located on the distal end of said second body;

a tubular second spike located on the distal end of said second body and within said housing, and in fluid communication with said second body;

a hook located on said housing and adapted to engage said three-way connector such that said valved adaptor is secured to said three-way connector; and a locking mechanism located on the proximal end of said second body, said locking mechanism adapted to secure the proximal end of said first body to, and in fluid communication with, the proximal end of said second body;

said method comprising the steps of:

attaching said first body to said second body using said locking mechanism;

attaching said second body to said three-way connector by surrounding the end of said three-way connector with said housing and engaging said three-way connector with said hook; and inserting the tip of said fluid withdrawal device into the distal end of said first body, depressing said seal to expose said first spike.

A method of using a medical valve adaptor for use with medical three-way fluid connectors and a fluid withdrawal device having a tip and an ANSI standard connector located on said tip, said valve adaptor having a first body and a tubular second body integral to and in fluid communication with said first body, said first body having proximal and distal ends and comprising:

a cavity located therein;

a spike located within said cavity and attached to said proximal end of said first body;

a seal located on said spike; and one or more tabs connected to said first body and extending from said first body into said cavity and against said spike to lock said spike and seal within the cavity in said first body;

said second body having proximal and distal ends and comprising:

a tubular second body having proximal and distal ends;

a cylindrical housing adapted to surround the end of said three-way connector and located on the distal end of said second body;

a tubular second spike located on the distal end of said second body and within said housing, and in fluid communication with said second body; and a hook located on said housing and adapted to engage said three-way connector such that said valved adaptor is secured to said three-way connector;

said method comprising the steps of:

attaching said second body to said three-way connector by surrounding the end of said three-way connector with said housing and engaging said three-way connector with said hook; and inserting the tip of said fluid withdrawal device into the distal end of said first body, depressing said seal to expose said first spike.

This invention also comprises another adaptor for use with standard medical three-way y-connectors. The adaptor comprises the medical valve described above, which may be removably attached by a locking mechanism to a second tubular body having a cylindrical housing and a spike located within the housing. The spike is in fluid communication with the second body. The second body also has an opening in a side wall thereof having one or more tabs. The opening is adapted to engage an arm of a standard y-connector, such that the arm "snaps" past the tabs into the opening in the side wall, releasably locking the adaptor to the connector. In an alternative embodiment, the second body and valve may be formed integrally with one another. In use, the valve is attached to the second body and then the tip of an ANSI standard connector, such as an IV set or syringe, is pressed into the valve, depressing the seal and exposing the spike within the valve. The tubular spike on the second body is then used to penetrate the seal or septum of the y-connector. When the second body is pressed onto the y-connector, the opening and tabs surround an arm of the piggyback connector. The arm "snaps" past the tabs, which holds the adaptor in place, releasably locking the adaptor to the connector. Fluid is then introduced or withdrawn through the adaptor. This other adaptor also relates to the following embodiments:

A medical valve adaptor for use with medical three-way fluid connectors, said valve adaptor comprising:

a first body having proximal and distal ends, and a cavity therein;

a first spike located within said cavity and attached to the proximal end of said first body;

a seal located on said first spike;

one or more tabs connected to said first body and extending from said first body into said cavity and against said first spike to lock said first spike and seal within the cavity in said first body;

a tubular second body having proximal and distal ends;

a cylindrical housing adapted to surround the end of said three-way connector and located on the distal end of said second body;

a tubular second spike located on the distal end of said second body and within said housing, and in fluid communication with said second body;

an opening having one or more tabs, said opening located on said housing and adapted to engage said three-way connector such that said valved adaptor is secured to said three-way connector and partially held in place by said tabs; and the proximal end of said first body integrally located on the proximal end of said second body, and in fluid communication therewith.

A method of assembling a medical valve adaptor, said valve adaptor including a first body having proximal and distal ends and a cavity therein, a first spike, a resilient seal, a second tubular body having proximal and distal ends, a second tubular spike, and a cylindrical housing having an opening with one or more tabs, said method comprising the steps of:

placing said seal over an end of said first spike;

attaching said first spike, with said seal thereon, inside said cavity to the proximal end of said first body;

creating at least one tab for securing said first spike with said seal thereon within said cavity in said first body;

forming said housing integrally with the distal end of said second body;

forming said second spike integrally with the distal end of said second body and located within said housing, said second spike being in fluid communication with said second body; and creating a locking mechanism integrally with the proximal end of said second body, said locking mechanism adapted to secure the proximal end of said first body to, and in fluid communication with, the proximal end of said second body.

A method of assembling a medical valve adaptor, said valve adaptor including a first body having proximal and distal ends and a cavity therein, a first spike, a resilient seal, a second tubular body having proximal and distal ends, a second tubular spike, and a cylindical housing having an opening with one or more tabs, said method comprising the steps of:

placing said seal over an end of said first spike;

attaching said first spike, with said seal thereon, inside said cavity to the proximal end of said first body;

creating at least one tab for securing said first spike with said seal thereon within said cavity in said first body;

forming said housing integrally with the distal end of said second body;

forming said second spike integrally with the distal end of said second body and located within said housing, said second spike being in fluid communication with said second body; and joining the proximal end of said first body to, and in fluid communication with, the proximal end of said second body.

A method of using a medical valve adaptor for use with medical three-way fluid connectors and a fluid withdrawal device having a tip and an ANSI standard connector located on said tip, said valve adaptor having a first body and a tubular second body separate from said first body, said first body having proximal and distal ends and comprising:

a cavity located therein;

a spike located within said cavity and attached to said proximal end of said first body;

a seal located on said spike; and
one or more tabs connected to said first body and extending from said first body into said cavity and against said spike to lock said spike and seal within the cavity in said first body;
said second body having proximal and distal ends and comprising:
a tubular second body having proximal and distal ends;
a cylindrical housing adapted to surround the end of said three-way connector and located on the distal end of said second body;
a tubular second spike located on the distal end of said second body and within said housing, and in fluid communication with said second body;
an opening having one or more tabs, said opening located on said housing and adapted to engage said three-way connector such that said valved adaptor is secured to said three-way connector and partially held in place by said tabs; and
a locking mechanism located on the proximal end of said second body, said locking mechanism adapted to secure the proximal end of said first body to, and in fluid communication with, the proximal end of said second body;
said method comprising the steps of:
attaching said first body to said second body using said locking mechanism;
attaching said second body to said three-way connector by surrounding the end of said three-way connector with said housing and engaging said three-way connector with said opening and tabs; and
inserting the tip of said fluid withdrawal device into the distal end of said first body, depressing said seal to expose said first spike.

A method of using a medical valve adaptor for use with medical three-way fluid connectors and a fluid withdrawal device having a tip and an ANSI standard connector located on said tip, said valve adaptor having a first body and a tubular second body integral to and in fluid communication with said first body, said first body having proximal and distal ends and comprising:
a cavity located therein;
a spike located within said cavity and attached to said proximal end of said first body;
a seal located on said spike; and
one or more tabs connected to said first body and extending from said first body into said cavity and against said spike to lock said spike and seal within the cavity in said first body;
said second body having proximal and distal ends and comprising:
a tubular second body having proximal and distal ends;
a cylindrical housing adapted to surround the end of said three-way connector and located on the distal end of said second body;
a tubular second spike located on the distal end of said second body and within said housing, and in fluid communication with said second body; and
an opening having one or more tabs, said opening located on said housing and adapted to engage said three-way connector such that said valved adaptor is secured to said three-way connector and partially held in place by said tabs;
said method comprising the steps of:

attaching said second body to said three-way connector by surrounding the end of said three-way connector with said housing and engaging said three-way connector with said opening and tabs; and
inserting the tip of said fluid withdrawal device into the distal end of said first body, depressing said seal to expose said first spike.

Still another aspect of this invention is an adaptor for use with narrowly necked medicament containers such as test tubes. The adaptor comprises the medical valve described above, which may be removably attached by a locking mechanism to a second tubular body having an open-ended tube. The open-ended tube is in fluid communication with the second body. Alternatively, the second body and valve may be formed integrally with one another. In use, the valve is attached to the second body and then the tip of an ANSI standard connector, such as an IV set or syringe, is pressed into the valve, depressing the seal and exposing the spike within the valve. The open-ended tube on the second body is then inserted into the narrowly necked container, and fluid is withdrawn through the adaptor. This aspect of the invention also relates to the following embodiments:

A medical valve adaptor for use with medical three-way fluid connectors, said valve adaptor comprising:
a first body having proximal and distal ends, and a cavity therein;
a first spike located within said cavity and attached to the proximal end of said first body;
a seal located on said first spike;
one or more tabs connected to said first body and extending from said first body into said cavity and against said first spike to lock said first spike and seal within the cavity in said first body;
a tubular second body having proximal and distal ends;
an open-ended tube adapted to reach into and withdraw fluids from said narrowly necked container, said tube located on the distal end of and in fluid communication with said second body; and
the proximal end of said first body integrally located on the proximal end of said second body, and in fluid communication therewith.

A method of assembling a medical valve adaptor, said valve adaptor including a first body having proximal and distal ends and a cavity therein, a first spike, a resilient seal, a second tubular body having proximal and distal ends, and an open-ended tube, said method comprising the steps of:
placing said seal over an end of said first spike;
attaching said first spike, with said seal thereon, inside said cavity to the proximal end of said first body;
creating at least one tab for securing said first spike with said seal thereon within said cavity in said first body;
attaching said open-ended tube to, and in fluid communication with, the distal end of said second body; and
creating a locking mechanism integrally with the proximal end of said second body, said locking mechanism adapted to secure the proximal end of said first body to, and in fluid communication with, the proximal end of said second body.

A method of assembling a medical valve adaptor, said valve adaptor including a first body having proximal and distal ends and a cavity therein, a first spike, a resilient seal, a second tubular body having proximal and distal ends, and an open-ended tube, said method comprising the steps of:
placing said seal over an end of said first spike;
attaching said first spike, with said seal thereon, inside said cavity to the proximal end of said first body;

creating at least one tab for securing said first spike with said seal thereon within said cavity in said first body;

attaching said open-ended tube to, and in fluid communication with, the distal end of said second body; and joining the proximal end of said first body to, and in fluid communication with, the proximal end of said second body.

A method of using a medical valve adaptor for use with a narrowly necked container of fluid and a fluid withdrawal device having a tip and an ANSI standard connector located on said tip, said valve adaptor including a first body, and a tubular second body separate from said first body, said first body having proximal and distal ends and comprising:

a cavity located therein;
a first spike located within said cavity and attached to said proximal end;
a seal located on said first spike; and
one or more tabs connected to said first body and extending from said first body into said cavity and against said first spike to lock said first spike and seal within the cavity in said first body;

said second body having proximal and distal ends and comprising:

a tubular second body having proximal and distal ends;
an open-ended tube adapted to reach into and withdraw fluids from said narrowly necked container, said tube located on the distal end of and in fluid communication with said second body; and
a locking mechanism located on the proximal end of said second body, said locking mechanism adapted to secure the proximal end of said first body to, and in fluid communication with, the proximal end of said second body;

said method comprising the steps of:
attaching said first body to said second body using said locking mechanism;
inserting the tip of said fluid withdrawal device into the distal end of said first body, depressing said seal to expose said first spike; and
inserting said open-ended tube into said narrowly necked container.

A method of using a medical valve adaptor for use with a narrowly necked container of fluid and a fluid withdrawal device having a tip and an ANSI standard connector located on said tip, said valve adaptor including a first body, and a tubular second body integral to and in fluid communication with said first body, said first body having proximal and distal ends and comprising:

a cavity located therein;
a first spike located within said cavity and attached to said proximal end;
a seal located on said first spike; and
one or more tabs connected to said first body and extending from said first body into said cavity and against said first spike to lock said first spike and seal within the cavity in said first body;

said second body having proximal and distal ends and comprising:

a tubular second body having proximal and distal ends; and
an open-ended tube adapted to reach into and withdraw fluids from said narrowly necked container, said tube located on the distal end of and in fluid communication with said second body;

said method comprising the steps of:

inserting the tip of said fluid withdrawal device into the distal end of said first body, depressing said seal to expose said first spike; and inserting said open-ended tube into said narrowly necked container.

Alternatively, each of the adaptors discussed above may be used by first placing the adaptor in fluid communication with the piggyback connector or other container and thereafter depressing the seal in the valve with an ANSI standard connector such as an IV set or syringe in order to introduce or withdraw fluid through the adaptor.

BRIEF DESCRIPTION OF THE DRAWING

FIG. 26 is a perspective view of a gouging bit and a base which are preferably used in the second assembly method.

FIG. 36 is a partially exploded side view of a hook adaptor made in accordance with this invention.

FIG. 37 is a plan view of the hook adaptor shown in FIG. 36, as viewed from the bottom.

FIG. 38 is a side view of another embodiment of the hook adaptor, having an integral valve.

FIG. 39 is a partially exploded side view of a snap-on adaptor made in accordance with this invention.

FIG. 40 is a plan view of the snap-on adaptor shown in FIG. 39, as viewed from the bottom.

FIG. 41 is a side view of another embodiment of the snap-on adaptor, having an integral valve.

DETAILED DESCRIPTION OF THE PREFERRED EMBODIMENTS

Figure 1:
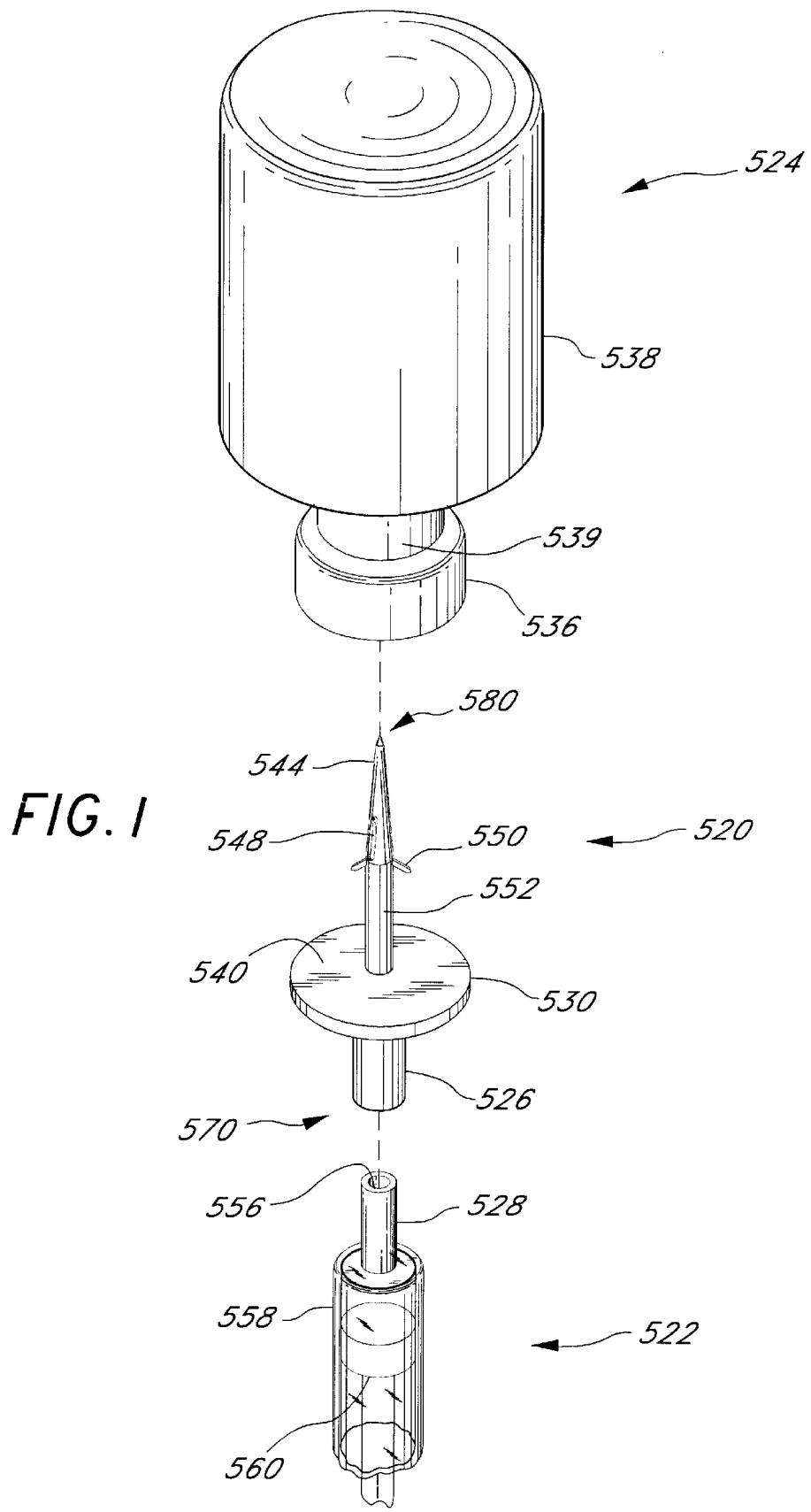
FIG. 1 is an exploded perspective view of a medication transfer device of the present invention in a typical orientation for drawing medication from a sealed vial.
Figure 2:
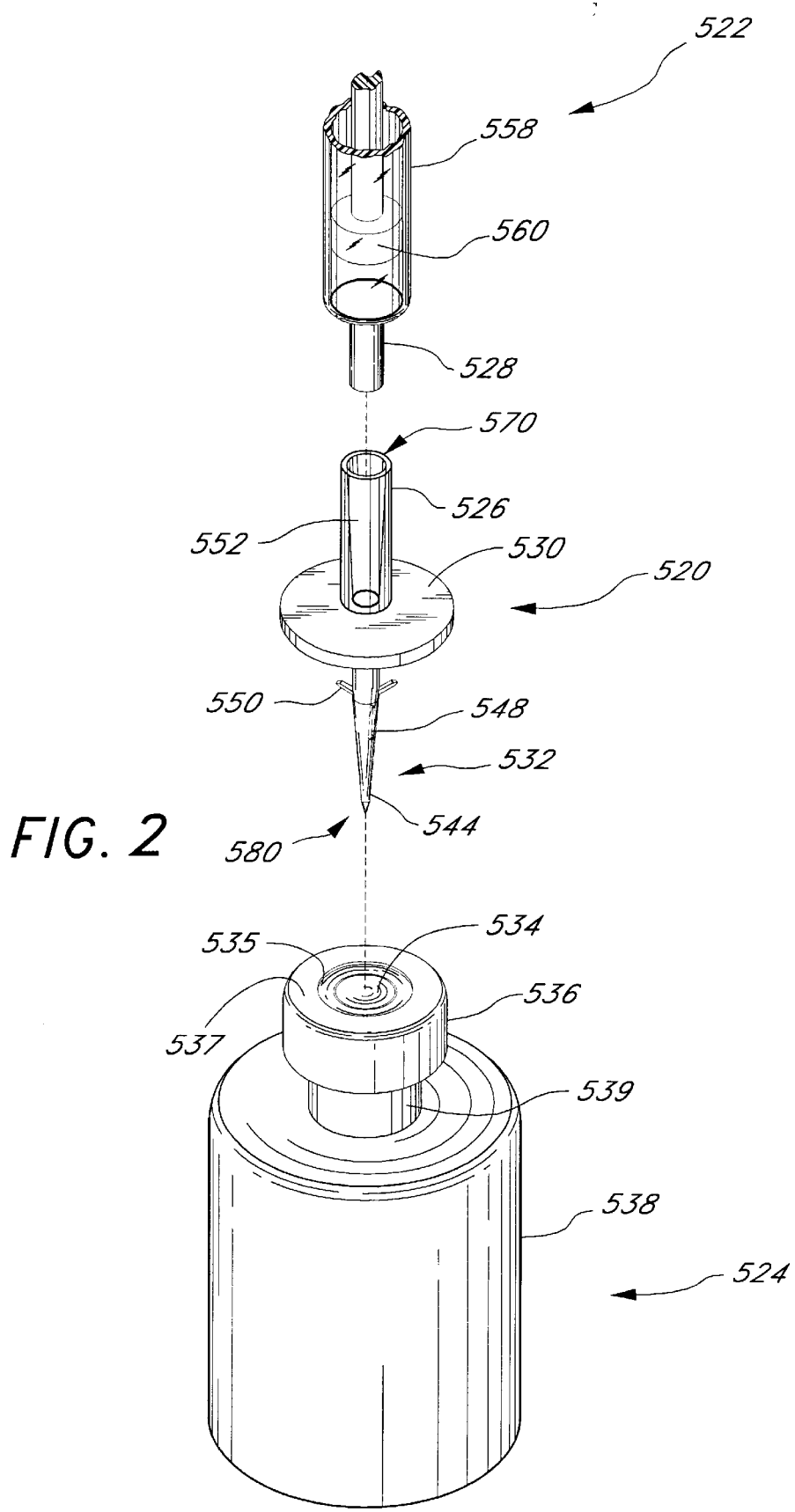
FIG. 2 is an exploded perspective view of the system of FIG. 1, inverted.

As shown in FIGS. 1 and 2, a first embodiment of the present invention generally comprises a piercing element 520 for use in a medication container access system. The system includes a standard medical implement used to measure and deliver a dose of fluid medication, such as a syringe 522, and a bottle or vial 524 containing the medication. Preferably, a single-dose vial suitable for disposal after one use is used, whereby the piercing element 520 may be disposable. FIGS. 1 and 2 are exploded views of the system, with FIG. 1 showing the typical orientation of the system when fluid is withdrawn from the vial 524. FIG. 2 shows an inverted orientation in order to better illustrate some of the elements of the present invention.

Fluid medication may be delivered to patients by drawing the medication from the vial 524 through the piercing element 520 into the syringe 522, and thereafter injecting the fluid from the syringe 522 into an existing IV delivery system. This method will be discussed in more detail below.

Preferably, the piercing element 520 has a proximal end 570 and a distal end 580. The proximal end 570 of the piercing element 520 preferably has a connecting portion which may be in the form of a tubular extension 526, adapted to receive the tip or nose 528 of an ANSI (American National Standards Institute, Washington, D.C.) standard syringe 522. It is, however, contemplated that the inner diameter of the tubular extension 526 can be of any size to accommodate the attachment of any of a number of medical implements. Once inserted into a bore 552 of the extension 526, the nose 528 of the syringe 522 forms a substantially fluid-tight fit with the extension 526. Preferably, bore 552 becomes slightly smaller in diameter from distal end 570 of extension 526 towards the proximal end 580 to accommodate a tapered nose 528 and form a tight seal. The taper of the bore 552 is preferably at the same angle as the nose 528 of the syringe 522 and, more preferably, in accordance with ANSI standards, the taper is 0.006 inch per linear inch. Although a fluid-tight seal is achieved, the tapered shape of these cooperating parts also allows them to be easily disengaged with a minimal separation force.

The medication vial 524 generally comprises a container portion 538 having a narrow neck 529 on which a cap or lid 536 fits. A resilient septum 534 is placed over a circular opening 535 in the lid 536 to simultaneously provide a seal for the vial 524 and an access site for the piercing element 520. The septum is prepared from a resilient material that is flexible, inert, impermeable to fluid and readily pierceable by the piercing element 520.

Referring now to FIG. 2, the piercing element 520 preferably has, at its distal end 580, a penetration portion 532. The penetration portion 532 preferably is sized so as to be able to pierce the septum 534 of the vial 524 and extend into contact with the medication within the container 538. A fluid flow conduit in the form of bore 552 runs from at least one hole 548 in the piercing element 520, through to the proximal end 570 of the side wall of the piercing element 520. In a preferred embodiment, the penetration portion 532 of the piercing element 520 has a tapered conical tip 544. Preferably, the distal end of the tip 544 is shaped to allow the tip 544 to pierce the septum 534 of the vial 524 and, therefore, the penetration portion 532 is sharply pointed. However, the penetration portion 532 may be slightly round to prevent accidental sticks and yet still be able to penetrate the septum 534.

As described above, preferably at least one longitudinal through hole 548 is provided proximal the distal end 580 of the piercing element 520 to permit fluid to flow from the container 524 into the bore 552. Advantageously, by placing the through hole 548 proximal the distal end 580 of the piercing element 520, the risk of coring the septum 534 with the piercing element 520 is eliminated. If the through hole 548 were to be located at the distal end 580 of the piercing element 520, the piercing element 520 may core the septum 534 introducing particulates into the fluid which may harm a patient. In a preferred embodiment, there are three through-holes 548 within about 0.200 inch from the distal end 580 of he piercing element 520. These through-holes 548 may be of any size; however, the larger the size of the through-holes, the greater the fluid flow rate through the bore 552 of the piercing element 520. In a preferred embodiment, the size of the through-holes 548 are 18-gauge or equivalent to provide a flow rate three times that of a standard 18-gauge needle.

In a preferred embodiment, a disk-shaped stop 530 centrally located on the piercing element 520 is integral with, and interconnects, the extension 526 and the penetrating portion 532 of the piercing element 520. A distal face 540 on the disk-shaped stop 530 may contact a top surface 537 of the cap 536 of the vial 524 to limit the distance the piercing element 520 may extend into the vial 524. The stop 530 may, of course, have a variety of shapes and configurations.

A locking structure 550 is preferably attached to or integral with the piercing element 520. In one embodiment, the locking structure 550 may comprise two barbs on diametrically opposed sides of the piercing element 520 near the distal end 580. The barbs are desirably angled in the proximal direction in order to more easily pass through the elastomeric septum 534 into the vial 524. The barbs prevent the removal of the penetration portion 544 of the piercing element 520 back through the septum 534. The locking structure 550 thus retains a portion of the piercing element 520 in the vial 524. In one embodiment, the piercing element 520 is approximately 0.125 inch in diameter and the locking structure 550 extends at a 45° angle towards the proximal end a distance of approximately 0.0625 inch.

It is possible for the locking structure 550 to be located other than at the distal end 580 of the piercing element. For example, the locking element may comprise a somewhat elongate barbed structure, which extends from the piercing element 520 some distance form the distal end 580. Alternatively, the locking structure 550 may extend from the stop 530 of the piercing element, depending on its location. For example, one or more barb-like structures may extend downwardly from the stop 530 along a side of the piercing element 520.

Method of Using the Vial Access Device

The vial access device of the present invention provides a closed system for transferring a predetermined amount of medication from a remote source to a patient. Referring to FIGS. 1 and 2, the delivery end or nose 528 of a medical implement such as a syringe is engaged with the piercing element 520. The nose 528 is pushed into the proximal end of bore 552 of the piercing element 520 until a substantially fluid-tight fit is achieved between the syringe 522 and the piercing element 520. The distal end 580 of the piercing element 520 is then inserted through the septum 534 of the medication vial 524. The vial 524 is generally held in an inverted position, as shown in FIG. 1, such that the fluid in the vial abuts the septum 534. The penetrating portion 544 of the piercing element 520 and the locking structure 550 are pushed through the septum 534, thereby exposing the through-hole(s) 548 to the fluid inside the vial 524. A plunger 560 inside the syringe 522 is withdrawn, thereby creating a vacuum which draws fluid from the vial 524, through the through hole(s) 548, the bore 552, a conduit 556 in the syringe nose 528 and into a chamber 558 in the syringe 522. The desired amount of medication is thus transferred from the vial 524, through the piercing element 520 and into the syringe 522.

After the desired amount of fluid has been fluid has been drawn into the syringe 522, the syringe 522 is pulled away from the vial 524. Upon retraction of the syringe 522 from the piercing element 520, the locking structure 550 catches on the inner side of the septum 534, preventing the piercing element 520 from disengaging the vial 524. Further refraction force causes the syringe nose 528 to disengage from the piercing element 520. The user than transfers the fluid within the syringe 522 to a delivery system which administers the medication to the patient.

Preferably, if fluid remains in the vial 524 after the desired volume of fluid is transferred to the syringe 522, the syringe 522 is withdrawn from the piercing element 520 as shown in FIG. 2 so that the fluid contained in the vial 524 does not spill. The vacuum created in the syringe 522 prevents the fluid medication from exiting the syringe 522 through the conduit 556 in the syringe nose 528.

The piercing element 520 is partially trapped in the vial 524 by the locking structure 550. The single-dose medication vial 524 and piercing element 520 may then be discarded as a unit. Advantageously, by not removing the penetration portion 544 of the piercing element 520 from the vial, the risk of a healthcare worker injuring himself or herself on the penetration portion 544 or locking structure 550 of the piercing element is eliminated. Alternatively, if the vial contains sufficient medication for more than a single dose, a new syringe can be attached to the piercing element 520 held within the medication vial 524 and additional fluid can be transferred from the vial 524, through the piercing element 520 and into the new syringe 522.

The piercing element 520 is preferably manufactured from a hard plastic. The piercing element 520 may also be manufactured from other medically inert materials known to those of skill in the art. One particular advantage of this invention is that it eliminates the use of metal needles. This dramatically reduces the risk of skin puncture during the administration of fluids contained in a vial to a patient. The piercing element 520 need only be strong enough to penetrate the septum 534 of a vial 524 or other similar seal.

Alternate Embodiment

Figure 32:
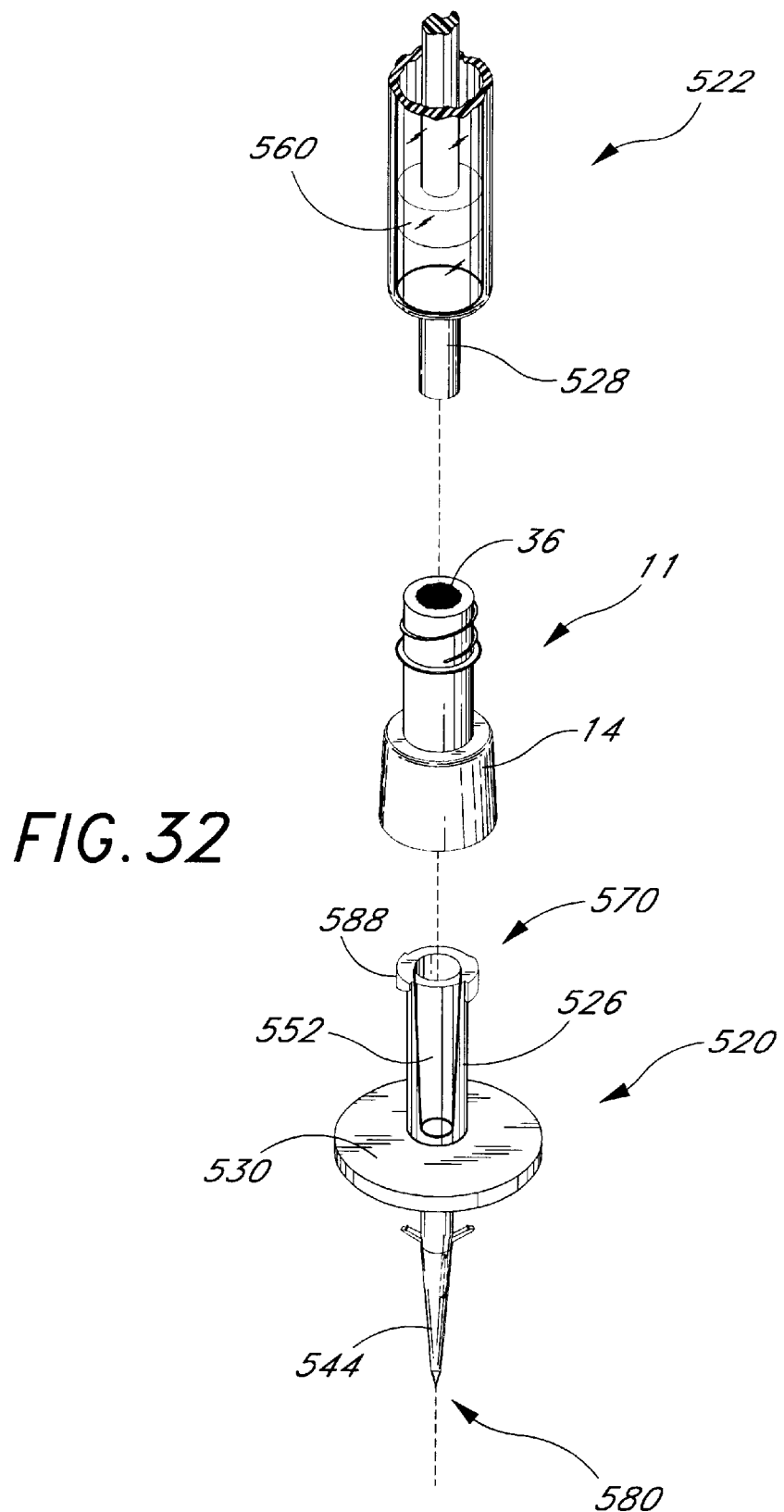
FIG. 32 is an exploded perspective view of a preferred medication transfer device utilized with a medical valve and syringe.

In a second embodiment as shown in FIG. 32 and described in more detail below, the piercing element 520 is used in conjunction with a medical valve 10 or 11 described below in order to transfer fluid from a vial 524 to a syringe 522.

FIGS. 3–31 illustrate the medical valve 10 or 11 and methods of manufacturing the valve 10 or 11. In this description and in conjunction with the FIGURES, the term "proximal" is used to denote the end of the valve and other components at or near the spike tip 32 in FIGS. 4 through 8, 10 through 12, 14, 16 and 25, and at or near the seal cap 92 in FIGS. 3, 9, 13, and 15 through 19. The term "distal" is used to denote the opposite end of the valve, or spike tip, or seal.

Figures 3, 4:
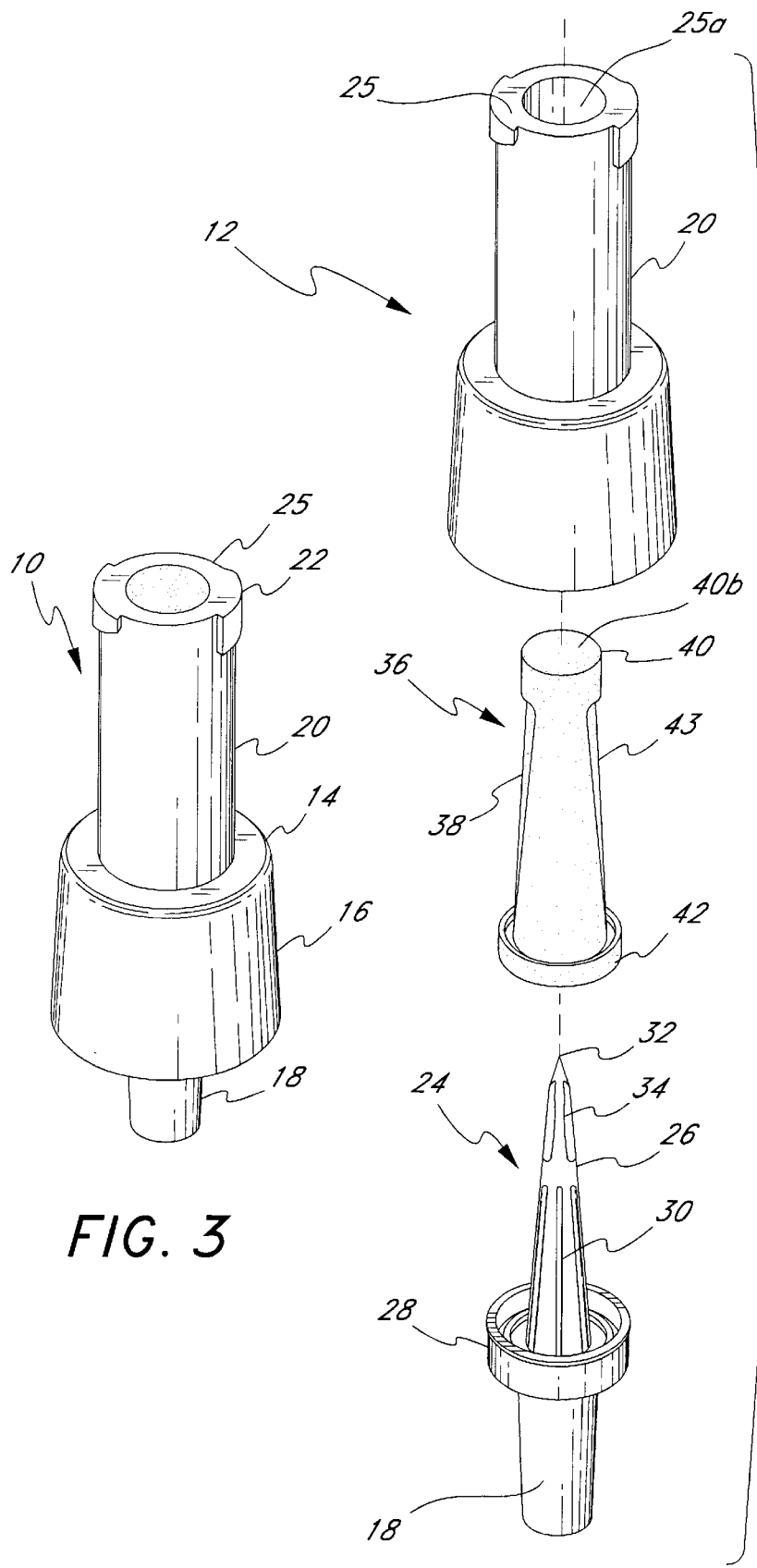
FIG. 3 is a perspective view of the first embodiment of the valve of this invention.
FIG. 4 is an exploded perspective view of the valve shown in FIG. 1 illustrating the spike, seal, and the body or housing components of the invention.
Figure 5:
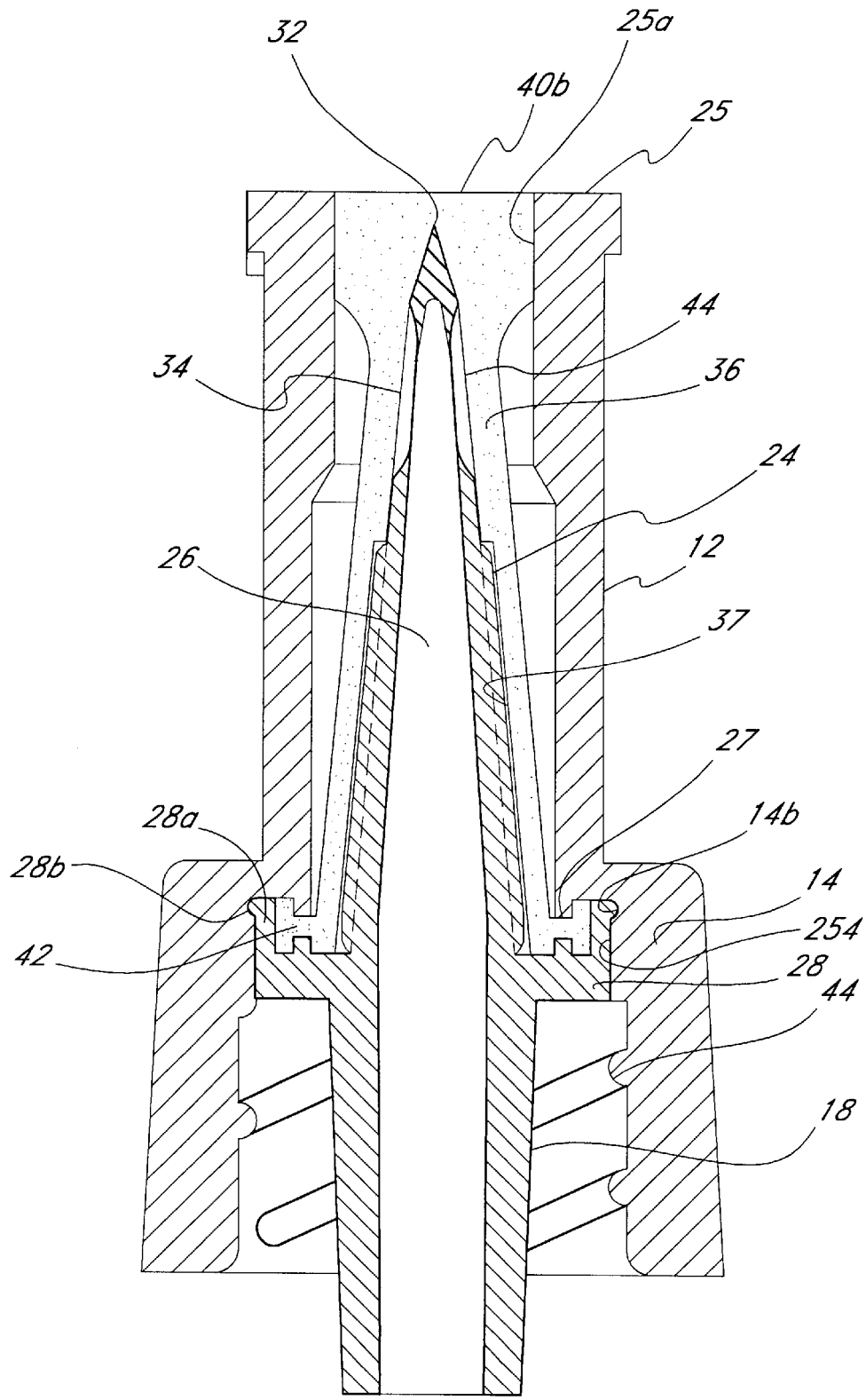
FIG. 5 is a longitudinal cross-sectional view of the valve of FIG. 1, after assembly by a first assembly method.
Figure 6:
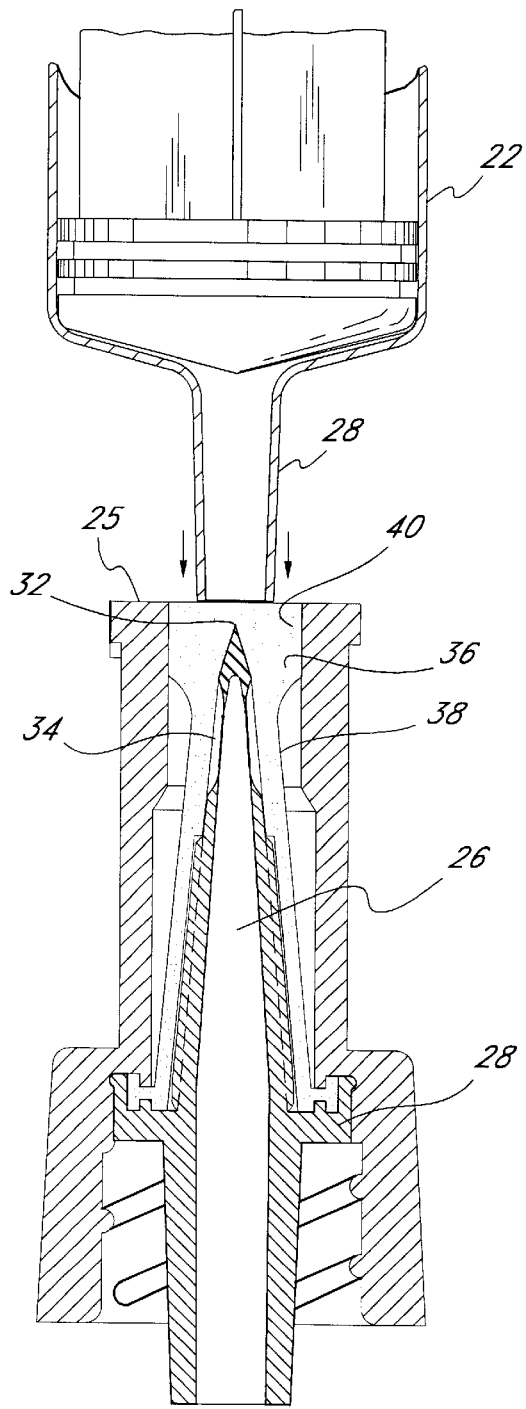
FIG. 6 is a schematic, longitudinal, cross-sectional view of the assembled valve of FIG. 1 before compressing the seal.
Figure 7:
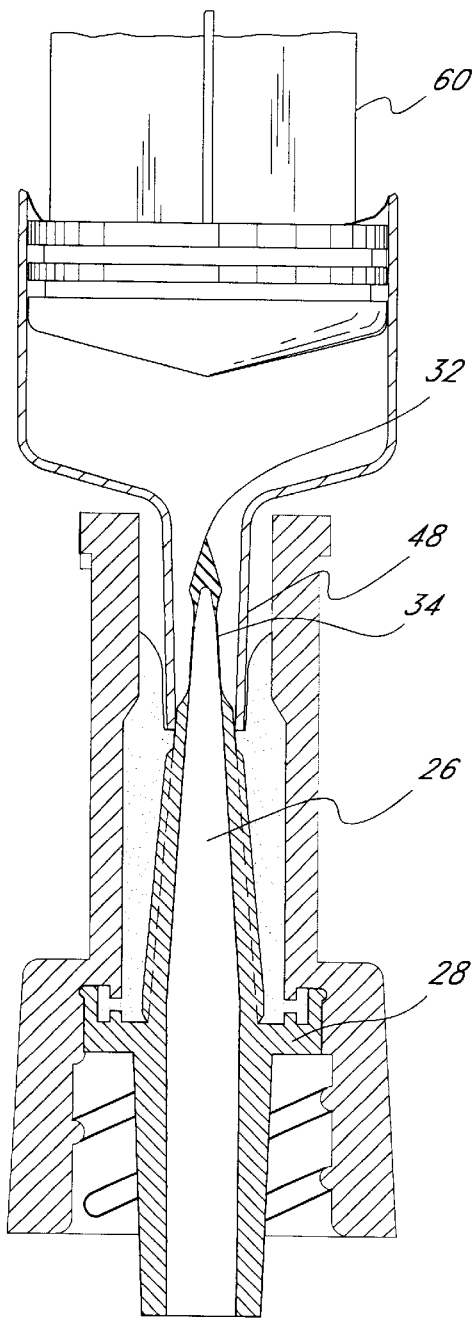
FIG. 7 is a schematic, longitudinal, cross-sectional view similar to FIG. 6 showing the valve during compression of the seal.
Figure 13:
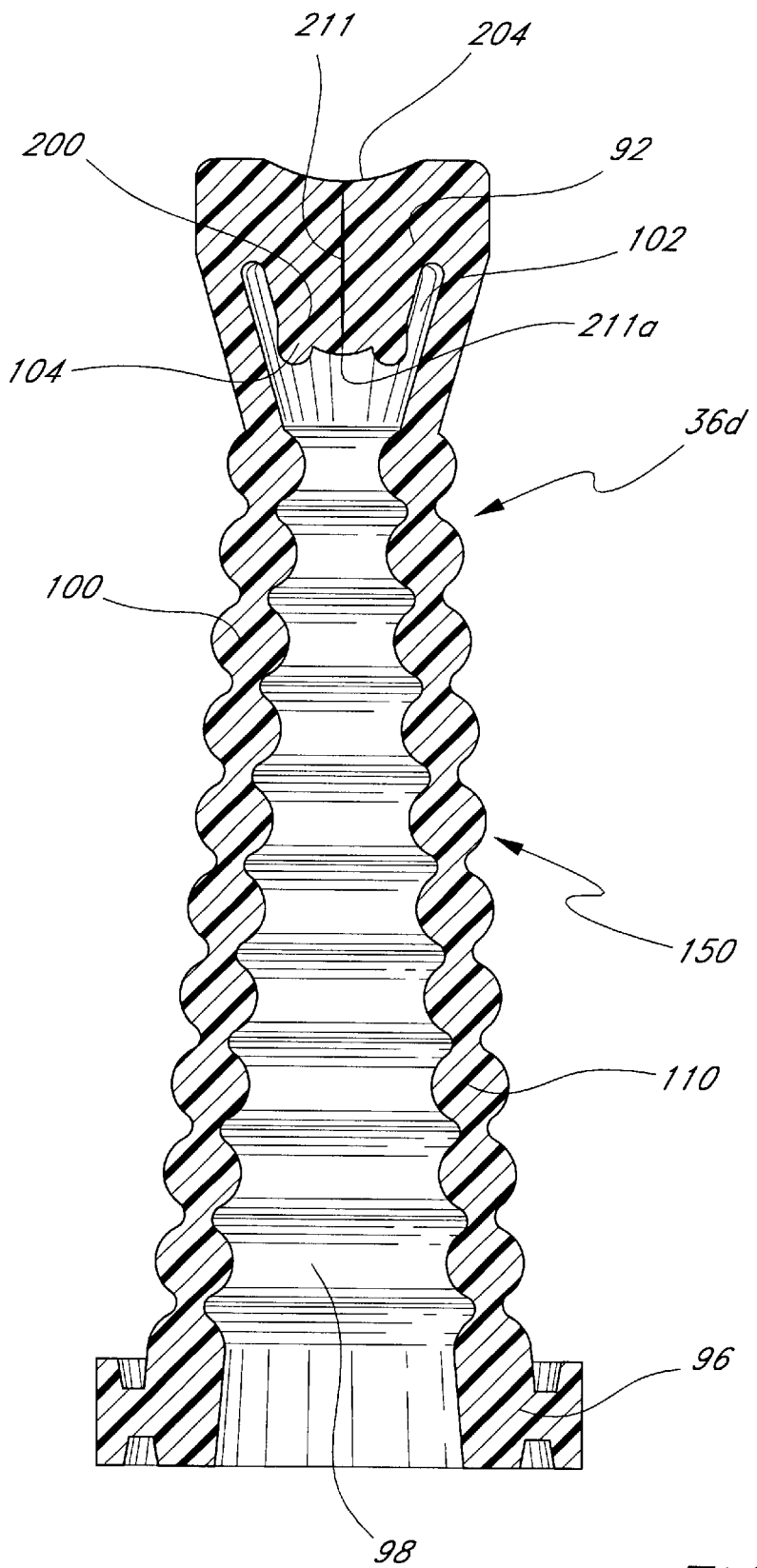
FIG. 13 is a longitudinal cross-sectional view of a sixth embodiment of the seal.

As best shown in FIGS. 3 and 4, the first embodiment of the invention, valve 10, includes a valve body or housing 12, a spike element 24, and a seal 36. The seal 36 is prepared from a resilient material that is flexible, inert, impermeable to fluid, and readily pierceable by the spike 26. In the embodiment shown in FIG. 13 depicting an alternate shaped seal 36d, this seal 36d has a precut slit 211 in its proximal end. This provides a tiny orifice through which the tip 32 of the spike element 24 may easily pass, yet still provides a fluid tight seal upon withdrawal of the spike element. These three components are assembled, as depicted in FIG. 5, for example, with the spike element 24 enclosed to prevent accidental sticks. FIG. 4 illustrates how the housing 12, seal 36, and spike element 24 are attached without the need to use any adhesive or other bonding agent or process. Mechanical connection with provides a fluid tight closure is attained as is discussed subsequently. As shown in FIGS. 6 and 7, the seal 36 moves within the housing 12, being pierced by the spike element 24 to expose the tip 32 of the spike element 24 to allow fluid to flow through the valve 10.

Referring to FIG. 3, one preferred embodiment of housing 12 has a bell-shaped skirt 16 and an upper, preferably cylindrical, conduit 20. The skirt 16 is integral with, and connected by an annular ring 14, to the upper conduit 20. The skirt 16 creates a shield for an inner conduit 18 of the spike element 24. This inner conduit 18 is preferably cylindrical in shape, and sightly tapered. Inner conduit 18 and upper conduit 20 comprise aligned hollow tubes so that inner conduit 18 and upper conduit 20 are in fluid communication with one another when the spike element 24 pierces the seal 36. There is an annular lip 25 surrounding a circular opening 25a in the top of the conduit 20 (see FIG. 4).

In the first embodiment, the upper conduit 20 is adapted to receive the tip or nose 48 of an ANSI standard syringe 46 (see FIGS. 6 and 7). It is, however, contemplated that the outer diameter of the upper conduit 20 can be of any size to accommodate the attachment of other connector devices thereto. Advantageously, the proximal end of the upper conduit 20 can be equipped with a locking mechanism to facilitate locking of the valve 10 to a variety of connector devices. For example, referring to FIG. 3, locking ears 22 near the proximal lip 25 of housing 12 are preferably provided such that the housing 12 can be locked into any compatible Luer-Lock device known to those with skill in the art. For example, referring to FIG. 19, conventional Luer-Lock threads 180 can be provided on the outer diameter of upper conduit 20.

Referring to FIG. 4, the spike element 24 has at its distal end the inner conduit 18 and at its proximal end a hollow spike 26 which is integral with the inner conduit. The inner conduit 18 and spike 26 present a continuous passageway for fluid during use. An annular cuff 28 on an intermediate portion of the spike element 24 is integral with, and interconnects, the inner conduit 18 and the spike 26. As illustrated in FIG. 5, the rim 28a of the cuff 28 abuts the underside of the inner ring 14, and has an annular detent 28b that snaps into an annular groove 14b in the underside of the ring. The cuff 28 serves two functions. First, it serves as an attachment device to the underside of the annular ring 14. Second, it serves as a support and attachment device for the seat 36.

The hollow spike 26 has a tapered conical shape, ending in a sharp, pointed tip 32. Preferably, along the length of the spike are raised, protruding ridges 30. These raised ridges 30 extend from the surface of the spike preferably between 0.2 and 2.0 mm. The ridges 30 are preferably aligned along the length of the spike as illustrated in FIG. 4. These ridges 30 serve to break any vacuum created when the spike 26 is sealed as described hereinbelow. Modifications to the alignment and orientation of the ridges are discussed hereinbelow in association with their function. Just distal the spike tip 32, there is situated at least one longitudinal through-hole 34 to permit fluid communication between the inner conduit 18 and the upper conduit 20. Preferably, there are three through-holes 34 within about 0.200 inch from the spike tip 32. These through-holes 34 may be of any size, however, the larger the size of the through-holes the greater the fluid flow rate through the valve 10. In a preferred embodiment, the size of the through-holes 34 are 18-gauge to provide a flow rate three times of a standard 18 gauge needle.

The seal 36 has a seal cap 40 with a generally flat top surface 40b, an outwardly tapered sidewall 38, and a lower lip 42. Its interior is hollow to provide the conically shaped cavity 37 (FIG. 5). Thus, the seal 36 slips easily over the spike element 24 to fit snugly within the cavity 37. The seal lip 42 is seated within the annular cuff 28 and wedged between the cuff and the underside of the ring 14. There are longitudinal grooves 34 (FIG. 4) along the length of the seal 36 which provide air pockets that facilitate compression of the seal 36 during use. The grooves 43 may be of variable shape or size to facilitate seal compression. In the first embodiment, there is a single groove 43 which completely surrounds the seal 36 between the seal cap 40 and the lip 42.

The base of the seal 36 has a width such that the seal lip 42 fits snugly into the annular cuff 28. The hollow interior or cavity 37 (FIG. 5) of the seal 36 is preferably tapered to conform internally to the shape of the spike 24, having a wall portion 44 which contacts the spike 24 distal seal cap 40. The exterior of the seal 36 is sized and shaped to fit inside the upper conduit 20 of the housing 12. The cap 40 reseals the valve 10 when the top surface 40b is above the through-holes 34. Preferably, the cap 40 substantially fills the opening 25a in the top of the conduit 20. Thus, after assembly, the top surface 40b of the seal cap 40 is essentially flush with the lip 25, so that the lip 25 and seal cap 40 can be swabbed with alcohol or other disinfectant without leakage of disinfectant into the valve 10. It is important that the surface 40b be exposed so that it may be swabbed with a disinfectant.

FIG. 5 illustrates a first embodiment of a valve of the present invention that has been assembled using a first assembly method. The spike 24, with contiguous inner conduit 18, is affixed to the housing 12 through the association of the external portion of annular cuff 28 and the inner surface 254 of annular ring 14. Specifically, the annular cuff 28 forms a tight fit within the annular ring 14, so that the force of friction between the external portion of annular cuff 28 and the inner surface 254 of annular ring 14 secures the spike 24 inside the housing 12. This first method of assembly requires that sufficient force be applied to the distal end of the spike 24 to overcome the force of friction between the annular cuff 28 and the annular ring 14, while holding the housing 12 in place, so that the spike 24 slides toward the proximal end of the housing 12, until the rim 28a of the annular cuff 28 abuts the underside of the annular ring 14. Alternatively, the spike 24 can be held in place, while the housing 12 is forced around the outside of the spike 24. A person of skill in the art will know of numerous techniques by which this method can be accomplished. In addition, although not necessarily required, the spike 24 may be affixed to the housing 12 by any one of a variety of additional measures known to those of skill in the art including, but not limited to, heat sealing, glue, pressure lock, bonding, or the like.

Proper selection of the dimensions of the annular cuff 28 and the annular ring 14 will provide a fluid tight closure for the valve 10. However, if the outside diameter of the annular cuff 28 is too small relative to the inside diameter of the annular ring 14, then, referring to FIG. 5, the spike 24 may slip in a downward direction relative to the housing 12, which may cause the valve 10 to leak. On the other hand, if the outside diameter of the annular cuff 28 is too large relative to the inside diameter of the annular ring 14, then the housing 12 may crack, particularly when the valve 10 is used to conduct lipids, or other fats, which may cause the entire spike 24 to expand. Although one of skill in the art will be able to determine appropriate dimensions for the annular cuff 28 and the annular ring 14, the present inventors have developed an improved method of assembling an improved valve 11 of the present invention which will be described below. This improved valve and improved method of assembly will reduce the likelihood that a valve will either leak or crack, by securing the spike 24 inside the body 12, without requiring as much pressure between the annular cuff 28 and the annular ring 14.

The seal 36 fits into the annular cuff 28 and is held in place by an internal lip 27 along the internal portion of the annular ring 14 of the housing 12. The length of the spike 24 is such that, after assembly, the tip of the spike rests below the plane defined by the lip 25 of the housing 12. Preferably, the spike tip 32 is approximately from 0.525" to 0.1" below the lip 25 of the housing 12. The seal 36 fits snugly against the spike 24 and is essentially flush with the lip 25 of the housing 12. The spike tip 32 is thus embedded within the seal cap 40 prior to use or may be approximately 0.025" distal the seal cap 40 when the valve 10 is in the closed position. The inner circuit 18 is partially shielded by the bell shaped skirt 16 of the housing 12 (see FIGS. 3–5). The inner surface 254 of the bell shaped skirt 16 preferably has protruding threads 45 as an optical locking mechanism for attaching a medical implement thereto. Further, other medical devices can be pressure fit over the outer portion of inner conduit 18 without direct association with the protruding threads 45.

During use, the invention is designed to be adapted as a two-way valve. The orientation of the valve is independent to fluid flow and dependent on the preferred orientation of the preexisting connections. Thus, the invention can be used as a valve connector for an intravenous central or peripheral piggyback connection in either orientation. Parenteral fluid is delivered to patients through tubing such that the liquid flows from a container through a needle into the patient. The containers are frequently changed or additional fluid bottles are added. The invention disclosed herein is designed to interconnect medical implements along the route of fluid delivery to the patient. However, the invention is also useful in any environment in which a resealable fluid valve is desired. During use, a connector of the appropriate size is fitted over the inner conduit 18. Locking can be achieved by a Leur-Lock mechanism, a pressure fit or any other locking mechanisms known to those with skill in the art, as described above. Thus, in one example, fluid passes from the inner conduit 18 into the spike 26. However, fluid flow is locked in place by the seal 36.

FIGS. 6 and 7 illustrate valve activation. FIG. 6 illustrates a syringe 22 connected to the proximal end of the valve 10. However, the connecting implement could be any number of medical implements known to those of skill in the art. The nose 28 of the syringe 22 is placed on the seal cap 40 inside the lip 25 of the housing 12. The application of pressure on the syringe 22 in the direction of the arrows, as illustrated in FIG. 6 creates pressure on seal cap 40. The resulting downward pressure compresses the seal 36. This pushes the tip 32 of the spike 26 through the seal cap 40 to expose the through-holes 34. Compression is facilitated by the grooves 38. Fluid is now able to flow into the syringe 22, or vice versa, depending on whether fluid is to be withdrawn from the patient or medication injected into the patient. FIG. 7 shows valve 10 opened by insertion of the nose 28 of the syringe 22 into the opening 25a. A syringe plunger 60 in the syringe 22 is retracted thereby creating a vacuum to draw fluid through the valve 10 into the syringe. For intravenous applications, the valve 10 can be orientated in the position diagramed in FIGS. 6 and 7, or it can be rotated 180° such that fluid flows in the opposite direction.

Upon removal of the syringe from spike 26, as shown in FIG. 6, the seal 36 is free to return to its original shape and cover through-holes 34. The ability of the seal 36 to return to its original shape is determined by the resiliency of the material used to prepare the seal 36. In addition, the ability of the seal 36 to return to its original shape is facilitated by the protruding ridges 30 formed on the external surface of the spike. During compression, a vacuum may form in the area between the spike 26 and the seal 36, thereby preventing the seal 36 from returning to its original position. The protruding ridges permit air to pass along the spike/seal interface to prevent vacuum formation and allow free return of the seal. The ability of the seal 36 to deform reversibly and returns to its original position is particularly useful because (1) it immediately stops fluid flow through the valve 10, (2) it covers the recessed spike 26 to maintain its sterility, and (3) it reduces the risk that the spike could inadvertently pierce another object or person. In addition, since the valve 10 lacks movable parts, except for the seal, it is unlikely that when the seal 36 is pushed down, the valve 10 would fail to function.

Advantageously, the through-holes 34 are located relatively low on the spike 26. Thus, the through-holes 34 are sealed relatively early in the process as the seal 36 returns to its original configuration when the valve 10 is closed. In one preferred embodiment the through holes 34 are located 0.075" below the spike 32 (see FIG. 4). Additionally, the through-holes 34 are sealed even if the seal 36 does not fully return to its original configuration depicted in FIG. 6. Further, the ability of the seal 36 to return reversibly to its original position permits the reuse of the connector valve 10. Following disconnection, and before use, the surface of the pierced seal cap 40 is essentially flush with the housing 12. Thus, this flush surface can advantageously be sterilized with alcohol or other surface decontaminating substances. The skirt 16 and upper conduit 20 advantageously shield both connections from the surrounding environment to protect the sterility of the connection. Further, both the skirt 16 and upper conduit 20 function as collection reservoirs to prevent fluid from dripping from the valve 10 during manipulation.

A cover cap (not shown) can be supplied to fit over the upper conduit 20 as further protection for the seal surface between use. Such a cover cap, however, is not needed to maintain sterility since the seal 36 may be swabbed with a disinfectant after each use. The reversibility of the seal 36 makes the vale 10 particularly attractive as a connector valve to provide fluid communication between two fluid lines. Therefore, the present invention provides for placing a first fluid line in communication with a second fluid line using the valve disclosed herein. The reversibility of the valve 10 permits multiple fluid lines to be successively added, for example, to a fluid line in direct communication with a patient's vein. Since the valve is easily sterilizable and sealable, fluid lines can be added and removed without disconnecting venous contact.

The valve 10 is preferably prepared from a hard plastic, but it is additionally contemplated that the valve could be prepared from other medically inert materials known to those in the art. The spike element 24 is preferably prepared from the same material as the housing 12. One particular advantage of this invention is that it does not rely on the use of metal needles. This dramatically reduces the risk of skin puncture during use and manufacture. Further, the upper conduit 20 serves as a shield to the spike 26 such that skin puncture is further reduced. The spike 26 need only be strong enough to penetrate the seal cap 40, or if necessary, to pierce a connecting septum.

In the embodiment of the invention illustrated in FIGS. 4 through 6, the through-holes 34 are placed distal spike tip 32. This placement provides two important advantages. First, the placement of the through-holes 34 facilitates resealing of the valve 10 after use. Second, if the through-holes were placed at the spike tip 32, the holes 34 may core the seal cap 40 thereby introducing seal particulate into the fluid flow and possibly plugging the holes 34. Thus, the longitudinal placement of the through-holes distal spike tip 32 prevents the introduction of particulates into the fluid path and/or plugging of the through-holes 34. It is additionally contemplated that the number and diameter of the through-holes 34 can be adjusted to accommodate different fluid velocities. In a preferred embodiment, the preferred velocity of fluid passing through the through-holes 34 is equal to or greater than the flow rate through an 18 gauge needle. Through-holes larger than 18 gauge will, of course, facilitate greater fluid velocities.

An important advantage of the invention is that the valve 10 has very little dead space, thus the volume of liquid entering into the valve is substantially equivalent to the volume of fluid leaving the valve. Further, the total equivalent fluid volume of the valve is very small such that the volume of fluid flowing through the system in order to place the valve in fluid communication with a medical implement such as a syringe 22 is substantially zero.

Figure 9:
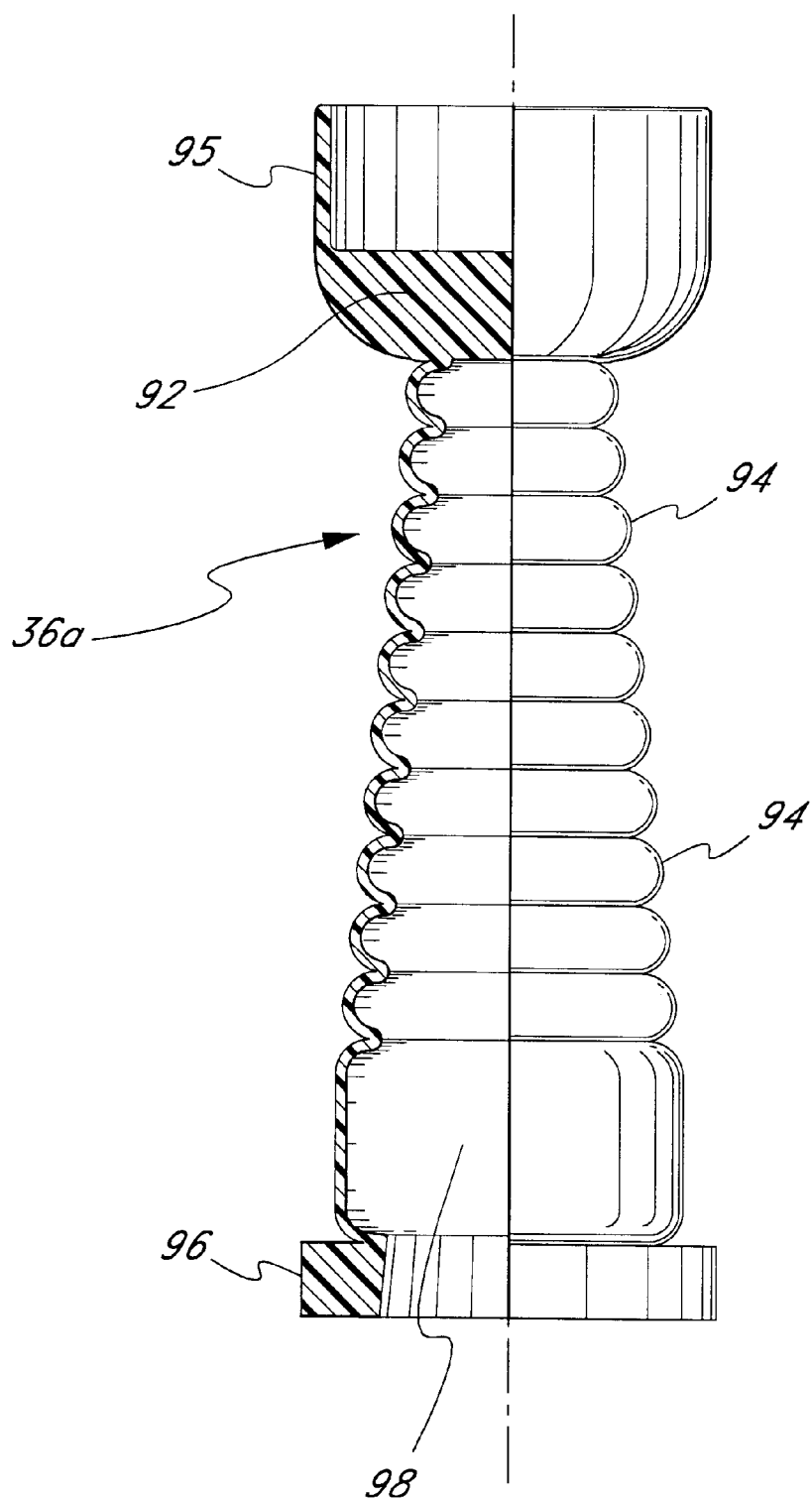
FIG. 9 is a side elevation view, partially in cross-section, of a third embodiment of the seal.

An alternative embodiment of the seal, a seal 36a, is shown in FIG. 9. Seal 36a comprises a seal cap 92 at the proximal end thereof and a seal lip 96 at the distal end thereof. A cup-like annular flange 95 is provided proximal seal cap 92. The seal cap 92 and seal lip 96 are connected by a seal wall consisting of a plurality of ringed wall portions 94 that expand and collapse in an accordion like fashion. During compression of the seal 36a, the diameter of the ringed wall portions 94 expand outward in the radial direction. There are air pockets 13a (FIG. 10) between ring portions 94 and the housing and air pockets 13b between spike 24 and seal 36a. The seal 36a contains a cavity 98 distal seal cap 92 and adjacent the ringed wall portions 94. The seal 36a interacts with spike 26 (FIG. 6) and other components of the present invention in a similar fashion to seal 36 of FIG. 6.

Figure 10:
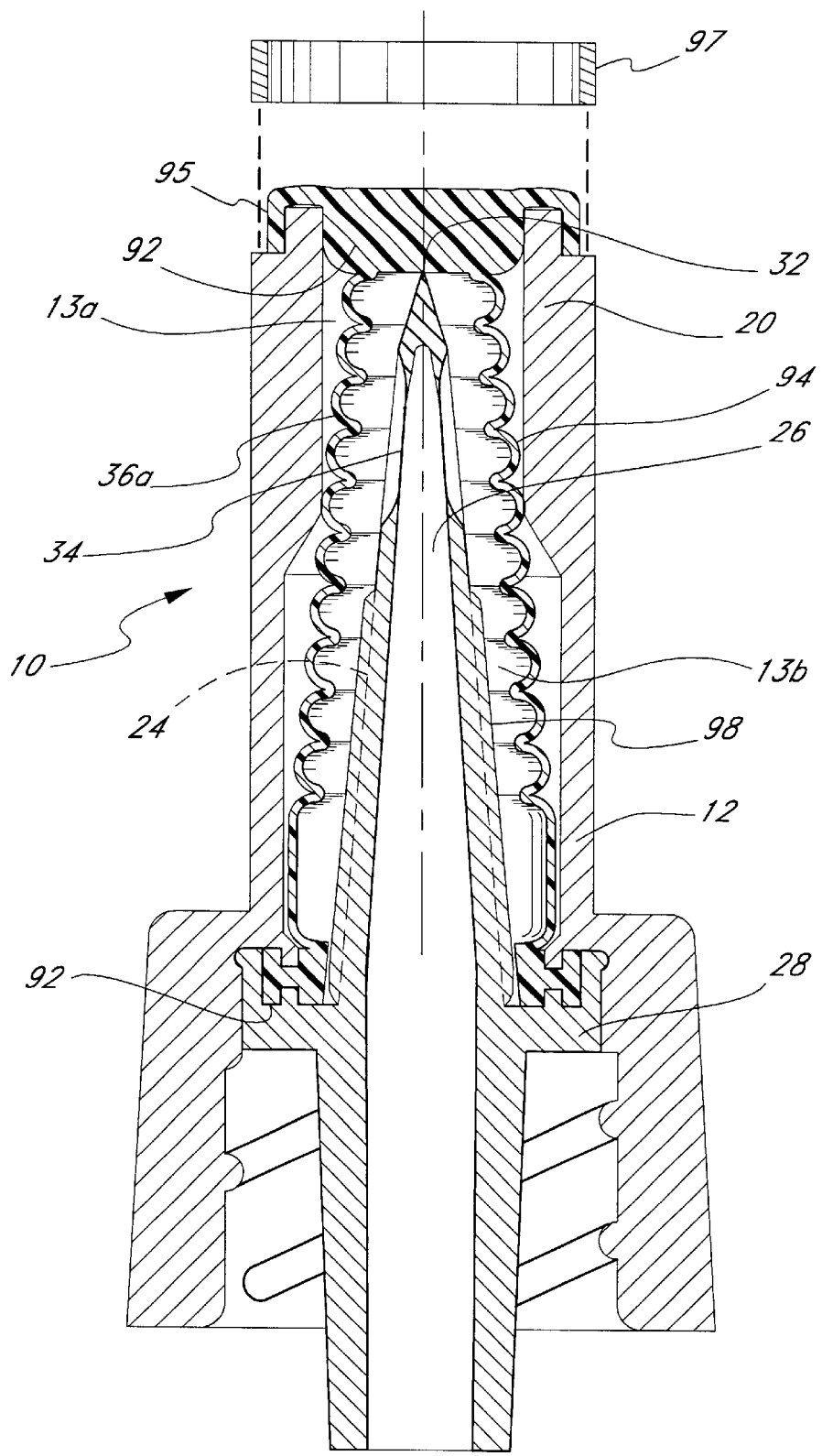
FIG. 10 is a longitudinal cross-sectional view of the assembled valve of FIG. 1 using the seal of FIG. 9.

Referring to FIG. 10, the cup-like annular flange 95 may be stretched around the upper conduit 20 and held in place by an annular ring 97. This creates a trampoline like effect that assists returning the seal 36a to a decompressed state after withdrawal of a syringe (not shown). This embodiment has two advantages. First, the proximal end of the valve 10 can be swabbed with alcohol or other disinfectant without leakage of disinfectant into the valve 10. Second, by affixing cup-like annular flange 95 to upper conduit 20 at the proximal end thereof with annular ring 97, the repeated deformation and reformation of the seal 36a is assisted.

Figure 11:
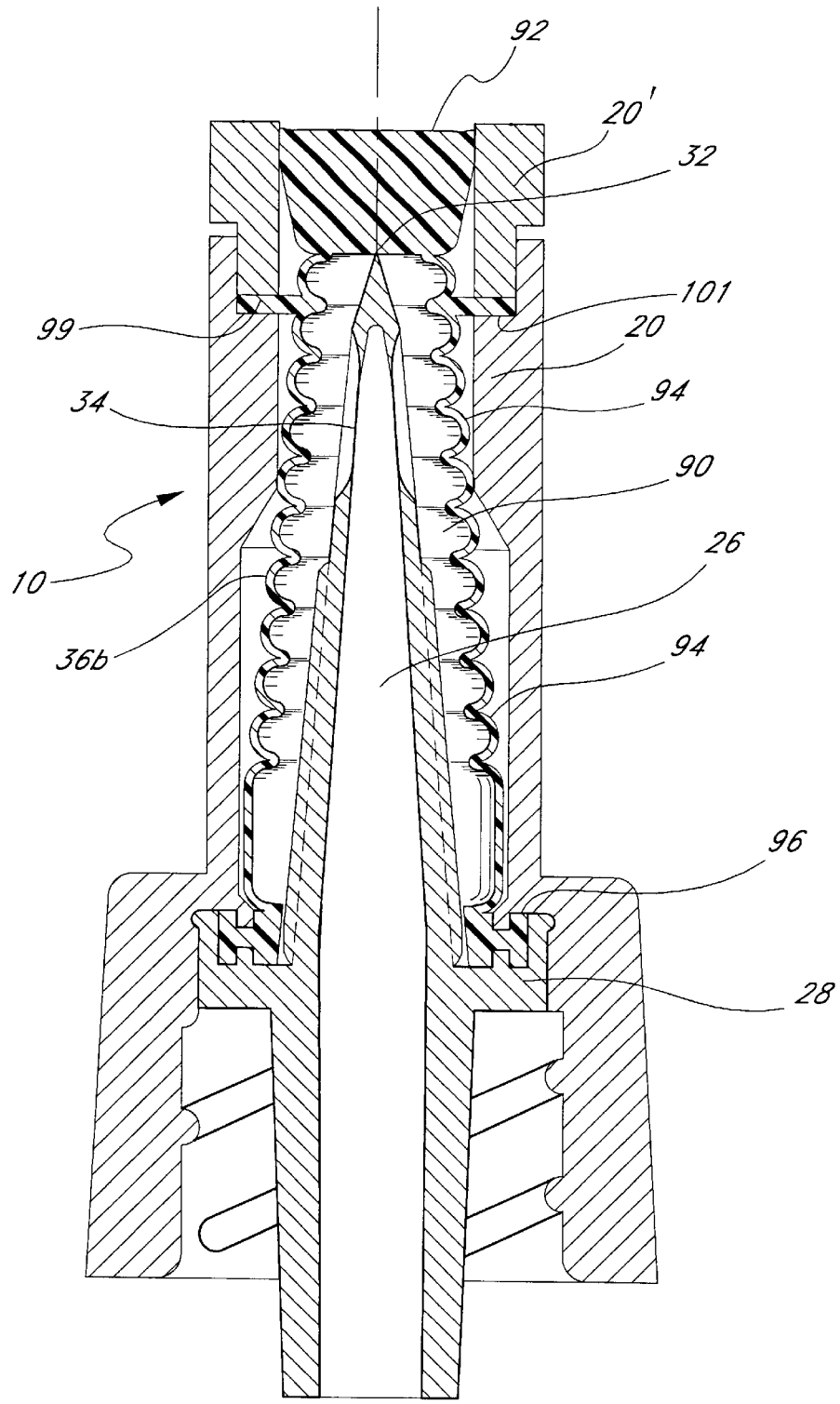
FIG. 11 is a longitudinal cross-sectional view of the assembled valve of FIG. 1, using a fourth embodiment of the seal.

An alternative embodiment of the seal, a seal 36b is shown in connection with the valve 10 in FIG. 11. The seal 36b is similar to the seal 36a and is comprised of seal cap 92, a side wall consisting of ringed wall portions 94 and a seal lip 96. It also has an outwardly extending ring 99 which is at a right angle with respect to the longitudinal axis of the valve 10. This ring 99 is used to attach the seal 36b to upper conduit 20. Preferably, an upper conduit annular plug 20' is inserted within upper conduit 20 to create a tight fit between perpendicular ring 99, a ledge 101 in the upper conduit 20, and the plug 20'. The ring 99 assists in the reformation of seal 36b to enclose spike 26 upon withdrawal of a syringe (not shown).

Figure 12:
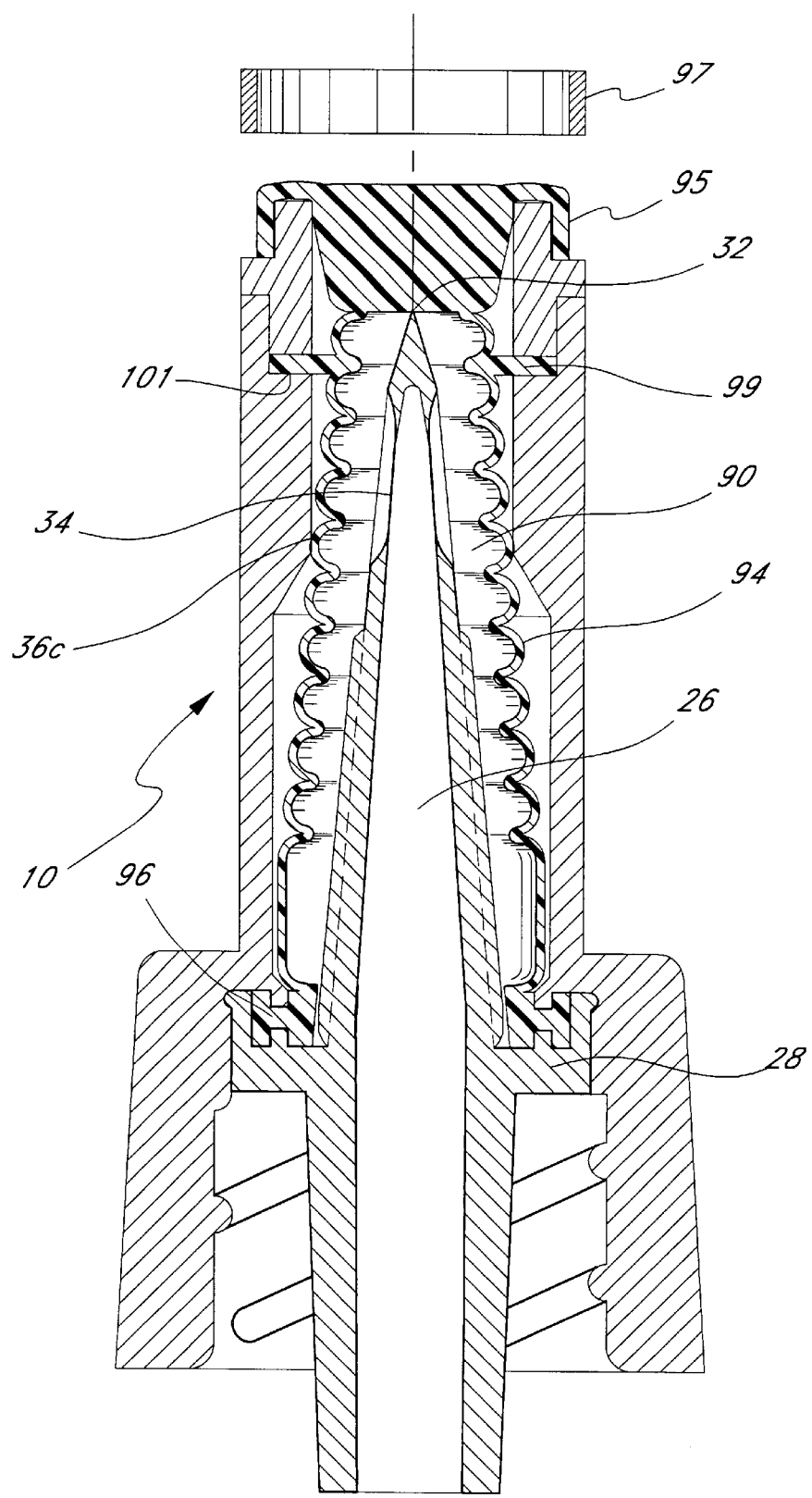
FIG. 12 is a longitudinal cross-sectional view of the assembled valve of FIG. 1, using a fifth embodiment of the seal.

As shown in FIG. 12, the cup-like annular flange 95 and ring 99 may both be used in connection with the valve 10, to provide the seal 36c. This seal 36c, provides rapid reformation upon withdrawal of a syringe (not shown) and realizes the advantages of both the seals 36a and 36b.

Another alternative embodiment of the seal, a seal 36d, is shown in FIG. 13. In this embodiment, the seal 36d is comprised of seal cap 92, seal lip 96, and a side wall 150 comprised of circular tires 100 stacked in series one on top of an adjacent larger diameter lower tire. The circular tires 100 are preferably solid throughout the diameter of the cross-section thereof. These circular tires 100 will deform and reform upon, respectively, compression and decompression of the seal 36d, thereby exposing or covering a spike (not shown) as the case may be.

Figure 14:
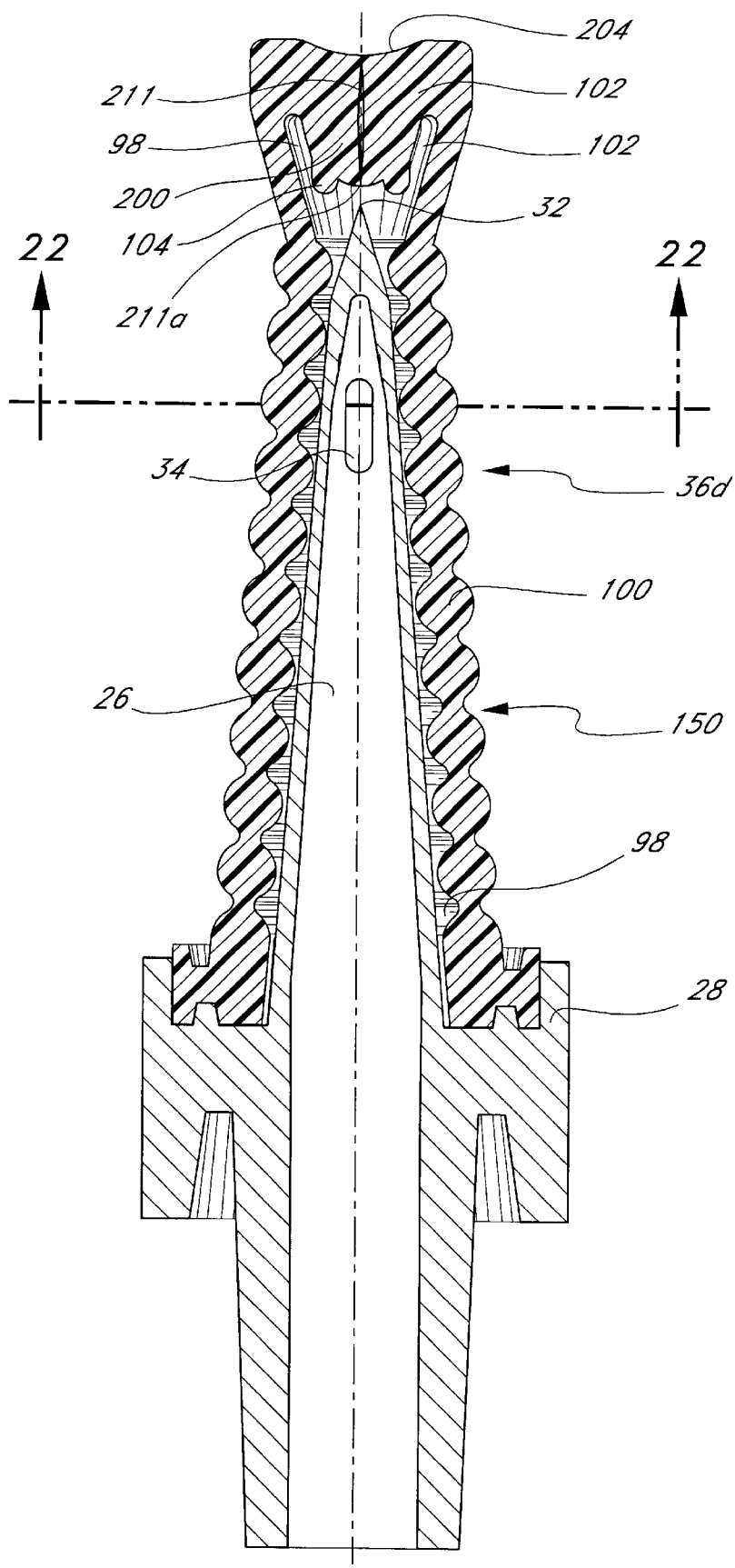
FIG. 14 is a longitudinal section of the seal shown in FIG. 13 used in connection with the spike device shown in FIG. 2.
Figure 15:
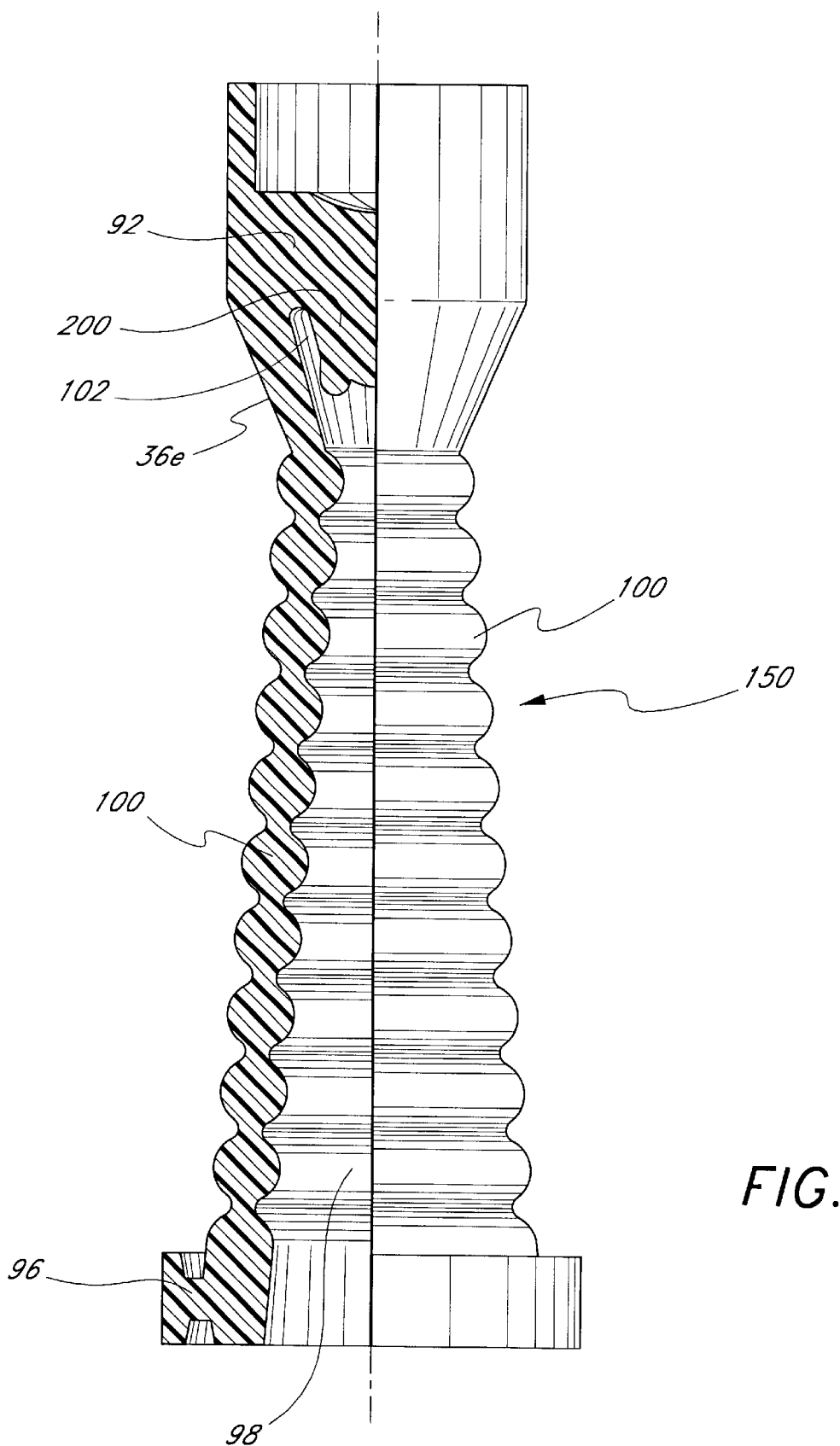
FIG. 15 is a longitudinal partial cross-sectional view of a seventh embodiment of the seal of this invention.
Figure 16:
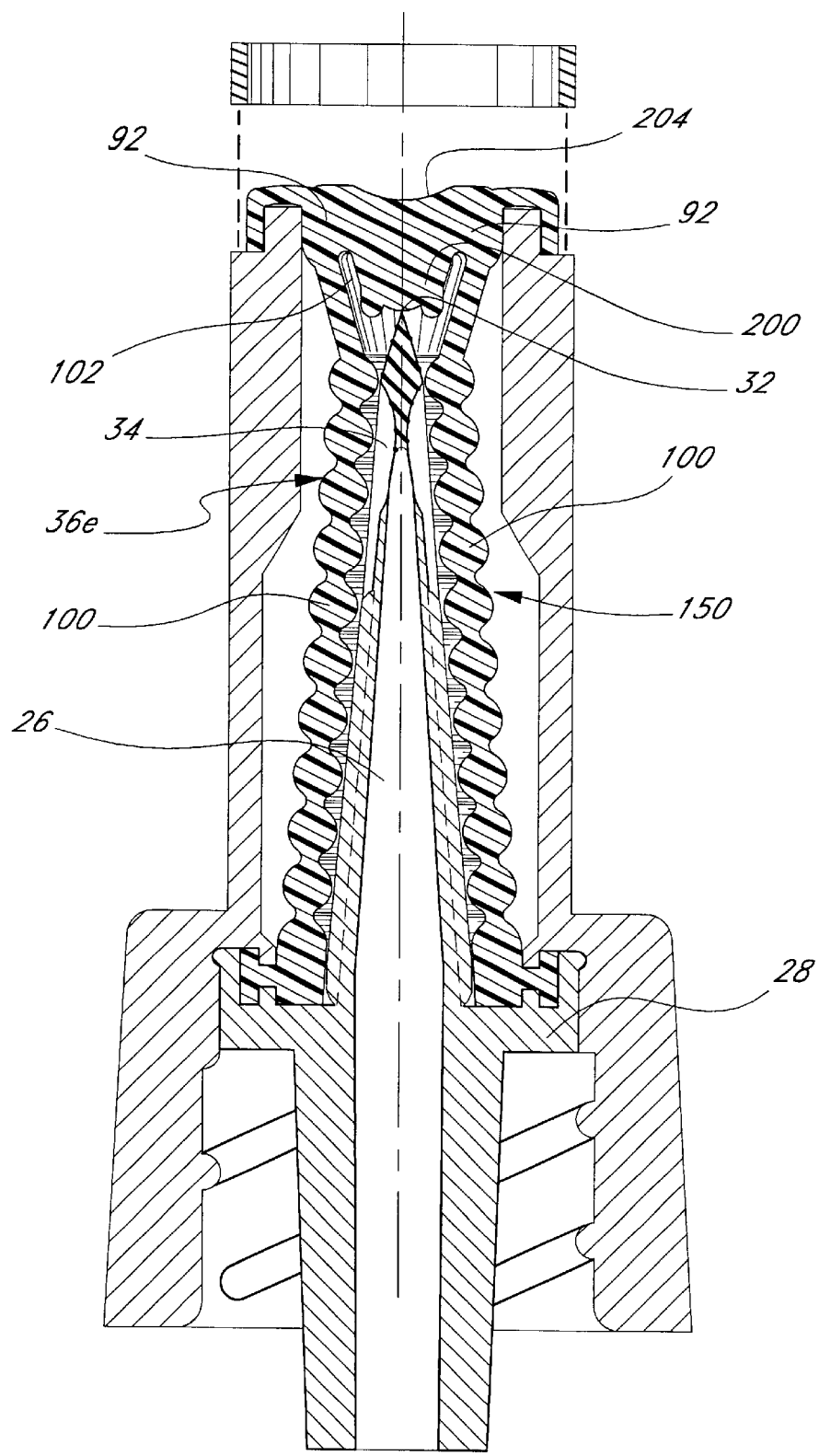
FIG. 16 is a longitudinal cross-sectional view, after assembly, of the embodiment of the valve shown utilizing the seal of FIG. 15.
Figure 17:
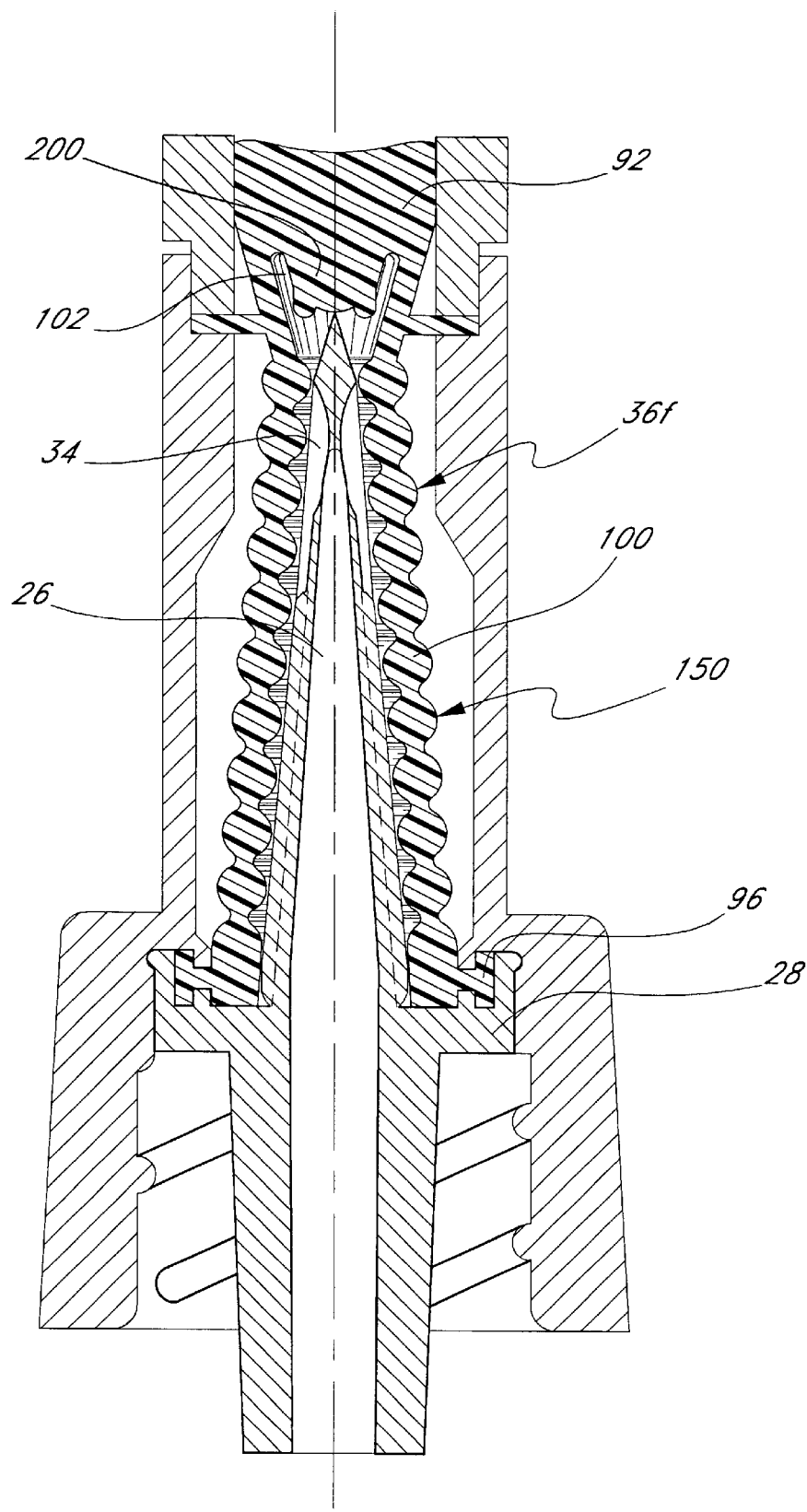
FIG. 17 is a longitudinal cross-sectional view, after assembly, of the eighth embodiment of the valve of this invention.
Figure 18:
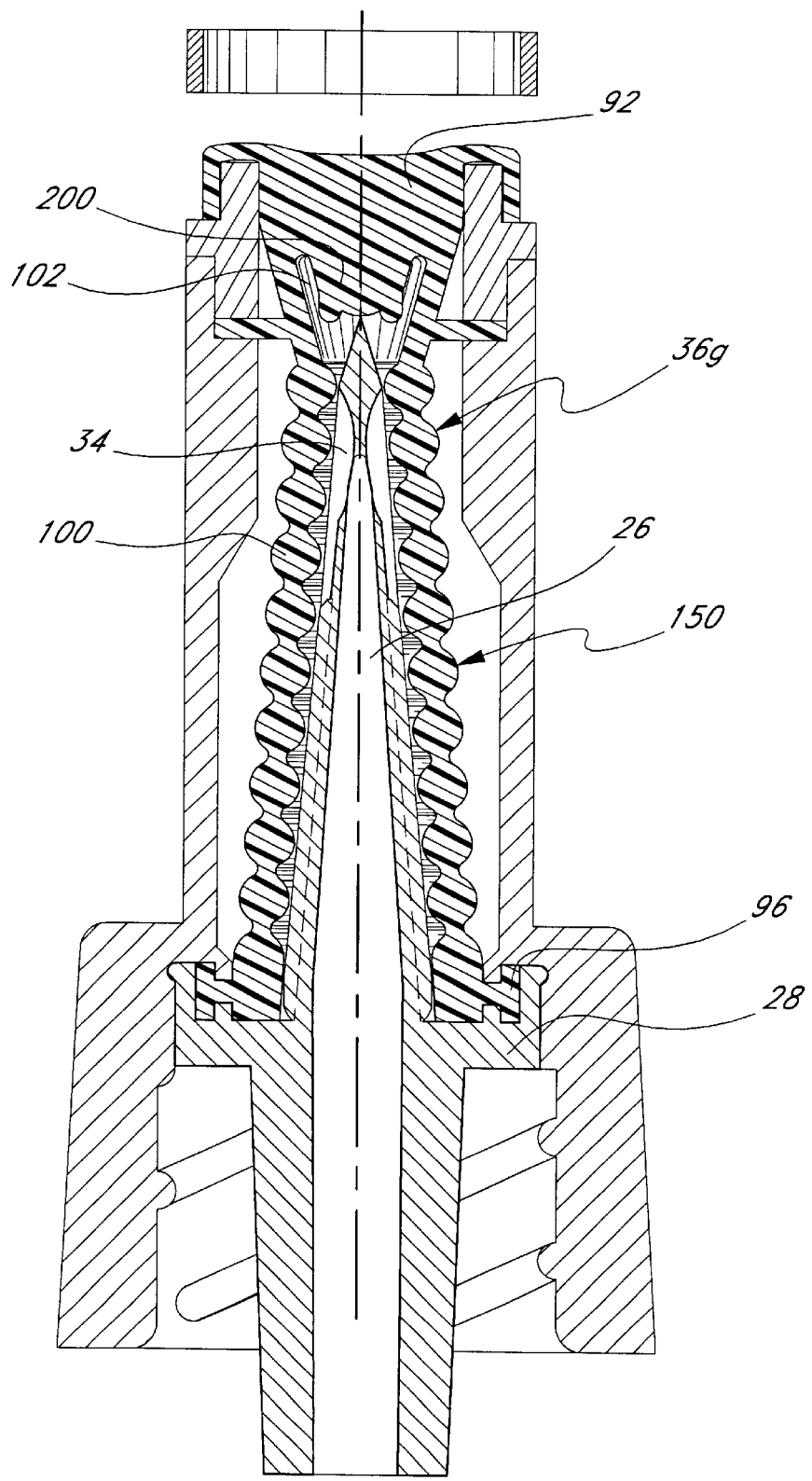
FIG. 18 is a longitudinal cross-sectional view, after assembly, of the ninth embodiment of the valve of this invention.
Figure 19:
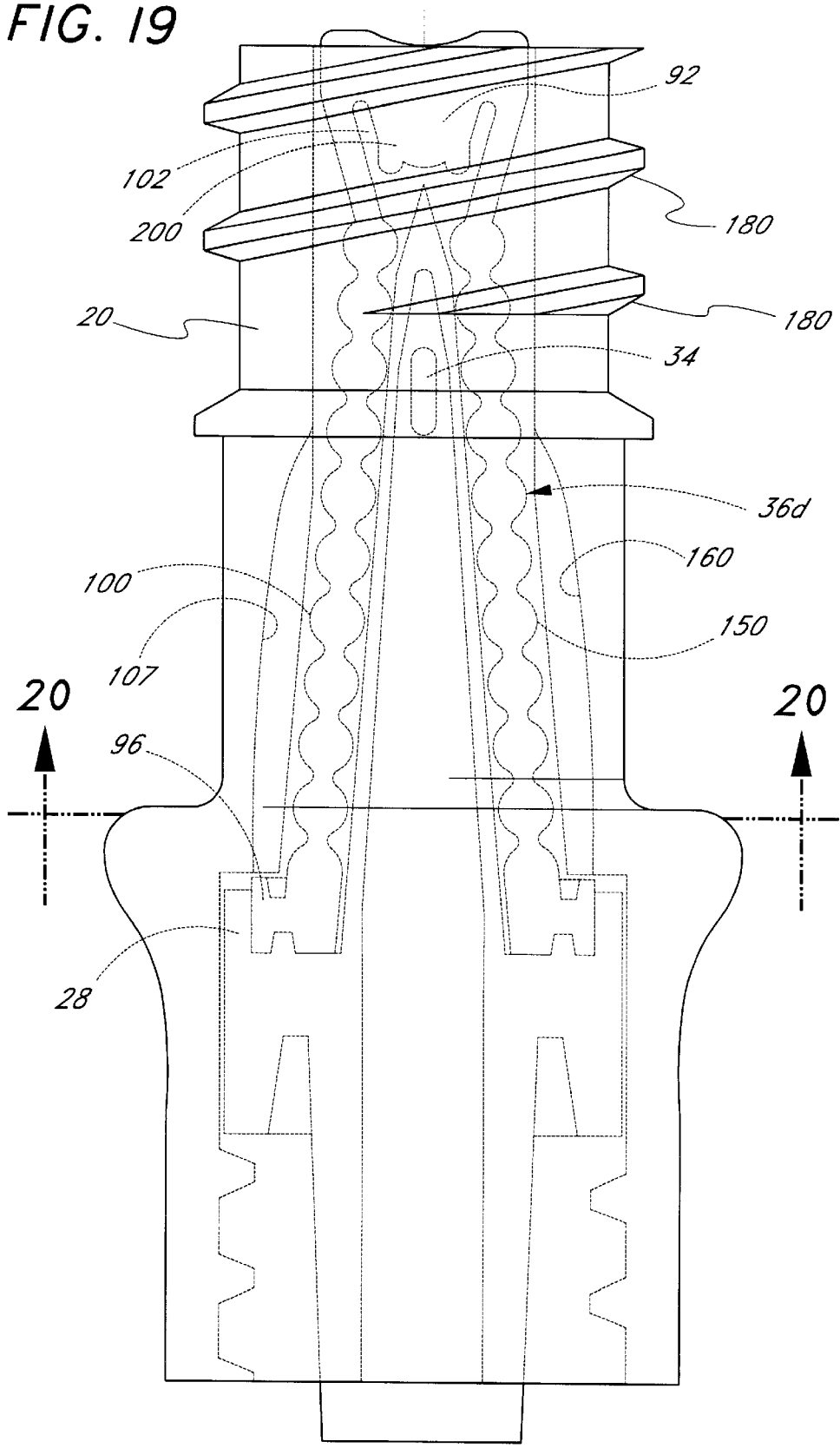
FIG. 19 is a side elevational view, after assembly, of the seal and spike shown in FIG. 14 connected to the body or housing shown in FIGS. 20 and 21.
Figure 20:
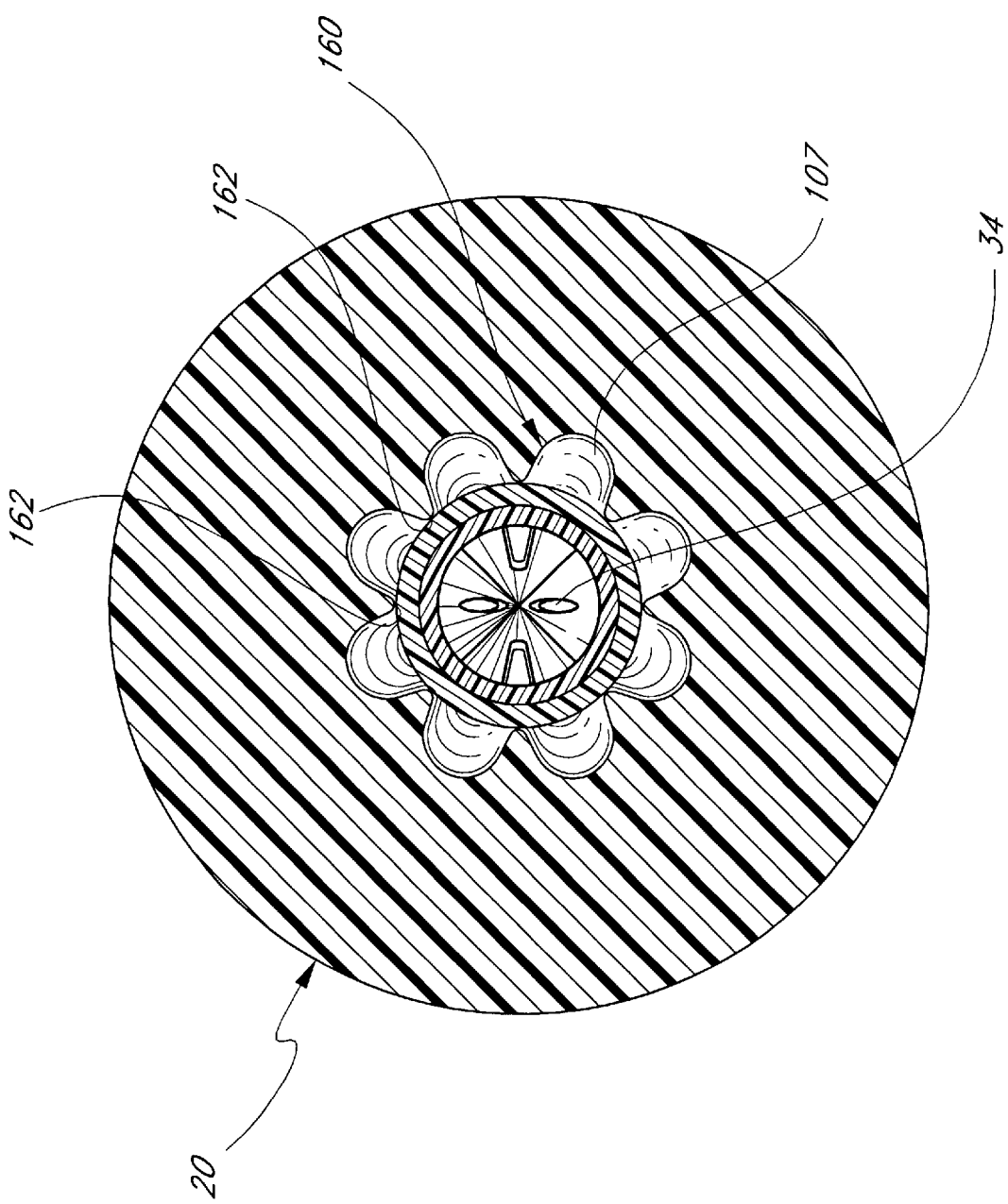
FIG. 20 is a cross-sectional view taken along line 20—20 of FIG. 19.
Figure 21:
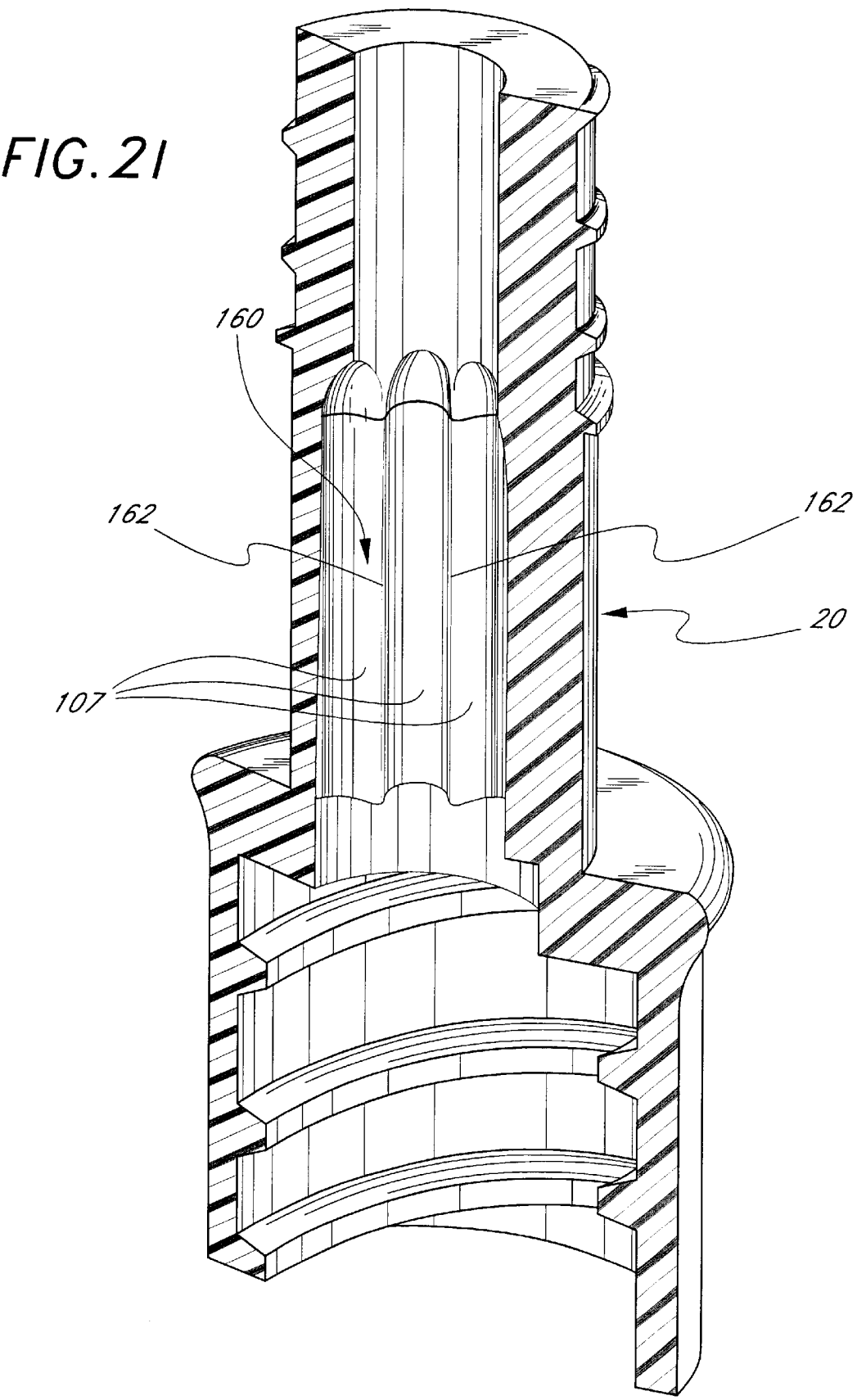
FIG. 21 is a perspective view, with sections broken away to show the wall structure of the cavity containing the seal shown in FIGS. 13 and 14.

As mentioned above, preferably seal 36d has a percut slit 211 in the cap 92 lying along the longitudinal axis of the valve 10. The seal cap 92 has a unique configuration that insures that the slit 211 closes and is sealed upon withdrawal of a syringe (not shown) and reformation of the seal 36d. It includes an enlarged, internal, pressure responsive member 200 which is integral with the cap 92. Between the proximal end of the side wall 150 and the member 200 is an annular space 102 which is filled with the fluid in the cavity 98. This fluid is under pressure, for example at the blood pressure of the patient to which the valve 10 is attached. Referring to FIG. 14, fluid, for example the patient's blood, flows through the holes 34 in the spike 26, filling the cavity 102. This fluid presses against the exterior of the member 200, closing the slit 211 when the seal is decompressed as shown in FIGS. 14 and 19. The pressure from this fluid creates a high pressure seal which prevents fluid from escaping valve 10 through the slit 211. There is a semi-cylindrical annular flange tear ring 104 on the end of the member 200 which advantageously extends the useful life of seal 36d.

Preferably, there is a tear ring 104 integral with the member 200 along the perimeter of the internal surface of the member 200, and a slight saucer-like depression 204 in the external surface of the seal. The pressure responsive element in the decompressed state closes any orifice in the seal 36d to provide an essentially fluid-tight seal while in the decompressed state. The pressure responsive member 200 enables the valve to maintain a fluid-tight seal even at very high pressures sometimes experienced in medical applications, particularly when the valve 10 is connected to a patient's artery. The center of the member 200 and the annular space 102 are coaxial with the entryway 211a to the orifice 211. The pressurized fluid fills the annular space 102 to apply pressure that compresses the member 200 to tightly close the entryway to the orifice. In a preferred embodiment the distance from the entryway 211a to the proximal end of seal cap 92 is from 0.500 to 0.075 inches and more preferably approximately 0.100 inch.

Figure 22:
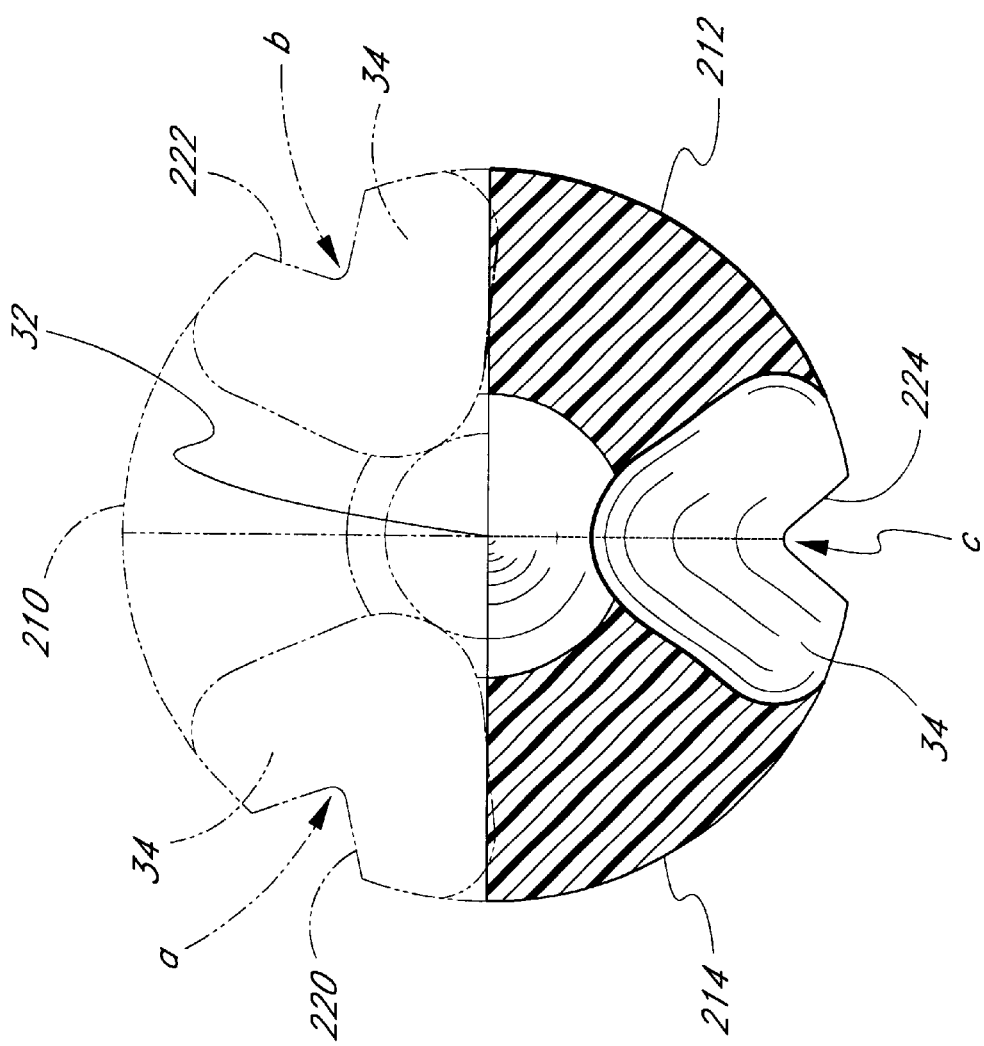
FIG. 22 is a greatly enlarged, cross-sectional view taken along line 22—22 of FIG. 14.

As best illustrated in FIG. 22, the tip 32 is designed to avoid tearing the seal. Tip 32 has three facets 210, 212, and 214 which are joined with each other along parting lines a, b, and c. This junction of the facets 210, 212, and 214 frequently is ragged and will tear the seal 36d. This is prevented by the parting lines a, b, and c, or junctions, being disposed within recesses 220, 222, and 224, respectively, to provide "buried parting lines."

Another alternative embodiments of the present invention using the seal 36d is shown in FIG. 8 and FIGS. 19 through 21. In this embodiment, the inner wall 160 of the upper end of the conduit 20 is provided with at least one, and preferably, a plurality of radial indentations 107. The indentations 107 are elongated disposed generally parallel to the longitudinal axis of the valve 10 in a symmetrical, star-like configuration. Each indentation has opposed lateral edges 162 which engage the seal 36d upon compression of the seal 36d. The indentations provide space into which the seal 36d expands upon compression.

Figure 8:
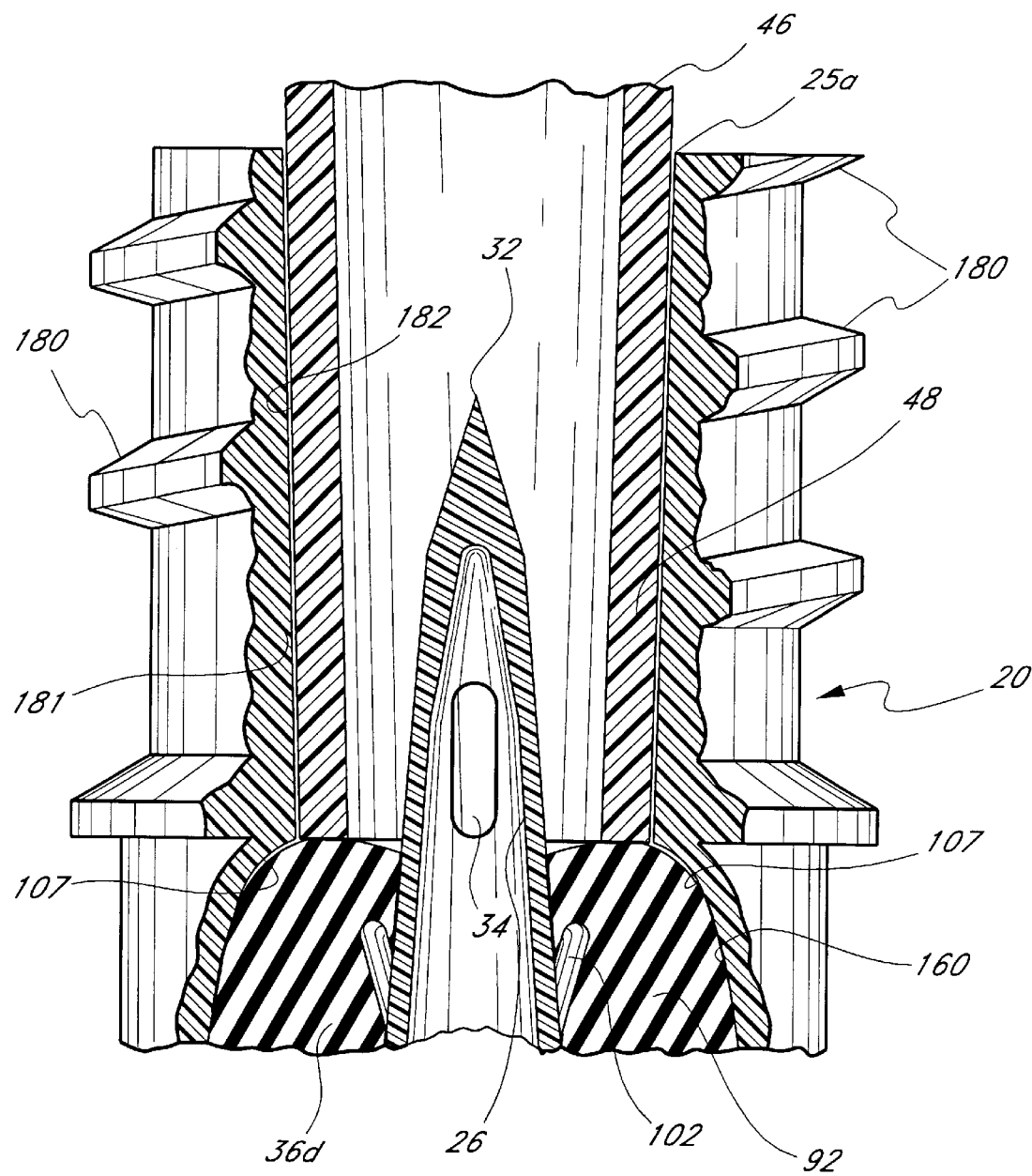
FIG. 8 is a schematic illustration of an ANSI delivery end of a medical implement compressing the seal of the valve of this invention.

As best shown in FIG. 8, the wall 181 of the proximal end of the conduit 20 is tapered inward at the same angle as the nose 28 of the syringe 22. In accordance with ANSI standards, the taper is 0.006 inch per linear inch. The wall 182 of the syringe nose 28 bears against the wall 181 as the nose slides into the opening 25a to push the seal 36d inward compressing it and forcing the tip 32 of the spike 26 to enter the slit 211. The seal 36d expands upon compression to fill essentially completely the upper portions of the indentations 107. Some sections of the seal 36d are wedged between the edges 162 and other sections fill the indentations 107. As the liquid flows through the nose 28 through holes 34, air in the nose 28 is forced out of the nose 28 and expelled from valve 10 between walls 181 and 182. Thus, essentially the entire prescribed dosage is delivered through valve 10 to the patient. Fluid flows through the through-holes 34, but does not leak between either the seal 36d and the wall 181 or between the abutting walls 181 and 182.

FIGS. 15, 16, 17, and 18 depict embodiments of seals, namely, seal 36e, seal 36f, and seal 36g, which are substantially the same as the seals 36a (FIG. 10), seal 36b (FIG. 11), and seal 36c (FIG. 12), except the side wall 150 employing the circular tire 100 is used in place of the accordion wall portion 94.

Other components of the present invention interact with the various embodiments of the seal in a similar fashion to their interaction with seal 36 of FIG. 4. Prior to use of valve 10, it is preferable that the seal caps 40 or 92 be pierced centrally by a steel needle in the axial direction, precutting the seal to provide the slit 211 in order to allow for more rapid decompression and reformation of the seal upon piercing by the spike 26. The seals are advantageously formed form a material which can repeatedly reseal and prevent fluid from flowing around the seal material. The seal 36 should also be capable of being forced down and then spring back into position to reseal the valve. Material that is too soft will reseal effectively; however, will not be capable of springing back after opening of the valve. Material that is too hard will provide sufficient spring force; however, will not effectively seal. Thus, in a preferred embodiment, the seal is formed from a silicone having a hardness in the range from 30–70 Shore durometer units, and more preferably in the range 40–50 Shore durometer units. A cure silicone polymer in the preferred hardness range is available from Wacker Silicone Corp. of Adrian, Mich. Preferably, silicone available from Dow Chemical Co. under the name DOW-595 is used. In some embodiments of the invention, it is desirable to provide additional lubricity to the seal 36 to allow it to spring back and reseal more effectively. Dow Chemical Co. produces a silicon formulation with silicone oil built in to provide this additional lubricity. Preferably, however, X-15™ mineral oil is placed on the seal 36 to lubricate it.

In general, the closing of the valve 10 is provided not by the side wall of the seal 36 which immediately covers the through-holes 34, but by the seal cap 40, or seal cap 92 filling the proximal end of the cavity 98 and the opening 25a. Thus, the seal caps 40 and 92 are sufficiently thick to reseal the opening 25a effectively after valve closure. However, the seal caps 40 and 92 should also be sufficiently thin to allow them to readily return the closed position. Preferably the thickness of the caps 40 and 92 ranges between 0.075 and 0.500 inch and more preferably may be approximately 0.100 inch.

The valve disclosed in this invention can be provided in a sterile and disposable form such that after its use in a given installation is exhausted, the device is discarded. However, as described above, in any given installation, the device can be reused multiple times. Since the device does not employ needles, there is little chance that the device will inadvertently cause skin puncture. Therefore, the extra precautions required for handling and disposing of needles is obviated. It will be apparent from the detailed description provided herein that the present invention can provide for the elimination of nearly all needles used in the medical environment. With the use of the valve of the present invention, the need for all needles except those that are directly input into a patient is, advantageously, eliminated.

Figure 23:
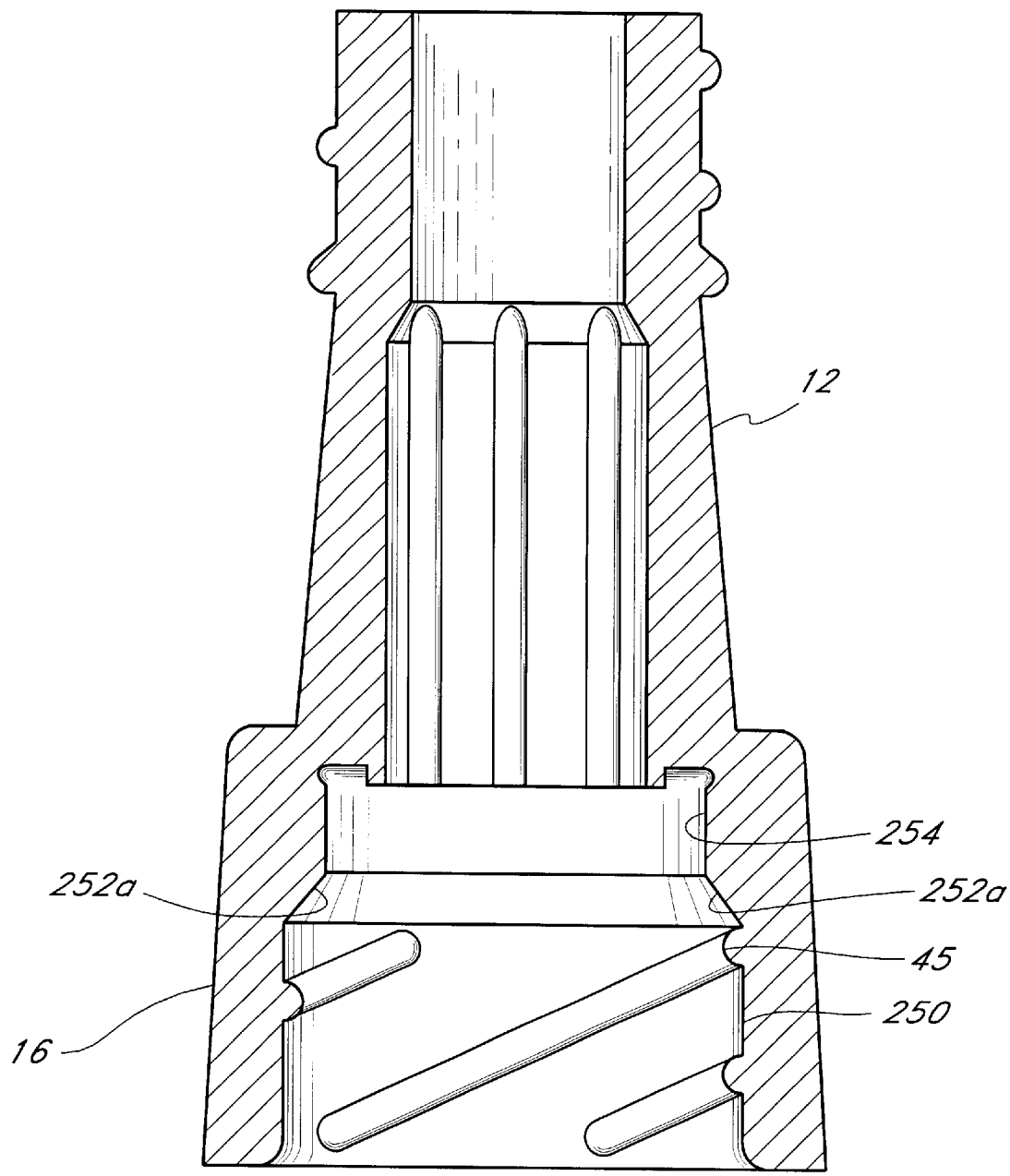
FIG. 23 is a longitudinal cross-sectional view of the body of a tenth embodiment of the valve of this invention, which is suitable for use in a second assembly method.
Figure 24:
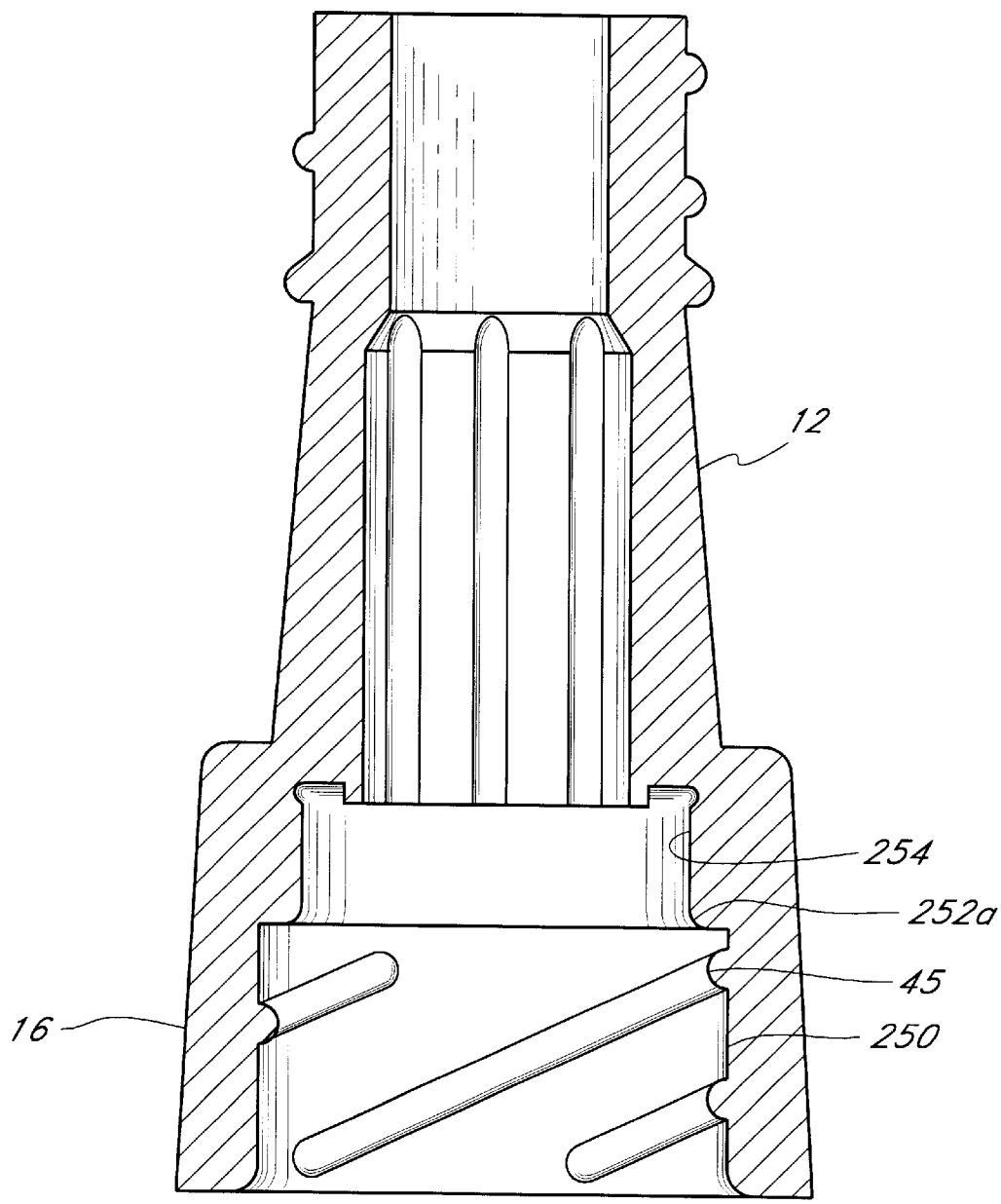
FIG. 24 is a longitudinal cross-sectional view of the body of an eleventh embodiment of the valve of this invention, which is also suitable for use in the second assembly method.

FIG. 23 illustrates a body or housing 12 of a tenth embodiment of the present invention, while FIG. 24 illustrates a body or housing 12 of an eleventh embodiment of the present invention. The housing 12 of FIG. 23 or FIG. 24 is substantially similar to housing 12 described above in conjunction with FIG. 7. Thus, the housing 12 has a bell-shaped skirt 16, an inner surface 254, protruding threads 45, an inner surface 250, and further includes a gouging surface 252a. In FIG. 24 the gouging surface 252a is illustrated as a ledge extending arcuately from the inner surface 250, while in FIG. 23 the gouging surface 252a is illustrated as a ledge extending at a slope from the inner surface 250. The housing 12 is specially designed for use with a second, and improved, method of assembly, described in more detail below. In particular, for the improved method of assembly described below, a portion of the gouging surface 252a preferably has a smaller diameter than the effective diameter of the protruding threads 45. As recognized by a person of skill in the art, other embodiments of the housing 12, with variations to the gouging surface 252a, can be used with the improved method of assembly, or a functionally equivalent method, to provide an improved medical valve 11, based on the following description of the improved valve and method.

Figure 25:
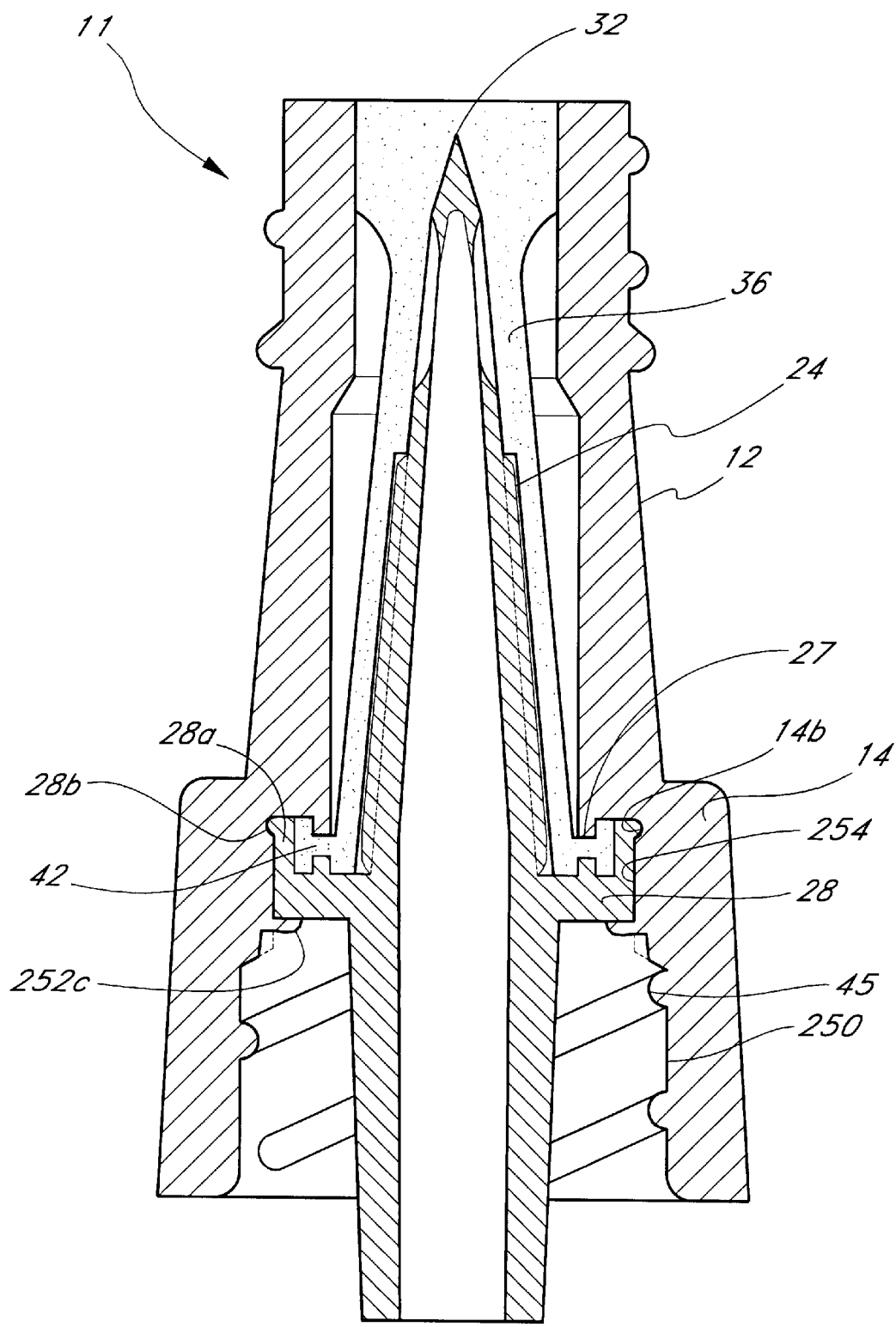
FIG. 25 is a longitudinal cross-sectional view of the tenth embodiment of the valve of the present invention, comprising the spike and seal components from FIG. 3 and the body component from FIG. 23, assembled by using the second assembly method, or a functionally equivalent method.

FIG. 25 illustrates the improved medical valve 11 comprising the housing 12 of FIG. 23 (although the valve 11 could be made with the housing 12 of FIG. 24 equally well), the spike element 24 of FIG. 7, and the seal 36 of FIG. 7. An improved medical valve 11 can also be created from the spike element 24 and seal 36 of any of the first nine embodiments. Thus, for example, an improved medical valve 11 can be assembled using the housing 12 of FIG. 23, the spike element 24 of FIG. 14, and the seal 36d of any of FIGS. 3–7, 7 and 9–19 to create a new, and preferred, embodiment. The improved medical valve 11 is essentially similar to medical valve 10, described above, with the addition of retaining tabs 252c for securing the spike element 24 and the seal 36 inside the housing 12, and a variation in the interference fit between the spike element 24 and the housing 12.

Still referring to FIG. 25, the improved medical valve 11 comprises a spike element 24 and a seal 36 mounted in the housing 12. The seal lip 42 of the seal 36 is secured between the internal lip 27 of the housing 12 and the annular cuff 28 of the spike element 24 to secure the seal 35 inside the housing 12. The annular cuff 28 to the spike element 24 is secured against the underside of the seal lip 42 of the seal 36 by retaining tabs 252c to secure the spike element 24 and the seal 36 inside the housing 12. The retaining tabs 252c preferably consist of a portion of the material that, before assembly, constituted either the gouging surface 252a of FIG. 23 or FIG. 24. These tabs 252c constitute material from the gouging surface 252a which has been gouged away from its original position on the housing 12 and forced against the lower surface of the annular cuff 28. The retaining tabs 252c are rigid enough to hold the spike element 24 and the seal 36 against the underside of the annular ring 14 of the housing 12 and prevent leakage from the improved medical valve 11. The spike element 24 is further prevented from removal from housing 12 because of the annular detent 28b on the annular cuff 28, which detent 28b snaps into the annular groove 14b of the annular ring 14.

The securing force provided by the retaining tabs 252c reduces the need for friction or interference fit between the external portion of annular cuff 28 and the inner surface 254 of annular ring 14, as described above with respect to the first method of assembly. Thus, the outside diameter of the annular cuff 28 can be reduced relative to the inside diameter of the annular ring 14, without allowing leakage to occur within the medical valve 11. For example, it has been found that the outside diameter of the annular cuff 28 can be as little as about 0.003" larger than the inside diameter of the ring 14 and still provide a proper seal. The ability to reduce the diameter of the cuff 28 (in relation to the diameter of the ring 14) reduces the possibility that the housing 12 will crack in response to hoop stress, even when the spike element 24 expands because of the conduction of lipids, or other fats. Further, the lessened importance of providing exact tolerances between the annular cuff 28 and the annular ring 14 allows for variations in the materials and the manufacturing process of these components, reducing manufacturing costs.

Figure 27:
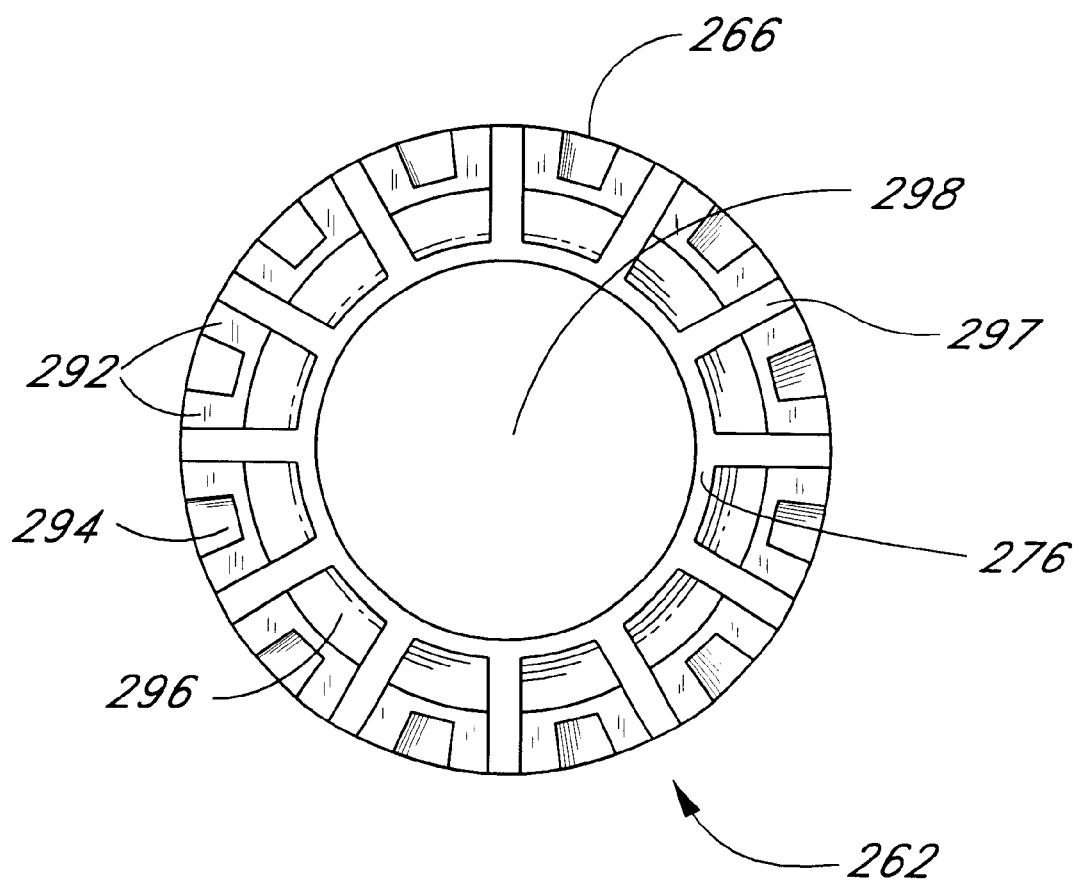
FIG. 27 is a cross-sectional view of the bit of FIG. 26 taken along line 27—27 thereof.

FIG. 26 shows a gouging bit 262 and a base 260 that are preferably used in the improved method of assembling valve 11. The gouging bit 262 has a central bore 298 therethrough, a gouging edge 266 thereon, several guiding surfaces 292, 294, and 296, and a number of ribs 297. The base 260 includes a hole 268. FIG. 27 shows a cross-sectional view of the tip of the gouging bit 262. This figure shows the several guiding surfaces 292, 294, and 296, the ribs 297, along with the bore 298 and a contact surface 276 to which the ribs 297 are connected.

Figure 28:
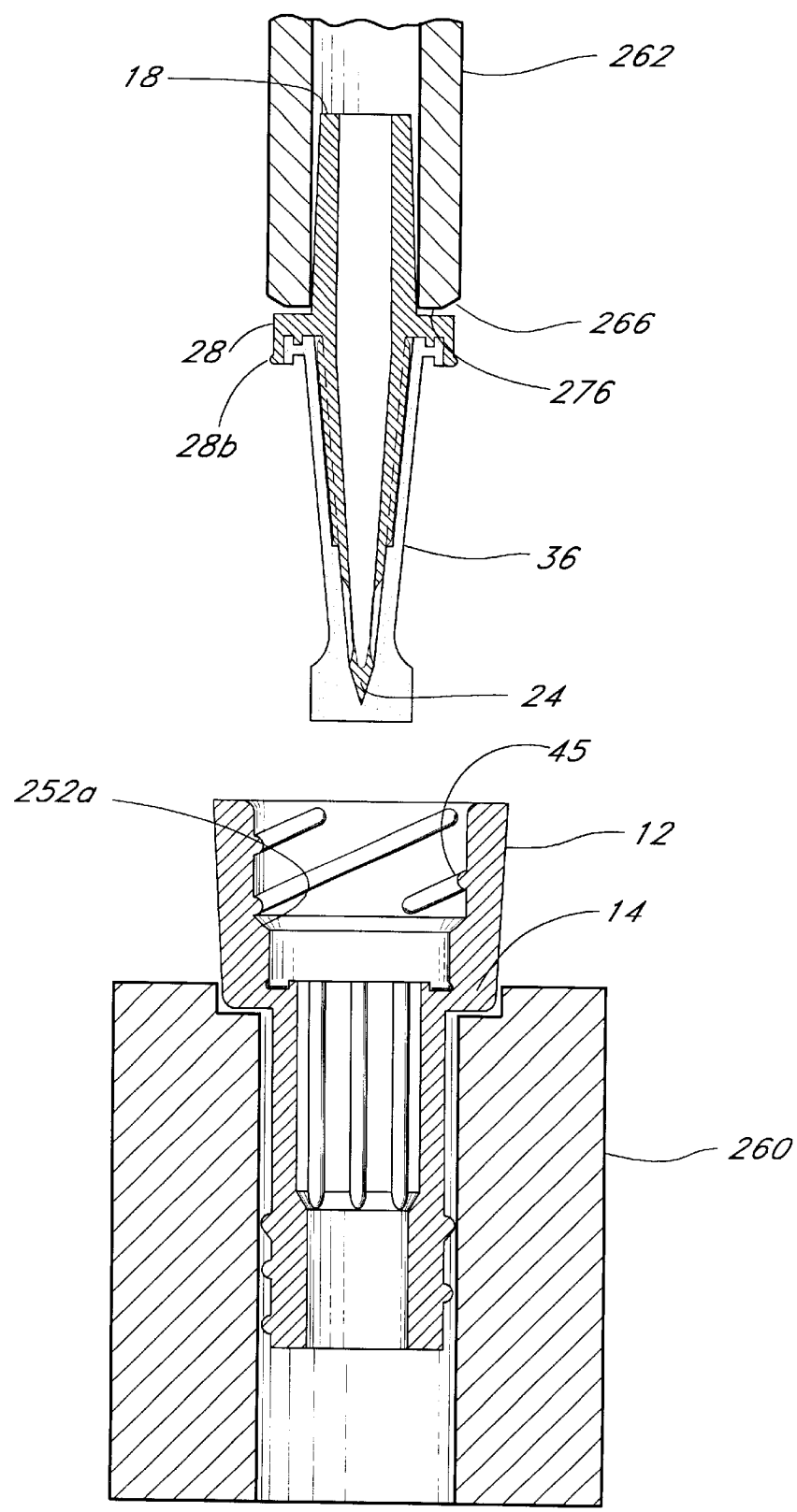
FIG. 28 is a longitudinal cross-sectional view of the components of the assembled valve of FIG. 25, before assembly, inserted with the gouging bit and base of FIG. 26.
Figure 29:
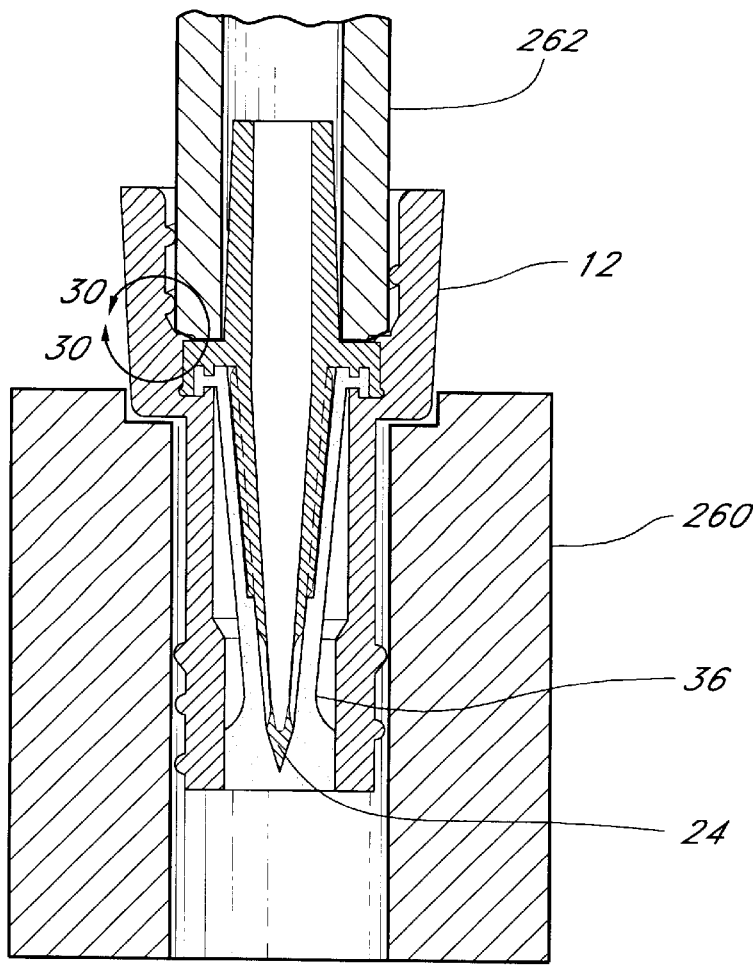
FIG. 29 is a longitudinal cross-sectional view of the assembled valve of FIG. 25, along with the gouging bit and base of FIG. 26.
Figure 30:
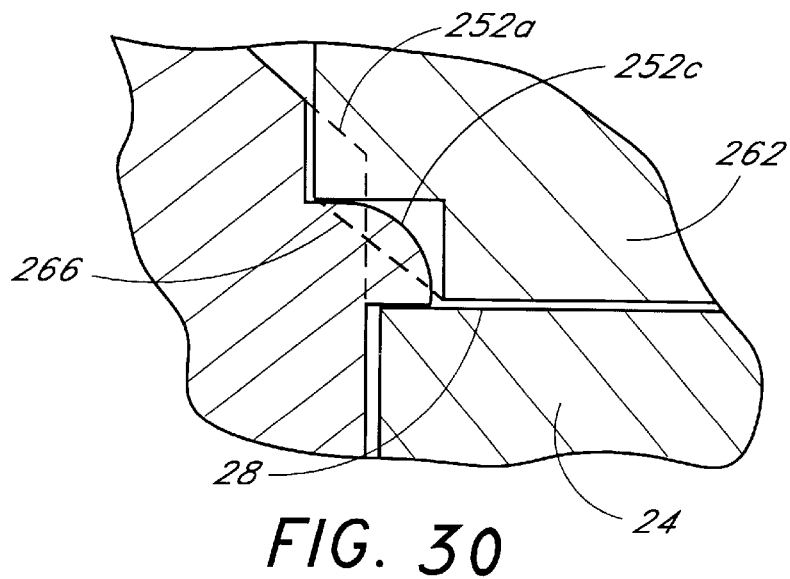
FIG. 30 is an enlarged view of the area inside line 30—30 of FIG. 29.

FIGS. 28, 29, and 30 illustrate the use of the gouging bit 262 and the base 260 to perform the improved method to assemble an improved valve 11 of the present invention. Referring to FIG. 28, a seal 36 of FIG. 7 is placed onto a spike element 24 of FIG. 7. The inner conduit 18 of the spike element 24 is placed inside the bore 298 in the gouging bit 262. The spike element 24 can be retained inside the gouging bit 262 by friction between the outer surface of the inner conduit 18 of the spike element 24 and the inner surface of the bore 298 of the gouging bit 262, or by other appropriate means.

Preferably, the contact surface 276 of the gouging bit 262 contacts the upper surface of the annular cuff 28 of the spike element 24. It is noted that the gouging bit 262 is sized such that the gouging edge 266 extends beyond the outside perimeter of the spike element 24, including the annular detent 28b.

The valve housing 12 is placed inside of the hole 268 located in the base 260, with the distal end of the housing 111 protruding from the base 260. Once the gouging bit 262 and the base 260 are positioned so that their centers are in direct vertical alignment, the base 260 is moved upwardly, toward the gouging bit 262 (although, as one skilled in the art will recognize, alternately, the bit 262 may be moved downwardly towards the base 260). As the base 260 approaches the gouging bit 262, the base 260 forces the housing 12 around the outside of the spike element 24 and the seal 36, so that the spike element 24 and the seal 36 penetrates the housing 12. Continued movement of the base 260 causes the housing 12 to be pushed up around the spike element 24 and the seal 36 until the distal portion of the annular ring 14 of the housing 12 makes contact with the annular cuff 28 of the spike element 24, as shown in FIG. 29.

Referring again to FIG. 28, the inside diameter of the housing 12 including the threads 45) is sufficiently large enough that when the housing 12 is pressed around the outside of the spike element 24 and the seal 36, the annular detent 28b of the spike element 24 passes by the protruding threads 45 and the gouging surface 252a of the housing. Further, the inside diameter of the housing 12 is sized such that the gouging edge 266 of the gouging bit 262 also do not contact the threads 45.

However, the housing 12 and bit 262 are sized such that the gouging edge 266 of the gouging bit 262 does make contact with the housing 12 at the gouging surface 252a. In this manner, the gouging edge 266 of the gouging bit 262 gouges a portion of the gouging surface 252a away from the inner surface of the housing 12. The portion of the gouging surface 252a that is partially separated from the housing 12 is folded or crushed in towards the center of the gouging bit 262 and down toward the annular cuff 28 of the spike element 24 between pairs of ribs 297 by the guiding surfaces 292, 294, 296 to form a number of retaining tabs 252c, as shown in FIGS. 29 and 30. At this point, the housing 12, the spike element 24, and the seal 36 have been assembled to form an improved medical valve 11, with the retaining tabs 252c securing the spike element 24 and the seal 36 inside the housing 12. The gouging bit 262 can then be separated from the base 260, and the assembled medical valve 11 can be removed.

The method described above is the preferred method of assembly for the improved medical valve 11 of the present invention. However, this improved method of assembly can be modified in numerous ways without departing from the essential teachings of the present invention.

Referring again to FIGS. 26 and 27, the tip of the gouging bit 262 comprises a number of surfaces 276, 266 and 292, 294, and 296 that combine to perform three basic functions. First, the contact surface 276, which is preferably an annular surface having a diameter of less than the outer diameter of the bit 262, presses against the annular cuff 28 of a spike element 24 to drive the spike element 24 into the housing 12. Second, the gouging surface 266 on the gouging bit 262 scrapes a portion of the gouging surface 252a of the housing 12 away from the remainder of the gouging surface. Specifically, gouging surface 266 is created by the intersection of surfaces 292 and 294 of the gouging bit 262 with the outside surface 291 of the gouging bit 262 to form a relatively sharp edge at the perimeter of the gouging bit 262. Third, the gouging bit 262 folds the gouged material from the gouging surface toward the center of the gouging bit 262 along surfaces 292, 294, and 296. In order to perform this guiding function, surfaces 292, 294 and 296 all preferably slope downwardly and inwardly towards the contact surface 276. Further, in order to create thick retaining tabs as opposed to a thinner retaining ring, ribs 297 are used to guide and separate the gouged material. Each rib 297 thus partially extends from the gouging edge 266 to the guiding surface 276. As illustrated, 112 ribs 297 are advantageously used to create 112 tabs.

FIGS. 26 and 27 illustrate the presently preferred embodiment of the gouging bit 262. However, a person of skill in the art can modify the design of the gouging bit 262 in numerous ways without departing from the teachings of the present invention.

Figure 31:
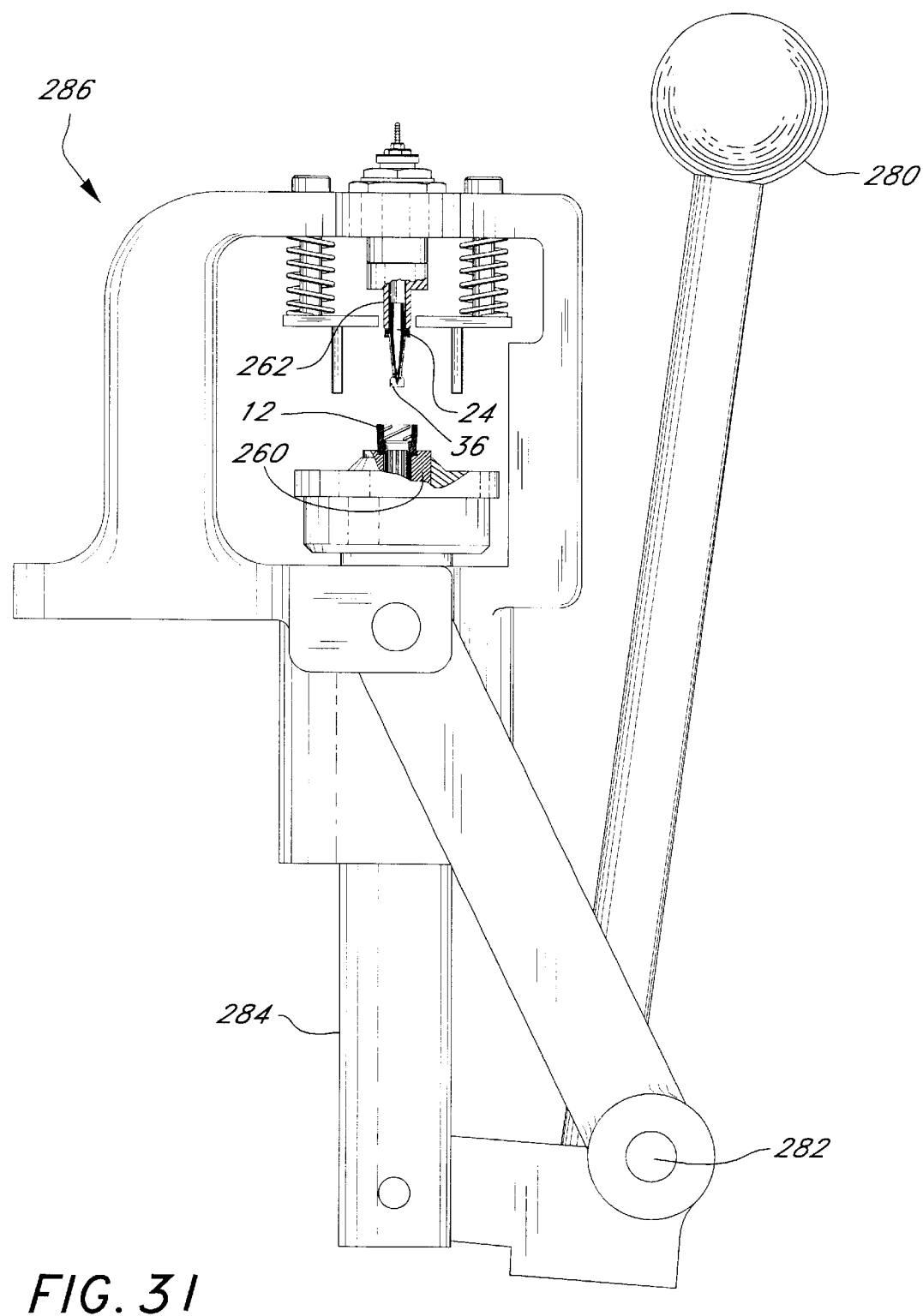
FIG. 31 illustrates a partial cross-sectional view of a manually operated punch machine for using the gouging bit and base of FIG. 26 to perform the second assembly method on the valve components shown as illustrated in FIG. 28.

Substantial force is required to drive the base 260 toward the gouging bit 262 with sufficient force to insert the spike element 24 into the housing 12 and to gouge the gouging surface 252a of the housing 12 and create the retaining tabs 252c. Preferably, therefore, this assembly is accomplished through use of a machine 286. FIG. 31 illustrates the manually operated punch machine 296 that is preferably utilized, along with the gouging bit 262 and the base 260, to perform the improved method of assembly. The punch machine 286 illustrated in FIG. 31 is well-known to a person of skill in the art, and merely incorporates the specific bit 262 and base 260 described above. When utilizing this machine 286, the gouging bit 262 is positioned in the punch machine 286 so that it is in direct vertical alignment with the base 260. Again, the seal 36 is placed over the spike element 24, which is placed inside the gouging bit 262. The value housing 12 is placed inside the base 260. The punch machine 286 is operated by manually pulling down on a handle 280 to create rotational motion in an axle 282, which in turn creates vertical motion in a piston 284. The vertical motion of the piston 284 is then communicated to the base 260. Thus, by this machine 286, a downward motion in the handle 280 is translated into an upward motion in the base 260 with respect to a stationary bit 262.

Movement of the piston 284 pushes the base 260 in which the valve housing 12 is located upwardly until the annular cuff 28 of the spike element 24 contacts the annular ring 14 of the housing 12. During this procedure, the gouging edge 266 of the gouging bit 262 gouges a portion of the gouging surface 252a away from the inner surface of the housing 12 to create the retaining tabs 252c. A mechanical stop (not shown) is preferably used to prevent the base 260 from being driven too far relative to the gouging bit 262.

After the components of the medical valve have been assembled, the handle 280 is released and returned to its normal position as shown in FIG. 31. At this time, the base 260 also returns to its normal position, also known in FIG. 31. The completed valve 11 is then removed from the machine 286.

Although FIG. 31 illustrates a manually-operated punch machine, a person of skill in the art will recognize that a wide variety of machines could be designed to implement the improved method of assembly, including an automated version of the machine 286 described above.

The valve 10 or 11 is used to provide a closed, patient access system for transferring a predetermined amount of medication from a remote source to the patient. The valve 10 or 11 is connected by the distal end to the patient, for example, a vein or artery in fluid communication with the valve. Blood fills the valve, but the seal 36d, for example, prevents any blood from leaking from the valve. The delivery end or nose 28 of the medical implement (such as syringe 22) is inserted into the valve as depicted in FIG. 8, pushing the nose 28 against the seal to compress the seal sufficiently to allow the tip 32 of the spike 24 to pierce the seal and enter said delivery end. The predetermined amount of medication in its entirety may now be transferred through the nose 28 into the valve 10 or 11 and into the patient. Since the nose 28 and seal 36d engage in a manner so that the tip 32 of the spike element 24, upon piercing the seal, meets the seal to avoid formation of any dead space at the interface between nose 28 and the seal surface 40b. Transfer directly through the valve 10 or 11 of essentially the entire predetermined amount of medication from the syringe 22 to the patient, so that essentially none of said predetermined amount is collected in any dead space in the valve, is accomplished with this invention. Upon withdrawing the nose 28 from the valve 10 or 11 the seal 36d returns to the decompressed state to close the valve and maintain while in said decompressed state a fluid tight seal even at high pressure and after repeated uses.

FIG. 32 illustrates the piercing element 520 used in conjunction with the above-described valve 10 or 11. It is recognized that the piercing element 520 may be used in conjunction with any of the embodiments of the valve 10 or 11 described above.

In particular, in the preferred embodiment, the proximal end 570 of the piercing element 520 has a number of threads 588 located on the outside surface thereof for engagement with the threads 45 inside of the housing 12 of valve 10 or 11. These threads 588 may comprise standard threads, or, as shown, short wings for engaging the threads 45 of the housing 12. When the proximal end 570 of the piercing element 520 is threadingly engaged with the distal end of the valve 10 or 11, the valve 10 or 11 and piercing element 520 form a fluid tight seal.

It is also contemplated that the piercing element 520 and valve 10 or 11 may be made as a single element, wherein the conduit 18 of the valve 10 or 11 and the connection portion at the proximal end 570 of the piercing element 520 comprise a continuous single conduit or element. In one version the piercing element 520 (without threads thereon) may be connected to the conduit 18 of the valve 10 or 11 and be permanently affixed thereto. This may be done, for example, by fusing the conduit 18 into the connecting portion of the piercing element or by any other means known to one skilled in the art. Alternatively, the spike 24 may be formed as an extension of the proximal end 570 of the piercing element 520.

Method of Using the Alternate Embodiment

In operation, the piercing element 520 is preferably threaded into engagement with the housing 12 of the valve 10 or 11. The penetrating portion 532 of the piercing element 520 is then inserted through the septum 534 of the vial 524. Lastly, as best illustrated in FIGS. 6 and 7, the nose 28 of the syringe 22 is engaged with the proximal end of the valve 10 or 11. Once the syringe 22 is engaged, a fluid conduit exists from the vial 524 through the piercing element 520 and valve 10 or 11 to the syringe 22, whereby fluid may be withdrawn into the syringe 22 from the vial 524.

Advantageously, the syringe 22 may be disengaged from the valve 10 or 11 at any time. Once disengaged, the fluid conduit is automatically closed by the seal 36 in the valve 10 or 11. This system allows later withdrawal of fluid with another syringe 22, without the fear of contamination of the fluid in the vial between uses.

Drip Bag Adaptor

Figure 33:
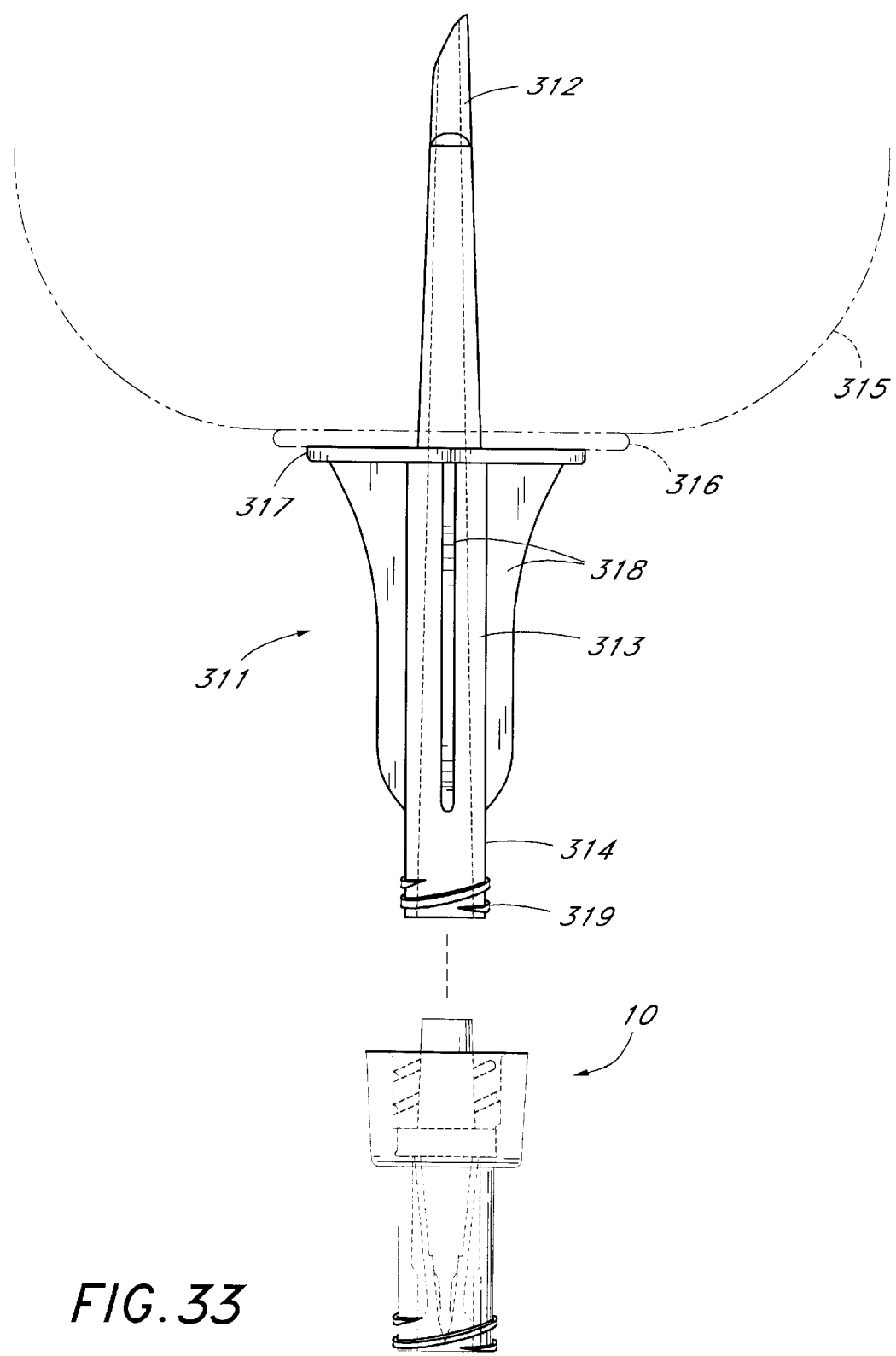
FIG. 33 is a partially exploded side view of one embodiment of a drip bag adaptor made in accordance with the present invention, showing the relationship between the drip bag, adaptor, and removable valve.
Figure 34:
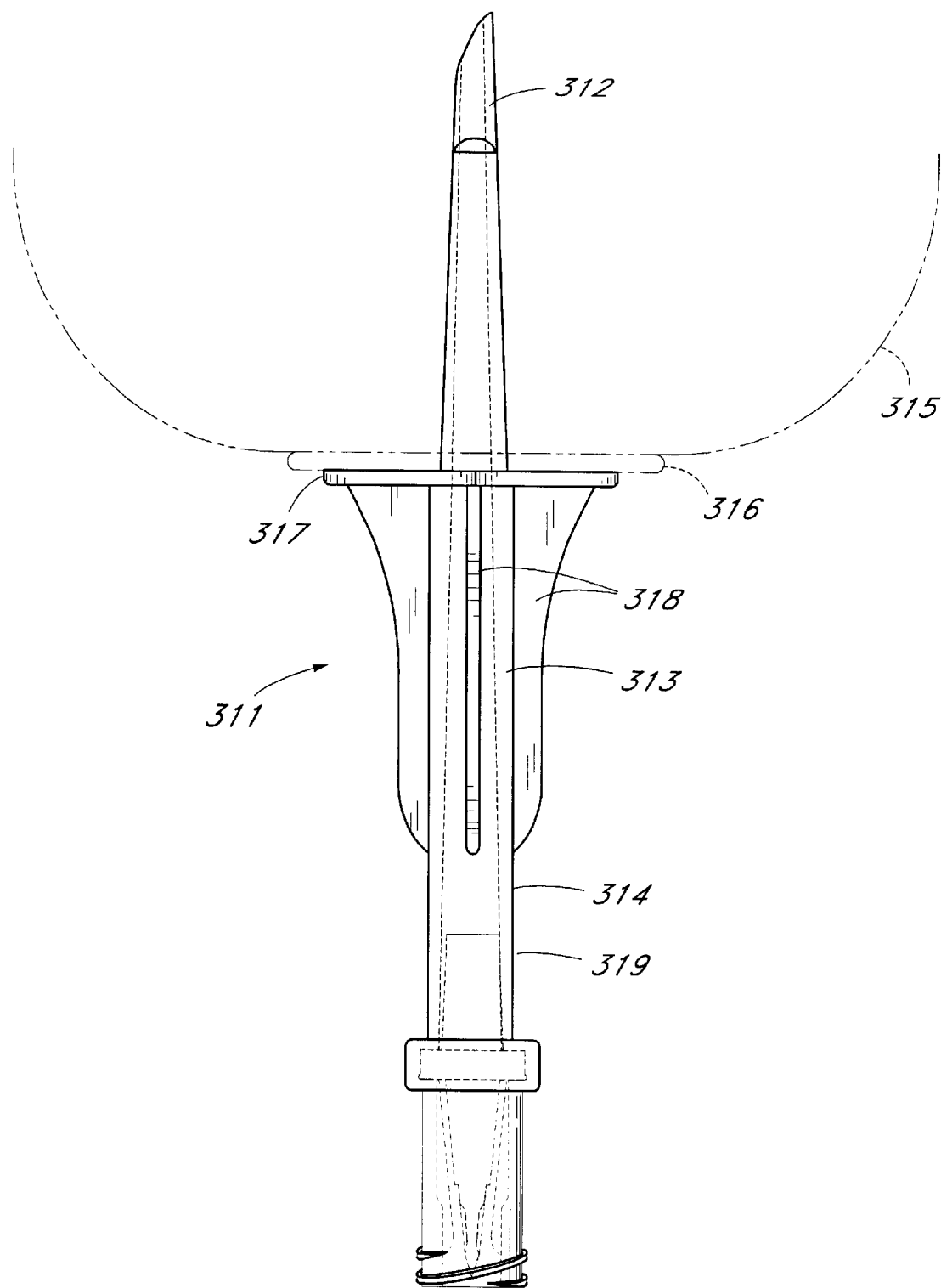
FIG. 34 is a side view of another embodiment of the drip bag adaptor, having an integral valve.

In another preferred embodiment of the invention, illustrated by FIGS. 33 and 34, a sterile adaptor 311 is provided to function as a connector to a container 315 (shown in phantom) of fluid. Fluid can thus be removed from or added to the fluid container.

The adaptor 311 is preferably made of any medically inert material. In a preferred embodiment of the adaptor 311, and especially where disposability is desired, the adaptor 311 is constructed of rigid plastic. In other embodiments, however, and particularly where reusability is desired, the adaptor 311 may be made of stainless steel or any other medically inert substance, to allow sterilization in an autoclave or similar device.

FIG. 33 shows an adaptor 311 having a generally cylindrical body 314 with a proximal end and a distal end, and an adaptor spike 312 located at the proximal end. The adaptor spike 312 will preferably penetrate the outer surface of a seal 316 located on the container 315. The spike 312 may be of any size and shape, to accommodate a range of container and seal sizes. In a preferred embodiment of the adaptor 311, shown in FIG. 33, the spike 312 is generally cylindrical having a sharpened annular proximal end, and is approximately 1.375 inches long. Alternatively, the spike 312 may be generally frustoconical in shape.

A longitudinal channel 313 leads from the proximal end of the spike to the distal end of the adaptor 311, providing a route for fluid to flow through the adaptor 311. The channel 313 is typically cylindrical although it may also be slightly frustoconical to accommodate the change in diameter from the tip to the spike 311 to the distal end of the adaptor 311. In the preferred embodiment of the adaptor 311, the channel 313 has a generally smooth interior surface, to facilitate the easy flow of fluid through the adaptor 311.

Near the distal end of the spike is preferably located a flange 317, of a size and shape to sealably conform to the surface of the seal 316. In this manner, the spike 312 and flange 317 serve to first penetrate the seal 316 and next mate with the seal 316, preventing leakage of fluid from the container 315 around the outside surface of the adaptor 311. In addition, the flange 317 prevents the adaptor 311 from entirely transversing the seal 316.

In one embodiment, shown in FIG. 33, strengthening ribs 318 are provided between the distal end of the adaptor 311 and the flange 317. These ribs 318 provide rigidity to the body 314 and prevent unwanted bending or twisting of the adaptor 311. In addition, the ribs 318 provide a gripping surface for the fingers or hand of a user, facilitating easy insertion or removal of the adaptor 311 through the seal 316. In other embodiments, however, strengthening ribs 318 may not be required. This is particularly so where the length of the body 314 is relatively small.

The body 314 may be of any length necessary to accommodate easy connection to the fluid container 315. In particular, it is advantageous that the body 314 be long enough to provide the user an adequate gripping surface, to facilitate installation and removal of the adaptor 311. In a preferred embodiment of the adaptor 311, the body 314 is approximately 1.625 inches long.

In one preferred embodiment of the adaptor 311, shown in FIG. 33, the distal end of the adaptor 311 is provided with a locking mechanism 319 that preferably comprises a Leur-Lock device or other locking device known to those of skill in the art. The locking mechanism 319 is adapted to removably and sealably connect the distal end of the adaptor 311 to a medical valve 10 or 11 as previously described.

Alternatively, as shown in FIG. 34, the distal end of the adaptor 311 can be provided with an integral medical valve 10 or 11.

The adaptor 311 is thus useable with containers having a seal. Examples of containers with such seals contemplated for use with this invention include medicament drip bags, bottles for intravenous delivery of fluids, or the like.

In use, the adaptor 311 coupled with a valve 10 or 11 is typically inserted into a medicament drip bag or the like. Thereafter, the tip or nose of an ANSI standard IV set, syringe, or other connector or medical implement, is then pushed into the proximal end of the medical valve 10 or 11. Referring now to FIGS. 6 and 7, this action pushes the tip 32 of the spike 26 through the seal 36, exposing the through holes 34 and thus bringing the IV tubing or other medical implement into fluid communication with the fluid in the bag 315. The connection process is more extensively described above with reference to FIGS. 6 and 7.

Y-Connector with Integral Valve

Figure 35:
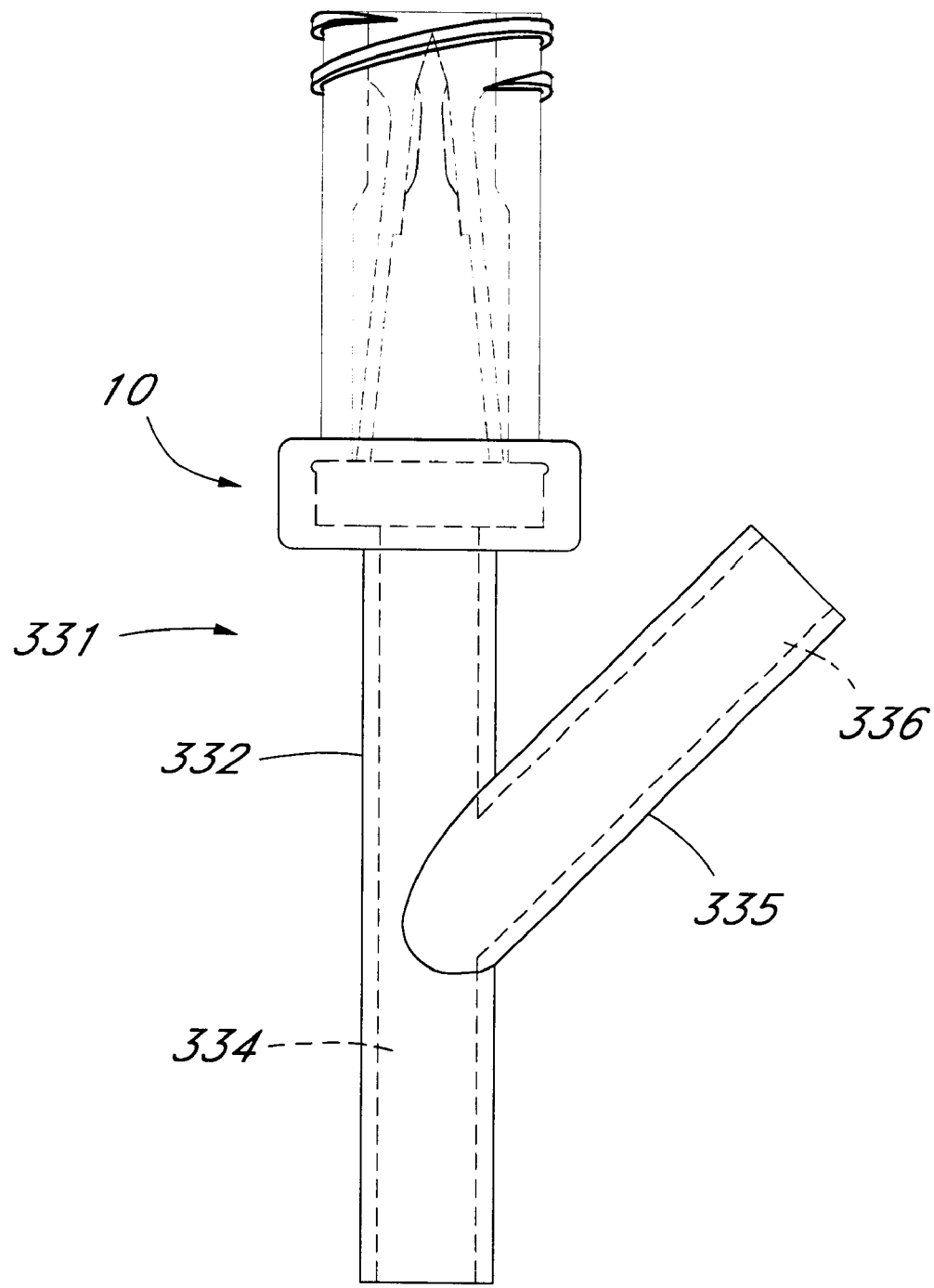
FIG. 35 is a side view of a new Y-site or piggyback y-connector made in accordance with the present invention.

Another embodiment of the present invention is shown in FIG. 35. A connector 331 is provided to function as a conduit between either two or three fluid sources or receptacles. The connector 331 has a tubular body 332, having a proximal and a distal end, and a tubular branch 335 located between the proximal and distal ends. At the proximal end of the body 332 is provided an integral spike element 24 as previously described.

The connector 331 is preferably made of any medically inert material. Advantageously, the connector 331 may be made of a transparent material, allowing a user to see whether fluid is flowing therethrough. In one preferred embodiment of the connector 331, and especially where disposability is desired, the connector is constructed of rigid transparent plastic.

A longitudinal channel 334 runs through the body 332 from the proximal end to the distal end, providing continuous fluid communication from the through holes 34 of the spike element 24 through the connector 331. The channel 334 is generally cylindrical in shape, although it may be slightly conical or have internal step changes in diameter to accommodate the difference in diameter between the base of the spike element 24 and the distal end of the body 332. Furthermore, in the preferred embodiment of the connector 331 the channel 334 has a generally smooth interior surface, to facilitate the flow of fluid through the connector 331.

Toward the proximal end of the body 332 is provided the tubular branch port 335, which has a longitudinal channel 336 located therethrough. The channel 336 is in fluid communication with the channel 334 of the main body 334, and is, like the main channel 334, generally cylindrical in shape. In addition, the channel 336 preferably has a generally smooth interior surface.

The spike element 24 is preferably formed integrally with the main body 332. To form a plastic body with a continuous through-channel (such as the body 332 of this connector 331), an effective method of manufacture is to use a bore pin to manufacture the connector 331. The connector 331 of the present invention has the advantage of easy manufacture at low cost. In addition, the connector 331 will be less bulky, and will have a lower weight, than a connector in which the spike element 24 is formed separately and then mechanically attached.

At a later time, before use, the seal 36 and housing 12 of the medical valve 10 or 11 of other preferred embodiments can be placed over the spike element 24 and attached by such means as were described earlier in the discussion of those embodiments.

In use, the distal end of the body 332 can be placed in fluid communication with flexible tubing (not shown) or another fluid transmitting device or medical implement. The end of the branch port 335 can be, like the distal end of the body 332, placed in fluid communication with a source of fluid or other fluid transmitting device or medical implement.

The connector 331 typically connects one or two fluid sources with a fluid receiver such as a patient. A first fluid source or parenteral fluid is, in use, placed in fluid communication with the tubular branch port 335. The fluid receiver, such as a patient, is, in use, placed in fluid communication with the distal end of the body 332. In this manner, the first fluid flows from its source through the branch port channel 336 into the main channel 334 and then to the fluid-receiver or patient.

When a second fluid needs to be administered to a patient, the tip or nose of an ANSI standard syringe or other medical implement is pushed into the end of the medical valve 10 or 11. Referring now to FIGS. 6 and 7, this action pushes the tip 32 of the spike 26 through the seal 36, exposing the through holes 34 and thus bringing the syringe or other connector into fluid communication with the connector 331. The connection process is more extensively described above with reference to FIGS. 6 and 7. Once the second fluid has been introduced the y-connector (also known as a y-site or piggyback connector) can be disconnected and the seal closes the valve 10 or 11.

Hook Adaptor for Y-Connectors

FIGS. 36, 37, and 38 illustrate another embodiment of the present invention. A hook adaptor 351 is provided to function as a connector to a standard piggyback or y-site (not shown). The hook adaptor 351 attaches to the piggyback or y-site, providing a stable fluid link to the piggyback or y-site that is not easily or accidentally disconnected.

The hook adaptor 351 is preferably made of any medically inert material. In a preferred embodiment of the hook adaptor 351, and especially where disposability is desired, the hook adaptor 351 is constructed of rigid plastic. In other embodiments, however, and particularly where reusability is desired, the hook adaptor 351 may be made of stainless steel or any like substance, to allow sterilization in an autoclave or similar device.

As shown in FIG. 36, the hook adaptor 351 has a generally cylindrical tubular body 354 with a proximal end and a distal end, with an adaptor housing 355 and spike 358 at or near the distal end. In addition, a hook 357 leads downward and away from the housing 355, to rotatably and removably engage an arm of the y-axis when the hook adaptor 351 is placed in fluid communication with the y-site, thereby providing a stable and not easily disconnected link.

Referring to FIG. 36, the housing 355 has a depth, defined by the distance from the distal end of the outside wall 358 of the housing 355 to the base 359 of the housing 355, sufficient to envelop a substantial portion of the end of the branch port of the piggyback or y-site connector. In the preferred embodiment of this adaptor 351, the housing 355 is approximately 0.375" deep.

The housing 355 may furthermore have a section 352 removed from a portion of the distal end of the housing wall 358, to accommodate the arm of the piggyback connector when the adaptor 351 is in the connected and locked position (see discussion below).

Centrally located within the housing 355 is a spike 356. The spike 356 is tubular, having a narrow channel 353 running longitudinally therethrough, providing a route for fluid to flow through the spike 356 and into the body 354 of the adaptor 351. The spike 356 will preferably penetrate a septum located on the end of the branch port. The spike 356 may be of any length and shape, to accommodate a range of septum sizes. Most advantageously, the spike is approximately as long as, or smaller than, the depth of the housing 355, so that the end of the spike does not substantially protrude beyond the distal end 358 of the housing 355. This prevents a user from accidentally sticking himself or herself with the spike 356. In a preferred embodiment of the adaptor 351, shown in FIG. 36, the spike 356 is generally cylindrical having a sharpened annular proximal end, and is approximately 0.37 inches long. Alternatively, the spike 356 may be generally frustoconical in shape.

The spike 356 should furthermore be smooth surfaced, and as thin as possible to avoid substantially rupturing or coring of the septum of the branch port of the piggyback connector during insertion and/or removal, yet large enough to provide a sufficient channel 353 for fluids, especially liquids, to pass easily therethrough. In particular, it is contemplated that the adaptor 351 may be repeatedly connected to, and removed from, the same connector.

The longitudinal channel 353 is typically cylindrical although it may also be slightly frustoconical to accommodate the change in diameter from the tip of the spike 356 to the base 359 of the housing 355. In the preferred embodiment of the adaptor 351, the channel 353 has a generally smooth interior surface, to facilitate the easy flow of fluid through the adaptor 351.

The body 354 may be of any length necessary to accommodate easy connection to the piggyback connector. In particular, it is advantageous that the body 354 be long enough to provide the user an adequate gripping surface, to facilitate installation and removal of the adaptor 351. In a preferred embodiment of the adaptor 351, the body 354 is approximately 0.41 inches long, measured from the base 359 of the housing 355 to the proximal end of the body 354.

In one preferred embodiment of the adaptor 351, shown in FIG. 36, the proximal end of the adaptor 351 is provided with a locking mechanism 360 that preferably comprises a Luer-Lock device or other locking device known to those of skill in the art. The locking mechanism 360 is adapted to removably and sealably connect the proximal end of the adaptor 351 to a medical valve 10 or 11 as previously described.

Alternatively, as shown in FIG. 38, the proximal end of the adaptor 351 could be provided with an integral medical valve 10 or 11.

The hook 357 is of a size and shape to rotatably engage an arm of the y-site. The hook 357 preferably leads downward from the housing 355 at a slight angle, to accommodate the angle at which the branch port departs from the main body or arm of the y-site. In the preferred embodiment of the adaptor 351 shown in FIGS. 36 and 38, the hook 357 declines from the housing 355 at an angle of approximately 27°, and is approximately 0.5 inches long. The interior bend of the hook 357 should be of a radius to accommodate the arm of the y-site, and is the shown preferred embodiment approximately 0.11 inches in radius.

In use, the housing 355 of the adaptor 351 is placed over the end of the branch port of the y-site, and then pressed down until the spike 356 penetrates the septum on the branch port, providing fluid communication between the adaptor 351 and the y-site. The adaptor 351 is then rotated until the hook 357 engages the arm of the y-site, firmly holding the adaptor 351 onto the y-site and preventing accidental disconnection to the adaptor 351. To remove the adaptor 351, a user merely rotates the hook 357 in the opposite direction, disengaging the hook 357 from the y-site.

If using an adaptor 351 of the type shown in FIG. 36, a medical value 10 or 11 of the first preferred embodiment can be attached to the proximal end of the adaptor 351, using the locking mechanism 360.

The tip or nose of an ANSI standard IV set, syringe, or other connector or medical implement, is then pushed into the proximal end of the medical valve 10 or 11. Referring now to FIGS. 6 and 7, this action pushes the tip 32 of the spike 26 through the seal 36, exposing the through holes 34 and thus bringing the syringe or other connector into fluid communication with the adaptor 351. The connection process is more extensively described above with reference to FIGS. 6 and 7.

Snap-On Adaptor for Piggyback Connector

Another embodiment of the present invention is shown in FIGS. 39, 40, and 41. A snap-on adaptor 371 is provided to function as a connector to a standard medical y-site. The snap-on adaptor 371 attaches to the branch port or another arm of the y-site, providing a stable fluid link to the y-connector 361 that is not easily or accidentally disconnected.

The snap-on adaptor 371 is preferably made of any sterile, medically inert material. In addition, the material should be capable of slight elastic deformation, to allow the adaptor 371 to "snap" into position (see description of use, below). In the preferred embodiment of the snap-on adaptor 371, and especially where disposability is desired, the adaptor 371 is constructed of rigid plastic. In other embodiments, however, and particularly where reusability is desired, the adaptor 371 may be made of stainless steel or any like substance, to allow sterilization in an autoclave or similar device.

As shown in FIG. 39, the snap-on adaptor 371 has a generally cylindrical tubular body 374 with a proximal end and a distal end, and an adaptor housing 375 and spike 376 at the distal end.

The adaptor housing 375 is generally cylindrical and of a size and shape to closely surround the end of the branch port or other arm of the standard y-site. The housing 375 wall has an opening 372, shaped to closely accommodate the branch port or arm of the piggyback connector when the adaptor 371 is connected to the y-site.

The opening 372 is preferably just wide enough to allow the branch port of arm of the y-site to pass easily therethrough. In addition, in the preferred embodiment of the adaptor 371 as shown in FIG. 39, the opening 372 has a rounded proximal end, to accommodate the radius of the protruding branch port of arm of the y-site when the adaptor 371 is connected to the y-site. In a preferred embodiment of the adaptor 371, the opening 372 is approximately 0.22 inches wide, and rounded at one end with a 0.11 inch radius.

Toward the distal end 378 of the housing 375, the opening 372 narrows sharply and then gradually widens, so that a pair of opposing and spaced apart tabs 377a, 377b are formed, integral with the housing 375. The tabs 377a, 377b are spaced apart a distance sufficient to prevent the passage of the branch port or arm of the y-site therethrough, unless deliberate pressure is applied. In the preferred embodiment of the adaptor 371, the tabs 377a, 377b are spaced apart by approximately 0.09 inches.

The opening 372 gradually widens from the tabs 377a, 377b toward the distal end of the housing wall 378, thus providing entrance bearing surfaces 373a, 373b which assist in guiding an arm of the y-site into the opening 372. In the preferred embodiment of the adaptor 371 shown in FIGS. 39 and 41, the entrance bearing surfaces 373a, 373b decline from the horizontal at an angle of approximately 40°.

Centrally located within the housing 375 is the spike 376. The spike 376 is tubular, having a narrow channel 381 running longitudinally therethrough, providing a route for fluid to flow through the spike 376 and into the body 374 of the adaptor 371. The spike 376 will preferably penetrate a septum located on a branch port of a y-site. The spike 376 may be of any length and shape, to accommodate a range of seal sizes. Most advantageously, the spike does not protrude past the distal end of the housing 375. This prevents a user from accidentally sticking himself or herself with the spike 376. In a preferred embodiment of the adaptor 371, shown in FIG. 39, the spike 376 is generally cylindrical having a sharpened annular proximal end, and is approximately 0.5 inches long. Alternatively, the spike 376 may be generally frustoconical in shape.

The spike 376 should furthermore be smooth surfaced, and as thin as possible to avoid substantially rupturing the septum on the branch port of the piggyback connector during insertion and/or removal, yet large enough to provide a sufficient channel 381 for fluids, especially liquids, to pass easily therethrough. In particular, it is contemplated that the adaptor 371 may be repeatedly connected to, and removed from, the same y-site, potentially tearing small pieces of the septum off in the process. This poses the danger of causing particles of the septum to enter the fluid stream of the y-site, contaminating the stream and possibly harming a patient. Therefore, in the preferred embodiment of the adaptors 371, the spike 376 is only about 0.05 inches in diameter.

The longitudinal channel 381 is typically cylindrical although it may also be slightly frustoconical to accommodate the change in diameter from the tip of the spike 376 to the base 379 of the housing 375. In a preferred embodiment of the adaptor 371, the channel 381 has a generally smooth interior surface, to facilitate the easy flow of fluid through the adaptor 371.

The body 374 may be of any length necessary to accommodate easy connection to the y-site. In particular, it is advantageous that the body 374 be long enough to provide the user an adequate gripping surface, to facilitate installation and removal of the adaptor 371. In the preferred embodiment of the adaptor 371, the body 374 is approximately 0.3 inches long, measured from the base 379 of the housing 375 to the proximal end of the body 374.

In one preferred embodiment of the adaptor 371, shown in FIG. 39, the proximal end of the adaptor 371 is provided with a locking mechanism 382 that preferably comprises a Leur-Lock device or other locking device known to those of skill in the art. The locking mechanism 382 is adapted to removably and sealably connect the proximal end of the adaptor 371 to a medical valve 10 or 11, as previously described.

Alternatively, as shown in FIG. 41, the proximal end of the adaptor 371 could be provided with an integral medical valve 10 or 11.

In use, the housing 375 of the adaptor 371 is placed over the end of the branch port of the y-site, and then advanced so that the spike 376 pierces the septum on the branch port. A deliberate force must be applied so that the arm of the y-site passes through the tabs 377a, 377b and into the opening 372. Constant pressure on the adaptor 371 thus causes the arm of the y-site to snap into the opening, and contemporaneously the spike 376 penetrates the septum, providing fluid communication between the y-site and adaptor 371.

To remove the adaptor 371, the user must deliberately pull the adaptor 371 off the y-site.

If using an adaptor 371 of the type shown in FIG. 39, a medical valve 10 or 11 of the first preferred embodiment may be attached to the proximal end of the band adaptor 371, using the locking mechanism 382.

The tip or nose of an ANSI standard IV set, syringe, or other connector, is then pushed into the proximal end of the medical valve 10 or 11. Referring now to FIGS. 6 and 7, this action pushes the tip 32 of the spike 26 through the seal 36, exposing the through holes 34 and thus bringing the syringe or other connector into fluid communication with the adaptor 371. The connection process is more extensively described above with reference to FIGS. 6 and 7.

Test Tube Adaptor

Figure 42:
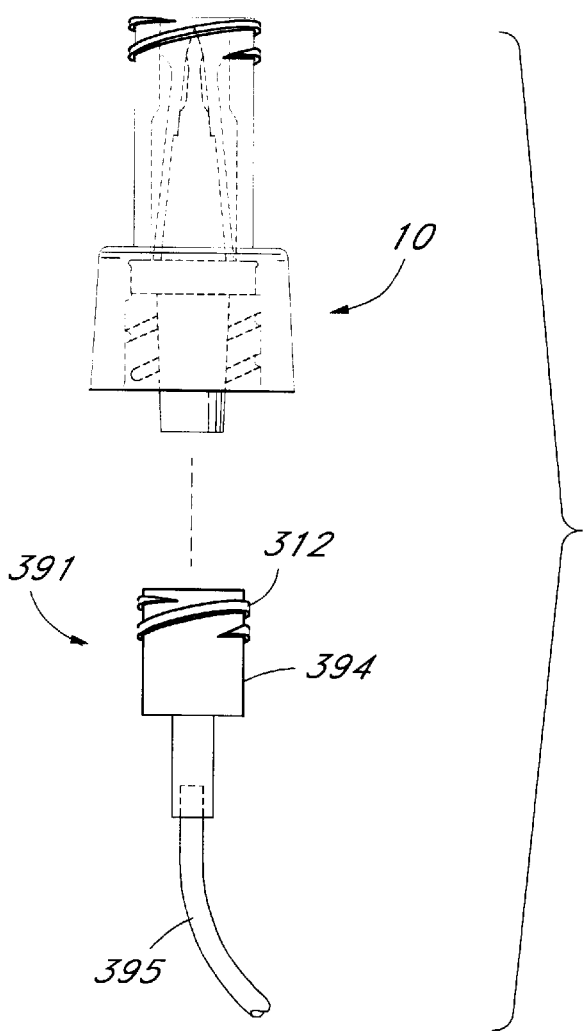
FIG. 42 is a partially exploded side view of a test tube adaptor made in accordance with the present invention.
Figure 43:
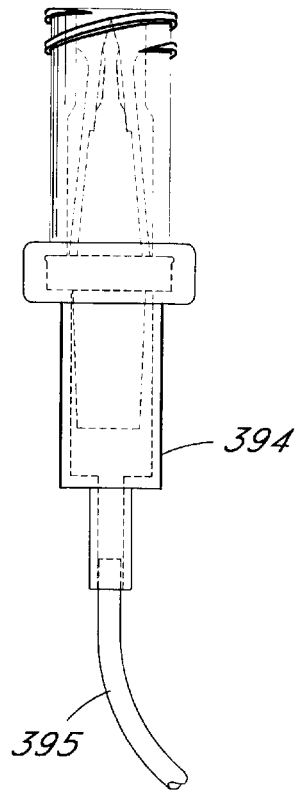
FIG. 43 is a side view of another embodiment of the test tube adaptor, having an integral valve.

FIGS. 42 and 43 illustrate yet another embodiment of the present invention. A test tube adaptor 391 is provided to function as a device for withdrawing fluid from, or depositing fluid into, a test tube or other narrowly necked container. The test tube adaptor 391 either attaches to a medical valve 10 or 11 as previously described, as shown in FIG. 42; or is a single piece having an integral medical valve 10 or 11, as shown in FIG. 43.

The test tube adaptor 391 is preferably made of any medically inert material. In the preferred embodiment of the test tube adaptor 391, and especially where disposability is desired, the test tube adaptor 391 is constructed of plastic. In other embodiments, however, and particularly where reusability is desired, the test tube adaptor 391 may be made of stainless steel or any like substance, to allow sterilization in an autoclave or similar device.

As shown in FIG. 42, the test tube adaptor 391 has a generally cylindrical tubular body 394 with a proximal and a distal end, and an open-ended tube 395 at the distal end.

The tube 395 is preferably flexible, and transparent, so that a user can see whether fluid is flowing therein. In the preferred embodiment the tube 395 is constructed of flexible medical tubing. In addition, the tube 395 should be of a length sufficient to reach substantially into a test tube or similar narrowly necked container, so that fluids can be withdrawn. In the preferred embodiment, the tube 395 is approximately 5.5 inches long. The tube 395 should also have an inner diameter sufficient to allow fluids, especially liquids, to pass easily therethrough. In the preferred embodiment, the tube 395 has an inner diameter of approximately 0.03 inches.

The body 394 is generally cylindrical, although it may also be conical or have a neck to accommodate the change in diameter from its proximal end to the distal end where the tube 395 is attached.

In one preferred embodiment of the adaptor 391, shown in FIG. 42, the proximal end of the adaptor 391 is provided with a locking mechanism 392 that preferably comprises a Luer-Lock device or other locking device known to those of skill in the art. The locking mechanism 392 is adapted to removably and sealable connect the proximal end of the adaptor 391 to a medical valve 10 or 11, as previously described.

Alternatively, as shown in FIG. 43, the proximal end of the adaptor 391 could be provided with an integral medical valve 10 or 11.

In use, the tube 395 of the adaptor 391 is placed into the test tube or other container. If using an adaptor 391 of the type shown in FIG. 42, a medical value 10 or 11 of the first preferred embodiment must be attached to the proximal end of the adaptor 391, using the locking mechanism 392. The tip or nose of an ANSI standard syringe, IV set, or other connector, is then pushed into the proximal end of the medical valve 10 or 11. Referring now to FIGS. 6 and 7, this action pushes the tip 32 of the spike 26 through the seal 36, exposing the through holes 34 and thus bringing the syringe into fluid communication with the adaptor 391 and the test tube. The valve connection process is more extensively described above with reference to FIGS. 6 and 7.

The foregoing provides a description of the best mode contemplated of carrying out the present invention, and of the manner and process of making and using it, in such full, clear, concise, and exact terms as to enable any person skilled in the art to which it pertains to make and use the invention. Although certain embodiments have been described, it is intended that the scope of the invention not be limited to the specific embodiments described. It will be appreciated that certain modification and variations may suggest themselves to those skilled in the art. The spirit and scope of the invention are limited solely by the following claims.

What is claimed is:

1. A medical valve adaptor for use in controlling the flow of fluid to or from a medical implement and a fluid container, said valve adaptor comprising:

a first body having a proximal end and a distal end and a cavity therein, said proximal end of said body adapted for engagement with said first medical implement;

a seal located in said cavity, said seal moveable between a first position in which a fluid flow path is established through said body and a second position in which fluid is prevented from flowing through said body;

a spike positioned in said cavity of said first body, said spike having a fluid path therethrough and said seal positioned adjacent said spike;

a second body having a proximal end and a distal end and a fluid flow path therethrough, said distal end of said second body being connected to said distal end of said first body; and an open-ended tube adapted to extend into an opening of a container, said tube extending from said proximal end of said second body;

wherein when said medical implement is connected to said first body and said seal is in said first position and said tube is extended into said container, fluid is allowed to flow between said container and said medical implement and wherein in said first position the seal is opened by the spike and a flow path is established between said medical implement said proximal end of said first body, and in said second position said seal is not opened by the spike so that the flow path is closed.

2. The adaptor of claim 1, wherein said spike has a tip adapted for fluid communication with said medical implement when said seal is in said first position and wherein said seal is spaced from said tip when said seal is in said second position.

3. The adaptor of claim 1, wherein said spike has a tip and a hole in a side thereof near said tip, said hole leading to a passage through said spike.

4. A medical valve adaptor for use in controlling the flow of fluid or from a medical implement and a fluid container, said valve adaptor comprising:

a first body having a proximal end and a distal end and a cavity therein;

a spike in said cavity of said first body;

a seal adjacent to said spike, said seal being moveable between a first position in which said spike penetrates said seal to establish a flow path through said first body and a second position in which said spike does not penetrate said seal and in which said flow path is closed;

a second body having a proximal end and a distal end, said distal end of said second body being connected to said distal end of said first body; and an open-ended tube extending from said proximal end of said second body to penetrate the fluid container.

5. The adaptor of claim 4, wherein said spike has a tip adapted for fluid communication with said medical implement when said seal is in said first position and wherein said seal is spaced from said tip when said seal is in said second position.

6. The adaptor of claim 4, wherein said spike has a tip and at least one hole at or near said tip, said at least one hole leading to a passage through said spike.

7. The adaptor of claim 4, wherein said spike has a tip and at least two holes at or near said tip, said at least two holes leading to a passage through said spike.

8. The adaptor of claim 4, wherein said first and second bodies are integrally connected.

9. The adaptor of claim 4, wherein said proximal end of said first body has an opening therein and said seal in said second position fills essentially completely said opening.

10. The adaptor of claim 4, wherein said seal in said second position fills essentially completely said cavity.

11. The adaptor of claim 4, wherein said open-ended tube has a generally frustoconical shape.

12. A system for transferring fluid, comprising:
- a first body having proximal and distal ends, and a cavity therein;
- a spike located within said cavity;
- a seal located on said spike, said seal being compressible between a first position in which said spike penetrates said seal to establish a flow path through said first body and a second position in which said spike does not penetrate said seal and in which said flow path is closed;
- a second body having proximal and distal ends, said distal end of said second body being connected to said distal end of said first body and in communication therewith;
- an open-ended tube extending from said proximal end of said second body; and
- a syringe in communication with said first body, said syringe adapted to compress said seal between said first position and said second position.

13. A system for transferring fluid, comprising:
- a first body having proximal and distal ends, and a cavity therein;
- a spike located within said cavity;
- a seal located on said spike, said seal being compressible between a first position in which said spike penetrates said seal to establish a flow path through said first body and a second position in which said spike does not penetrate said seal and in which said flow path is closed;
- a second body having proximal and distal ends, said distal end of said second body being connected to said distal end of said first body and in communication therewith;
- an open-ended tube extending from said proximal end of said second body;
- a drip bag, said drip bag in communication with said open-ended tube; and
- a syringe, said syringe adapted to compress said seal between said first position and said second position.

* * * * *

Disclaimer

6,599,273—George A. Lopez, Corona del Mar, CA (US). FLUID TRANSFER DEVICE AND METHOD OF USE. Patent dated July 29, 2003. Disclaimer filed Sept. 7, 2006, by the Assignee, ICU Medical, Inc.

The term of this patent shall not extend beyond the expiration date of Pat. No. 6,572,592; 6,132,403; 5,928,204; 5,873,862 and 5,685,866.

(*Official Gazette May 22, 2007*)